(12) United States Patent
Reynolds et al.

(10) Patent No.: US 9,518,109 B2
(45) Date of Patent: Dec. 13, 2016

(54) **PREVENTION, TREATMENT AND DIAGNOSIS OF *P. GINGIVALIS* INFECTION**

(71) Applicant: Oral Health Australia PTY Ltd, Carlton, Victoria (AU)

(72) Inventors: Eric Charles Reynolds, Melbourne (AU); Neil Martin O'Brien Simpson, Melbourne (AU); Keith J Cross, Melbourne (AU); Nada Slakeski, Melbourne (AU)

(73) Assignee: ORAL HEALTH AUSTRALIA PTY LTD, Carlton, Victoria (AU)

( * ) Notice: Subject to any disclaimer, the term of this patent is extended or adjusted under 35 U.S.C. 154(b) by 0 days.

(21) Appl. No.: 14/487,461

(22) Filed: Sep. 16, 2014

(65) Prior Publication Data

US 2015/0079095 A1    Mar. 19, 2015

Related U.S. Application Data

(63) Continuation of application No. 13/060,653, filed as application No. PCT/AU2009/001112 on Aug. 28, 2009, now Pat. No. 8,871,213.

(60) Provisional application No. 61/151,132, filed on Feb. 9, 2009.

(30) Foreign Application Priority Data

Aug. 29, 2008 (AU) ................ 2008904476
Oct. 23, 2008 (AU) ................ 2008905483
Jun. 30, 2009 (AU) ................ 2009903052

(51) Int. Cl.

| | | |
|---|---|---|
| C07K 16/00 | (2006.01) | |
| C07K 16/12 | (2006.01) | |
| C07K 14/195 | (2006.01) | |
| A61K 39/02 | (2006.01) | |
| G01N 33/569 | (2006.01) | |
| C12N 9/14 | (2006.01) | |
| C12N 9/52 | (2006.01) | |
| A61K 39/00 | (2006.01) | |

(52) U.S. Cl.

CPC ....... *C07K 16/1257* (2013.01); *A61K 39/0216* (2013.01); *C07K 14/195* (2013.01); *C12N 9/14* (2013.01); *C12N 9/52* (2013.01); *G01N 33/56955* (2013.01); *A61K 2039/53* (2013.01); *A61K 2039/55566* (2013.01); *C07K 2317/34* (2013.01); *C07K 2317/76* (2013.01); *C12Y 304/21004* (2013.01); *C12Y 306/05002* (2013.01)

(58) Field of Classification Search
None
See application file for complete search history.

(56) References Cited

U.S. PATENT DOCUMENTS

| | | |
|---|---|---|
| 4,603,112 A | 7/1986 | Paoletti et al. |
| 4,735,801 A | 4/1988 | Stocker |
| 4,837,151 A | 6/1989 | Stocker |
| 5,210,035 A | 5/1993 | Stocker |
| 5,475,097 A | 12/1995 | Travis et al. |
| 5,523,390 A | 6/1996 | Travis et al. |
| 5,707,620 A | 1/1998 | Travis et al. |
| 5,711,937 A | 1/1998 | Nishida et al. |
| 6,129,917 A | 10/2000 | Potempa et al. |
| 6,274,718 B1 | 8/2001 | Travis et al. |
| 6,444,799 B1 | 9/2002 | Ross |
| 6,511,666 B1 | 1/2003 | Reynolds et al. |
| 6,528,038 B1 | 3/2003 | Reynolds et al. |
| 6,726,898 B2 | 4/2004 | Jernberg |
| 6,962,706 B1 | 11/2005 | O'Brien-Simpson et al. |
| 7,204,991 B2 | 4/2007 | Barr et al. |
| 7,262,271 B2 | 8/2007 | Reynolds et al. |
| 7,341,727 B1 | 3/2008 | Tucker et al. |
| 7,419,671 B2 | 9/2008 | Reynolds et al. |
| 7,544,777 B2 | 6/2009 | Ross et al. |
| 7,749,502 B2 | 7/2010 | Reynolds et al. |
| 8,106,152 B2 | 1/2012 | Reynolds et al. |
| 8,241,611 B2 | 8/2012 | Dashper et al. |
| 8,282,933 B2 | 10/2012 | Reynolds et al. |
| 8,313,749 B2 | 11/2012 | Shi et al. |
| 8,349,575 B2 | 1/2013 | McKenzie et al. |
| 8,431,688 B2 | 4/2013 | Reynolds et al. |
| 8,642,731 B2 * | 2/2014 | Ross .............. A61K 8/64 424/278.1 |
| 8,673,363 B2 | 3/2014 | Reynolds et al. |
| 8,765,144 B2 | 7/2014 | Reynolds et al. |
| 8,784,831 B2 | 7/2014 | Reynolds et al. |
| 8,841,420 B2 | 9/2014 | Reynolds et al. |
| 8,871,213 B2 | 10/2014 | Reynolds et al. |

(Continued)

FOREIGN PATENT DOCUMENTS

| | | |
|---|---|---|
| JP | 2013-087087 A | 5/2013 |
| WO | WO 95/00110 | 1/1995 |

(Continued)

OTHER PUBLICATIONS

Office Action issued on Jan. 30, 2015 in U.S. Appl. No. 14/161,961 (US 2014/0302083).
Frazer et al., "Vaccination with recombinant adhesions from the RgpA-Kgp proteinase-adhesin complex protects against *Porphyromonas gingivalis* infection," Vaccine, vol. 24, pp. 6542-6554, Jun. 2006.
McGraw et al., "Purification, Characterization, and Sequence Analysis of a Potential Virulence Factor from *Porphyromonas gingivalis*, Peptidylarginine Deiminase," Infection and Immunity, vol. 67, No. 7, pp. 3248-3256, Jul. 1999.
Rosenstein et al., "Hypothesis: The Humoral Immune Response to Oral Bacteria Provides a Stimulus for the Development of Rheumatoid Arthritis," Inflammation, vol. 28, No. 6, pp. 311-318, 2004.

(Continued)

*Primary Examiner* — Nita M Minnifield
(74) *Attorney, Agent, or Firm* — Foley & Lardner LLP

(57) ABSTRACT

The invention relates to generation and use of cellular and humoral responses for the prevention and treatment of *P. gingivalis* related conditions and diseases.

12 Claims, 7 Drawing Sheets

(56) References Cited

U.S. PATENT DOCUMENTS

| | | | |
|---|---|---|---|
| 8,916,166 B2* | 12/2014 | Dashper | A61K 38/164 424/190.1 |
| 8,975,032 B2* | 3/2015 | Nozoe | C07K 14/195 435/7.1 |
| 2003/0083287 A1 | 5/2003 | Burgess et al. | |
| 2005/0288866 A1 | 12/2005 | Sachdeva et al. | |
| 2006/0078950 A1 | 4/2006 | Progulske-Fox et al. | |
| 2007/0036734 A1 | 2/2007 | Tahara et al. | |
| 2007/0098649 A1 | 5/2007 | Wu et al. | |
| 2010/0034908 A1 | 2/2010 | Ross et al. | |
| 2010/0092471 A1 | 4/2010 | Dashper et al. | |
| 2010/0297179 A1 | 11/2010 | Dashper et al. | |
| 2011/0213129 A1 | 9/2011 | Reynolds et al. | |
| 2012/0156211 A1 | 6/2012 | McCluskey et al. | |
| 2013/0129768 A1 | 5/2013 | Reynolds et al. | |
| 2013/0236488 A1 | 9/2013 | Dashper et al. | |
| 2013/0316371 A1* | 11/2013 | Nozoe | C07K 14/195 435/7.9 |
| 2015/0079095 A1* | 3/2015 | Reynolds | A61K 39/0216 424/139.1 |

FOREIGN PATENT DOCUMENTS

| | | |
|---|---|---|
| WO | WO 95/007286 | 3/1995 |
| WO | WO 95/09181 A1 | 4/1995 |
| WO | WO 95/11298 | 4/1995 |
| WO | WO 95/26404 A1 | 10/1995 |
| WO | WO 96/17936 A2 | 6/1996 |
| WO | WO 97/34629 A1 | 9/1997 |
| WO | WO 00/67917 | 11/2000 |
| WO | WO 00/75346 A1 | 12/2000 |
| WO | WO 02/102370 | 12/2002 |
| WO | WO 03/055529 | 7/2003 |
| WO | WO 03/080113 | 10/2003 |
| WO | WO 2005/019249 A2 | 3/2005 |
| WO | WO 2008/016385 A2 | 2/2008 |
| WO | WO 2008/124646 A2 | 10/2008 |
| WO | WO 2011/027257 A2 | 3/2011 |
| WO | WO 2012/081306 A1 | 6/2012 |

OTHER PUBLICATIONS

International Search Report issued on Nov. 1, 2005 in application No. PCT/AU2005/001463 (corresponding to US 2009/0175867 and US 2011/0081358).
International Search Report issued on Aug. 17, 2007 in application No. PCT/AU2007/000890 (corresponding to US 2010/0092471).
International Search Report issued on Oct. 13, 2009 in application No. PCT/AU2009/001112 (corresponding to U.S. Appl. No. 13/060,653).
International Search Report issued on Jan. 31, 1997 in application No. PCT/AU96/00673 (corresponding to U.S. Pat. No. 6,511,666 and US 2007/0189982).
International Search Report issued on Jan. 28, 1999 in application No. PCT/AU98/01023 (corresponding to U.S. Pat. No. 7,544,777 and US 2010/0034908).
International Search Report issued on Sep. 12, 2008 in application No. PCT/AU2008/001018 (corresponding to U.S. Appl. No. 12/668,407).
International Search Report issued on Sep. 12, 2008 in application No. PCT/Au2008/001017 (corresponding to US 2010/0297179).
Office Action issued on Dec. 27, 2010 in U.S. Appl. No. 12/306,495 (US 2010/0092471).
Office Action issued on Jun. 3, 2010 in U.S. Appl. No. 12/306,495 (US 2010/0092471).
Office Action issued on Mar. 23, 2010 in U.S. Appl. No. 12/306,495 (US 2010/0092471).
Notice of Allowance issued on Dec. 5, 2008 in U.S. Appl. No. 11/589, 261 (US 7,544,777).
Office Action issued on May 19, 2008 in U.S. Appl. No. 11/589,261 (US 7,544,777).
Office Action issued on Oct. 30, 2007 in U.S. Appl. No. 11/589,261 (US 7,544,777).
Office Action issued on Apr. 28, 2006 in U.S. Appl. No. 09/581,286.
Office Action issued on Sep. 16, 2005 in U.S. Appl. No. 09/581,286.
Office Action issued on Mar. 24, 2005 in U.S. Appl. No. 09/581,286.
Office Action issued on Aug. 25, 2004 in U.S. Appl. No. 09/581,286.
Office Action issued on Jan. 27, 2004 in U.S. Appl. No. 09/581,286.
Office Action issued on Oct. 1, 2002 in U.S. Appl. No. 09/581,286.
Office Action issued on Nov. 2, 2010 in U.S. Appl. No. 12/382,845 (US 2010/0034908).
Office Action issued on Sep. 17, 2010 in U.S. Appl. No. 11/654,512 (US 2007/0189982).
Office Action issued on Aug. 12, 2009 in U.S. Appl. No. 11/654,512 (US 2007/0189982).
Office Action issued on Oct. 23, 2008 in U.S. Appl. No. 11/654,512 (US 2007/0189982).
Office Action issued on Feb. 7, 2008 in U.S. Appl. No. 11/654,512 (US 2007/0189982).
Office Action issued on Aug. 21, 2007 in U.S. Appl. No. 11/654,512 (US 2007/0189982).
Office Action issued on Oct. 29, 2009 in U.S. Appl. No. 11/729,218 (US 2008/0175867).
Office Action issued on Apr. 10, 2009 in U.S. Appl. No. 11/729,218 (US 2008/0175867).
Office Action issued on Aug. 28, 2008 in U.S. Appl. No. 11/728,218 (US 2008/0175867).
Notice of Allowance issued on Oct. 7, 2013 in U.S. Appl. No. 13/400,987 (U.S. Pat. No. 8,642,731).
Office Action issued on May 13, 2013 in U.S. Appl. No. 13/060,653 (U.S. Pat. No. 8,871,213).
Office Action issued on Oct. 21, 2013 in U.S. Appl. No. 13/060,653 (U.S. Pat. No. 8,871,213).
Notice of Allowance issued on Jun. 18, 2014 in U.S. Appl. No. 13/060,653 (U.S. Pat. No. 8,871,213).
Kyte et al., "A simple method for displaying the hydropathic character of a protein," Journal of Molecular Biology, vol. 157, Issue 1, pp. 105-132, May 1982, Abstract.
Aduse Opoku et al., "Characterization, Genetic Analysis, and Expression of a Protease Antigen (PrpRl) of Porphyromonas gingivalis W50," Infection & Immunity, vol. 63, No. 12, pp. 4744-4754, Dec. 1995.
Barkocy-Gallagher et al., "Analysis of the prtP Gene Encoding Porphypain, a Cysteine Proteinase of Porphyromonas gingivalis," J. of Bacteriolgy, vol. 178, No. 10, May 1996.
Bedi, "Comparative Study of Four Proteases from Spent Culture Media of Porphyromonas gingivalis (FAY-19M-1)," Preparative Biochemistry, pp. 133-154, Aug. 1995.
Ciborowski, "Purification and Characterization of Two Forms of a High-Molecular-Weight Cysteine Proteinase (Porphypain) from Porphyromonas gingivalis," J. of Bacteriology, pp. 4549-4557, 1994.
Okamoto et al., "Structural Characterization of Argingipain, a Novel Arginine-Specific Cysteine Proteinase as a Major Periodontal Pathogenic Factor from Porphyromonas gingivalis," Archives of Biochemistry & Biophysics, vol. 316, No. 2, pp. 917-925, Feb. 1, 1995.
Pavloff et al., "Molecular Cloning and Structural Characterization of the Arg-gingipain Proteinase of Porphyromonas gingivalis," J. of Biol. Chem., vol. 270, No. 3, pp. 1007-1010, Jan. 20, 1995.
Pike et al., "Lysine- and Arginine-specific Proteinases from Porphyromonas gingivalis," J. of Biol. Chem., vol. 269, No. 1, pp. 406-411, Jan. 7, 1994.
Slakeski et al., "Characterization of a Porphyromnas gingivalis Gene prtR That Encodes an Arginine-Specific Thiol Porteinase and Multiple Adhesins," Biochem. & Biophys. Res. Comm., vol. 224, pp. 605-610, 1996.
Yoshimura, "Characterization of a Trypsin-Like Protease From the Bacterium Bacteroides Gingivalis Isolated From Human Dental Plaque," Archs. Oral. Biol.,vol. 29, No. 7, pp. 559-564, 1984.
Albandar et al., Destructive periodontal disease in adults 30 years of age and older in the United States, 1988-1994, Journal of Periodontology, vol. 70, pp. 13- 29, 1999.

(56) References Cited

OTHER PUBLICATIONS

Alm et al., The MicrobesOnline Web site for comparative genomics, Genome Research, vol. 15, pp. 1015-1022, 2005.
Bramanti et al. Roles of porphyrins and host iron transport proteins in regulation of growth of Porphyromonas gingivalis W50, Journal of Bacteriology, vol. 173, pp. 7330-7339, 1991.
Brochu et al., Acquisition of iron from human transferrin by Porphyromonas gingivalis: a role for Arg- and Lys-gingipain activities, Oral Microbiology and Immunology, vol. 16, pp. 79-87, 2001.
Capestany et al., Role of the Poiphyromonas gingivalis InlJ Protein in Homotypic and Heterotypic Biofilm Development, Infection and Immunity, vol. 74, pp. 3002-3005, 2006.
Carter et al., Humanization of an Anti-p185HER2 Antibody for Human Cancer Therapy, Proceedings of the National Academy of Science USA, vol. 89, pp. 4285-4289, 1989.
Chen et al., Porphyromonas gingivalis gingipains and adhesion to epithelial cells, Infection and Immunity, vol. 69, pp. 3048-3056, 2001.
Cossart et aL, Bacterial invasion: the paradigms of enteroinvasive pathogens, Science, vol. 304, pp. 242-248, 2004.
Curtiss et al., A virulent Salmonella typhimurium Acya Acrp oral vaccine strains expressing a streptococcal colonization and virulence antigen, Vaccine, vol. 6, pp. 155-160, 1988.
Dashper et al., Characterization of a novel outer membrane hernin-binding protein of Porphyromonas gingivalis, Journal of Bacteriololgy., vol. 182, pp. 6456-6462, 2000.
Dashper et al., Sodium ion-driven serine/threonine transport in Porphyromonas gingivalis, Journal of Bacteriology, vol. 183, pp. 4142-4148, 2001.
Dashper et al., Hemoglobin hydrolysis and haem acquisition by Porphyromonas gingivalis, Oral Microbiology and Immunology, vol. 9, pp. 50-56, 2004.
Dashper et al., A novel Porphyromonas gingivalis FeoB plays a role in manganese accumulation, The Journal of Biological Chemistry, vol. 280, pp. 28095-28102, 2005.
Database Ref. Seq, Accession Nos. NC_002950.2 and N13_904903, Jan. 12, 2009.
Devereaux et al., A comprehensive set of sequence analysis programs for the VAX, Nucleic Acids Research, vol. 12, pp. 387-395, 1984.
Diaz et al., The effect of oxygen on the growth and physiology of Porphyromonas gingivalis, Oral Microbiology and Immunology, vol. 19, pp. 88-94, 2004.
Diaz et al., Role of oxyR in the oral anaerobe Porphyromonas gingivalis, Journal of Bacteriology, vol. 188, pp. 2454-2462, 2006.
Dramsi et al., Entry of Listeria monocytogenes into hepatoeytes requires expression of in inlB, a surface protein of the internalin multigene family, Molecular Microbiology, vol. 16, pp. 251-261, 1995.
Duran-Pinedo et al., The RprY response regulator of Porphyromonas gingivalis, Molecular Microbiology, vol. 64, pp. 1416, 2007.
Eymann et al., A comprehensive proteome map of growing Bacillus subtilis cells, Proteomics, vol. 4, pp. 2849-2876, 2004.
Fletcher et al., Virulence of a Porphyramonas gingivalis W83 mutant defective in the prtH gene, Infection and Immunity, vol. 63, pp. 1521-1528, 1995.
Genco et al., Characterization of a Tn4351-generated hemin uptake mutant of Porphyramonas gingivalis: evidence for the coordinate regulation of virulence factors by hemin, Infection and Immunity, vol. 63, pp. 2459-2466, 1995.
Guina et al., Quantitative proteomic analysis indicates increased synthesis of a quinolone by Pseudomonas aeruginosa isolates from cystic fibrosis airways, Proceedings of the National Academy of Science USA, vol. 100, pp. 2771-2776, 2003.
Haffajee et al., Microbial etiological agents of destructive periodontal diseases, Periodontology 2000, vol. 5, pp. 78-111, 1994.
Huse et al., Generation of a large combinatorial library of the immunoglobulin repertoire in phage lambda, Science, vol. 246, pp. 1275-1281, 1989.
Jones et al., Replacing the complementarity-determining regions in a human antibody with those from a mouse, Nature, vol. 321, pp. 522-525, 1986.
Lamont et aL, Interaction of Porphyromonas gingivalis with gingival epithelial cells maintained in culture, Oral Microbiology and Immunology, vol. 7, pp. 364-367, 1992.
Lamont et al., Porphyromonas gingivalis invasion of gingival epithelial cells, Infection and Immunity, vol. 63, pp. 3878-3885, 1995.
Li et al., Protein profiling with cleavable isotope-coded affinity tag (cICAT) reagents: the yeast salinity stress response, Molecular and Cellular Proteomics, vol. 2, pp. 1198-1204, 2003.
Marino et al., A framework for interpreting the leucine-rich repeats of the Listeria intemalins, Proceedings of the National Academy of Science USA, vol. 97, pp. 8784-8788, 2000.
McKee et al., Effect of hemin on the physiology and virulence of Bacteroides gingivalis W50, Infection and Immunity, vol. 52, pp. 349-355, 1986.
Moore et al., The bacteria of periodontal diseases, Periodontology 2000, vol. 5, pp. 66-77, 1994.
Needleman et al., A general method applicable to the search for similarities in the amino acid sequence of two proteins, Journal of Molecular Biology, vol. 443-453, 1970.
Nelson et al., Complete genome sequence of the oral pathogenic Bacterium Potphyromonas gingivalis strain W83, Journal of Bacteriology, vol. 185, pp. 5591-5601, 2003.
Okano et al., Proteomics-based analysis of a counter-oxidative stress system in Porphyromonas gingivalis, Proteomics, vol. 6, pp. 251-258, 2006.
Park et al., Identification of Porphyromonas gingivalis genes specifically expressed in human gingival epithelial cells by using differential display reverse transcription-PCR, Infection and Immunity, vol. 72, pp. 3752-3758, 2004.
Pathirana et al., Flow cytometric analysis of adherence of Porphyromonas gingivalis to oral epithelial cells, Infection and Immunity, vol. 75, pp. 2484-2492, 2007.
Peng et al., Evaluation of multidimensional chromatography coupled with tandem mass spectrometry (LC/LC-MS/MS) for large-scale protein analysis: the yeast proteome, Journal of Proteome Research, vol. 2, pp. 43-50, 2003.
Price et al., A novel method for accurate operon predictions in all sequenced prokaryotes, Nucleic Acids Research, vol. 33, pp. 880-892, 2005.
Reichman et al., Reshaping human antibodies for therapy, Natu e, vol. 332, pp. 323-327, 1988.
Ross et al., Identification of vaccine candidate antigens from a genomic analysis of Porphyromonas gingivalis, Vaccine, vol. 19, pp. 4135-4142, 2001.
Sabet et al., LPXTG protein In1J, a newly identified internalin involved in Listeria monocytogenes virulence, Infection and Immunity, vol. 73, pp. 6912-6922, 2005.
Schifferle et al., Effect of protoporphyrin DC limitation on Porphyromonas gingivalis, Journal of Endodonics, vol. 22, pp. 352-355, 1996.
Schramm et al., Nucleotide sequence of the colicin B activity gene cba: consensus pentapeptide among TonB-dependent colicins and receptors, Journal of Bacteriology, vol. 169, pp. 3350-3357, 1987.
Schubert et al., Structure of internalin, a major invasion protein of Listeria monocytogenes, in complex with its human receptor E-cadherin, Cell, vol. 111, pp. 825-836, 2002.
Seers et aL, The RgpB C-terminal domain has a role in attachment of RgpB to the outer membrane and belongs to a novel C-terminal-domain family found in Porphyromonas gingivalis, Journal of Bacteriology, vol. 188, pp. 6376-6386, 2006.
Shah et al., The porphyrin pigmentation of subspecies of Bacteroides melaninogenicus, Biochemical Journal, vol. 180, pp. 45-50, 1979.
Sharp et al., The codon Adaptation Index—a measure of directional synonymous codon usage bias, and its potential applications, Nucleic Acids Research, vol. 15, pp. 1281-1295, 1987.
Shi et al., Genetic analyses of proteolysis, hemoglobin binding, and hemagglutination of Porphyromonas gingivalis. Construction of

(56) References Cited

OTHER PUBLICATIONS mutants with a combination of rgpA, rpgl3, kgp, and hagA, The Journal of Biological Chemistry, vol. 274, pp. 17955-17604, 1999.

Shizukuishi et al., Effect of concentration of compounds containing iron on the growth of Porphyromonas gingivalis, FEMS Microbiology Letters, vol. 131, pp. 313-317, 1995.

Simpson et al., Characterization and expression of HmuR, a Tonl3-dependent hemoglobin receptor of Porphyromonas gingivalis, Journal of Bacteriology, vol. 182, pp. 5737-5748, 2000.

Smalley et al. Hacinin-binding proteins of Porphyromonas gingivalis W50 grown in a chemostat under haemin-1 imitation. Journal of General Microbiology, 1993, vol. 139, pp. 2145-2150.

Smalley et al., The periodontopathogen Porphyromonas gingivalis binds iron protoporphyrin IX in the mu-oxo dimeric form: an oxidative buffer and possible pathogenic mechanism, Biochemical Journal, vol. 331 (Pt3), pp. 681-685, 1998.

Smalley et al., The periodontal pathogen Porphyromonas gingivalis harnesses the chemistry of the mu-oxo bishaem of iron protoporphyrin IX to protect against hydrogen peroxide, FEMS Microbiology Letters, vol. 183, pp. 159-164, 2000.

Supek et al., INCA: synonymous codon usage analysis and clustering by means of self-organizing map, Bioinformatics, vol. 20, pp. 2329-2330, 2004.

Thompson et al., CLUSTAL W: improving the sensitivity of progressive multiple sequence alignment through sequence weighting, position-specific gap penalties and weight matrix choice, Nucleic Acids Research, vol. 22, pp. 4673-4680, 1994.

Tribble et al., A Porphyromonas gingivalis haloacid dehalogenase family phosphatase interacts with human phosphoproteins and is important for invasion, Proceedings of the National Academy of Science USA, vol. 103, pp. 11027-11032, 2006.

Veith et al., Identification of a novel heterodimeric outer membrane protein of Porphyromonas gingivalis by two-dimensional gel electrophoresis and peptide mass fingerprinting, European Journal of Biochemistry, vol. 268, pp. 4748-4757, 2001.

Wang et al., An analysis of the proteomic profile for Thermoanaerobacter tengcongensis under optimal culture conditions, Proteomics, vol. 4, pp. 136-150, 2004.

Washburn et al., Large-scale analysis of the yeast proteome by multidimensional protein identification technology, Nature Biotechnology, vol. 19, pp. 242-247, 2001.

Yu et al., Predicting subcellular localization of proteins for Gram-negative bacteria by support vector machines based on n-peptide compositions, Protein Science, vol. 13, pp. 1402-1406, 2004.

Zhang et al., Differential protein expression by Porphyromonas gingivalis in response to secreted epithelial cell components, Proteomics, vol. 5, pp. 198-211, 2005.

Houghten et al., "Relative Importance of Position and Individual Amino Acid Residues in Peptide Antigen-Antibody Interactions: Implications in the Mechanism of Antigenic Drift and Antigenic Shift Vaccines," 1986, Fred Brown, Ed.

Lederman et al., "A Single Amino Acid Substitution in a Common African Allele of the CD4 Molecule Ablates Binding of the Monoclonal Antibody, OKT4," Molecular Immunology, vol. 28, pp. 1171-1181, 1991.

Li et al., "β-Endorphin omission analogs: Disssociation of immunoreactivity from other biological activities," Proc. Natl. Acad. Sci. USA, vol. 77, pp. 3211-3214, 1980.

Campbell, "Assay Techniques," Monoclonal Antibody Technology, Chapter 2, 1986.

Bohgal et al., "A cell-associated protein complex of *Porphyromonas gingivalis* W50 composed of Arg- and Lys-specific cysteine proteinases and adhesins," Microbiology, vol. 143, pp. 2485-2495, 1997.

Davey et al., "Enhanced Biofilm Formation and Loss of Capsule Synthesis: Deletion of a Putative Glycosyltransferase in *Porphyromonas gingivalis*," J. Bacteriology, vol. 188, No. 15, pp. 5510-5523, 2006.

Chung et al., "Identification of a *Porphyromonas gingivalis* Receptor for the *Streptococcus gordonii* SspB Protein," Infection and Immunity, vol. 68, No. 12, pp. 6758-6762, 2000.

Xie et al., "*Porphyromonas gingivalis* Genes involved in fimA Regulation," Infection and Immunity, vol. 72, No. 2, pp. 651-658, 2004.

Daep et al., "Structural Characterization of Peptide-mediated inhibition of *Porphyromonas gingivalis* biofilm formation," Infection and Immunity, vol. 74, No. 10, pp. 5756-5762, 2006.

Mendz et al., "Fumarate Reductase: A Target for Therapeutic Intervention against *Helicobacter pylori*," Archives of Biochemistry and Biophysics, vol. 321, No. 1, pp. 153-159, 1995.

Takahashi et al., "Metabolic Pathways for Cytotoxic End Product Formation from Aspartate-Containing Peptides by *Porphyromonas gingivalis*," J. Bacteriol., vol. 182, No. 17, pp. 4704-4710, 2000.

Office Action issued on May 12, 2010 in U.S. Appl. No. 11/663,671 (US 2009/0169568).

Office Action issued on Nov. 4, 2009 in U.S. Appl. No. 11/663,671 (US 2009/0169568).

O'Brien-Simpson et al., "RgpA-Kgp Peptide-Based Immunogens Provide Protection Against porphyromonas gingivalis Challenge in Murine Lesion Model," Infection and Immunity, 68(7): 4055-4063, 2000.

Office Action issued on Jul. 9, 2010 in U.S Appl. No. 12/382,845 (US 2010/0034908).

* cited by examiner

US 9,518,109 B2

PREVENTION, TREATMENT AND DIAGNOSIS OF *P. GINGIVALIS* INFECTION

FIELD OF THE INVENTION

The invention relates to peptides and chimeric or fusion proteins and to the use of these proteins to elicit cellular and humoral responses for the prevention and treatment of *P. gingivalis*-related conditions and diseases.

BACKGROUND OF THE INVENTION

Chronic periodontitis is an inflammatory disease of the supporting tissues of the teeth leading to resorption of alveolar bone and eventual tooth loss. The disease is a major public health problem in all societies and is estimated to affect up to 15% of the adult population with severe forms affecting 5-6%.

The development and progression of chronic periodontitis has been associated with specific Gram-negative bacteria in subgingival plaque. The presence of *Porphyromonas gingivalis* in subgingival plaque has been strongly associated with disease.

The persistence of *P. gingivalis* in subgingival plaque from periodontitis patients after treatment (scaling and root planing) has been reported to be significantly associated with progressive alveolar bone loss. Furthermore an increase in *P. gingivalis* cell numbers in subgingival plaque has been shown to correlate with disease severity as measured by attachment loss, periodontal pocket depth and bleeding on probing.

Oral infection with *P. gingivalis* has been shown to induce periodontal bone loss in mice, rats and non-human primates. In addition, there has been increasing linkage of periodontal disease, and of *P. gingivalis* infection, with cardiovascular diseases and certain cancers.

A number of virulence factors have been reported to contribute to the pathogenicity of *P. gingivalis* including; LPS, fimbriae, hemagglutinin, hemolysin and extracellular hydrolytic enzymes (especially the Arg-X and Lys-X specific proteinases), otherwise known as "*P. gingivalis* trypsin-like enzymes".

The magnitude of the public health problem is such that there is a need for an antiserum, particularly specific antibodies that provide a strong protective response to *P. gingivalis* infection and means for providing same.

One problem has been that it is not clear how to obtain a strong protective response to *P. gingivalis* infection where there are a plethora of virulence factors to select from.

The relative immunogenicity of epitopes amongst virulence factors is not well understood, nor is the relative immunogenicity of epitopes on a given factor, particularly where it is not clear as to whether further epitopes remain to be identified.

One particular problem has been that many virulence factors are formed from multiple domains and are difficult to express so as to present a conformation approaching that found on *P. gingivalis*. Further, when these domains are expressed as discrete units i.e. in isolation of other virulence factor domains, they tend to fold into a conformation distinguished from that found on *P. gingivalis*.

Further, of the many different options for modifying the immunogenicity of a virulence factor it is not clear which would be most likely to provide for a protective immune response.

In work leading to the present invention the inventors have identified peptides having an amino acid sequence that is the same as, or that shares homology with, an amino acid sequence that forms a region of a *P. gingivalis* trypsin-like enzyme, said region defining a site in said enzyme for cleavage of a peptide bond located C-terminal to Lys or Arg in a peptide containing Lys or Arg, and incorporated such a peptide into a chimeric or fusion protein which, when used as a vaccine, provides better protection against periodontal tissue destruction than purified proteinase-adhesin complex formed from native *P. gingivalis* trypsin-like enzyme or killed whole cells.

SUMMARY OF THE INVENTION

In one aspect, the present invention provides a chimeric or fusion protein for inducing an immune response to *P. gingivalis*, the protein including a first peptide joined directly or through a linker to a second peptide, wherein:
  (A) said first peptide includes:
    (i) part of, or all of a sequence that is the same as, or homologous to the sequence shown in SEQ ID No:1; or
    (ii) part of, or all of a sequence that is the same as, or homologous to the sequence shown in SEQ ID No:2; and
  (B) said second peptide includes:
    (i) part of, or all of a sequence that is the same as, or homologous to the sequence of an adhesin domain of the Lys-X-proteinase of *P. gingivalis*; or
    (ii) part of, or all of a sequence that is the same as, or homologous to the sequence of an adhesin domain of the Arg-X-proteinase of *P. gingivalis*; or
    (iii) part of, or all of a sequence that is the same as, or homologous to the sequence of a HagA adhesin domain of *P. gingivalis*.

In another aspect, the invention provides a chimeric or fusion protein for inducing an immune response to *P. gingivalis*, the protein including a peptide joined directly or through a linker to a polypeptide, wherein:
  (A) said peptide includes:
    (i) part of, or all of a sequence that is the same as, or homologous to the sequence shown in SEQ ID No:1; or
    (ii) part of, or all of a sequence that is the same as, or homologous to the sequence shown in SEQ ID No:2; and
  (B) said polypeptide includes:
    (i) part of, or all of a sequence that is the same as, or homologous to the sequence of an adhesin domain of the Lys-X-proteinase of *P. gingivalis*; or
    (ii) part of, or all of a sequence that is the same as, or homologous to the sequence of an adhesin domain of the Arg-X-proteinase of *P. gingivalis*; or
    (iii) part of, or all of a sequence that is the same as, or homologous to the sequence of a HagA adhesin domain of *P. gingivalis*.

In another aspect, the invention provides a peptide for inducing an immune response to *P. gingivalis* the peptide having a sequence:
  (i) that is the same as, or homologous to the sequence shown in one of SEQ ID No: 64 to 66; and
  (ii) that is the same as, or homologous to the sequence shown in SEQ ID No: 67 or 68.

In one aspect, the peptide having a sequence that is the same as or homologous to sequence shown in one of SEQ ID No: 64 to 68 may be provided in the form of a chimeric or fusion protein in which the peptide is joined directly or through a linker to a second peptide, wherein the second peptide includes:
- (i) part of, or all of a sequence that is the same as, or homologous to the sequence of an adhesin domain of the Lys-X-proteinase of *P. gingivalis*; or
- (ii) part of, or all of a sequence that is the same as, or homologous to the sequence of an adhesin domain of the Arg-X-proteinase of *P. gingivalis*; or
- (iii) part of, or all of a sequence that is the same as, or homologous to the sequence of a HagA adhesin domain of *P. gingivalis*.

In yet another aspect, the invention provides a composition such as an antigenic composition, particularly a vaccine composition, including a chimeric or fusion protein or peptide as broadly described above, optionally in association with an adjuvant.

In this aspect, the invention also provides a method of preventing or reducing the incidence or severity of a *P. gingivalis*-related condition or disease in a subject, which comprises administering to the subject a chimeric or fusion protein as described above, or a composition as described above.

In this aspect, the invention further provides the use of a chimeric or fusion protein as described above, or a composition as described above, in, or in the manufacture of a medicament for preventing or reducing the incidence or severity of a *P. gingivalis* related condition or disease in a subject.

In another aspect, the invention provides an antibody, particularly a monoclonal antibody, raised against a chimeric or fusion protein or peptide as broadly described above.

In this aspect, the invention also provides a method of preventing or reducing the severity of a *P. gingivalis*-related disease or condition in a subject, which comprises administering to the subject an antibody as described above.

In this aspect, the invention further provides the use of an antibody as described above in, or in the manufacture of a medicament for preventing or reducing the incidence or severity of a *P. gingivalis*-related condition or disease in a subject.

In yet another aspect, the invention also provides a nucleic acid molecule including a nucleotide sequence encoding a chimeric or fusion protein as broadly described above, optionally operatively linked to at least one regulatory element.

In this aspect, the invention further provides a vector including such a nucleic acid molecule, as well as a prokaryotic or eukaryotic cell including such a nucleic acid molecule.

In this aspect, the invention also provides a method of preventing or reducing the incidence or severity of a *P. gingivalis*-related condition or disease in a subject, which comprises administering to the subject a nucleic acid molecule as described above, a vector as described above, or a prokaryotic or eukaryotic cell as described above.

In this aspect, the invention further provides the use of a nucleic acid molecule as described above, a vector as described above, or a prokaryotic or eukaryotic cell as described above, in, or in the manufacture of a medicament for preventing or reducing the severity of a *P. gingivalis*-related disease or condition in a subject.

In a further aspect, the invention provides a method for the diagnosis or monitoring of a *P. gingivalis*-related condition or disease in a subject, which comprises use of a chimeric or fusion protein as described above to detect anti-*P. gingivalis* antibodies in a biological sample from said subject.

In this aspect, the invention also provides the use of a chimeric or fusion protein as described above, to detect anti-*P. gingivalis* antibodies in a biological sample from a subject.

In yet another aspect, the invention provides a method for the diagnosis or monitoring of a *P. gingivalis*-related condition or disease in a subject, which comprises use of an antibody as described above, to detect the presence of *P. gingivalis* in a biological sample from said subject.

In this aspect, the invention also provides the use of an antibody as described above, to detect the presence of *P. gingivalis* in a biological sample from a subject.

In another aspect, the invention provides a use of a peptide having part of, or all of a sequence that is the same as, or homologous to a sequence of a *P. gingivalis* Lys-X or Arg-X proteinase, or a nucleic acid encoding said peptide for the manufacture of a chimeric or fusion protein for inducing an immune response to *P. gingivalis*. In this aspect the peptide may have a sequence shown in one of SEQ ID No: 17, 18, 25 or 26.

DETAILED DESCRIPTION OF THE EMBODIMENTS

Figure 1:
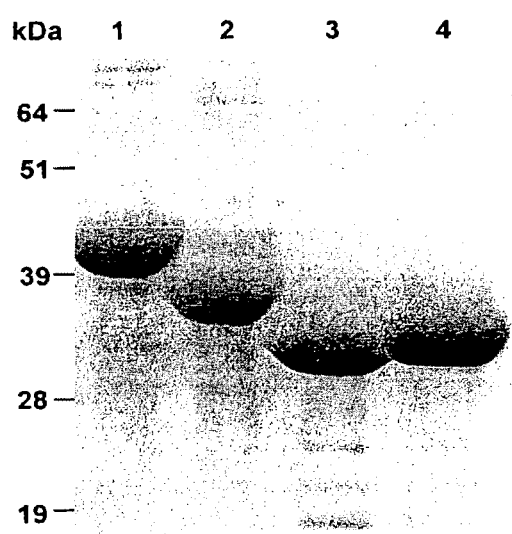
FIG. 1 shows a Coomassie blue stain of the SDS-PAGE gel of recombinant Kgp Proteins. Lane 1=KAS2-KLA1, Lane 2=KLA1, Lane 3=KsA1, Lane 4=KAS1-KsA1. Molecular weight markers are indicated as kDa.

It will be understood that the invention disclosed and defined in this specification extends to all alternative combinations of two or more of the individual features mentioned or evident from the text or drawings. All of these different combinations constitute various alternative aspects of the invention.

The inventors have found that the regions of *P. gingivalis* trypsin-like enzymes that flank or otherwise define a catalytic or active site for cleavage of a peptide bond are highly immunogenic and indeed sufficient to provide for a humoral response to *P. gingivalis* infection. In particular, it has been found that a chimeric or fusion protein including one or more of these regions provides protection against alveolar bone loss which is greater than that seen for antisera raised against whole cells and other immunogens. The finding is particularly surprising as, to date, the catalytic domain of trypsin-like enzymes of *P. gingivalis* has been found to be relatively weakly immunogenic.

In one aspect, the present invention provides a chimeric or fusion protein for inducing an immune response to *P. gingivalis*, the protein including a first peptide joined directly or through a linker to a second peptide, wherein:
  (A) said first peptide includes:
    (i) part of, or all of a sequence that is the same as, or homologous to the sequence shown in SEQ ID No:1; or
    (ii) part of, or all of a sequence that is the same as, or homologous to the sequence shown in SEQ ID No:2; and
  (B) said second peptide includes:
    (i) part of, or all of a sequence that is the same as, or homologous to the sequence of an adhesin domain of the Lys-X-proteinase of *P. gingivalis*; or
    (ii) part of, or all of a sequence that is the same as, or homologous to the sequence of an adhesin domain of the Arg-X-proteinase of *P. gingivalis*; or
    (iii) part of, or all of a sequence that is the same as, or homologous to the sequence of a HagA adhesin domain of *P. gingivalis*.

As used herein, the term "peptide" is used to refer to an amino acid sequence of up to about 40 amino acid residues, preferably from 5 to 40 amino acid residues.

In one embodiment, a polypeptide is used in place of or in other words instead of the "second peptide". The term "polypeptide" is used to refer to an amino acid sequence of at least about 40 amino acid residues.

Thus, in another aspect there is provided a chimeric or fusion protein for inducing an immune response to *P. gingivalis*, the protein including a peptide joined directly or through a linker to a polypeptide, wherein:
  (A) said peptide includes:
    (i) part of, or all of a sequence that is the same as, or homologous to the sequence shown in SEQ ID No:1; or
    (ii) part of, or all of a sequence that is the same as, or homologous to the sequence shown in SEQ ID No:2; and
  (B) said polypeptide includes:
    (i) part of, or all of a sequence that is the same as, or homologous to the sequence of an adhesin domain of the Lys-X-proteinase of *P. gingivalis*; or
    (ii) part of, or all of a sequence that is the same as, or homologous to the sequence of an adhesin domain of the Arg-X-proteinase of *P. gingivalis*; or
    (iii) part of, or all of a sequence that is the same as, or homologous to the sequence of a HagA adhesin domain of *P. gingivalis*.

In another aspect, the invention provides a peptide for inducing an immune response to *P. gingivalis* selected from the group consisting of:
  (i) a sequence that is the same as or homologous to the sequence shown in one of SEQ ID No: 64 to 66; and
  (ii) a sequence that is the same as or homologous to the sequence shown in SEQ ID No: 67 or 68.

In an aspect of the invention, where the peptide has a sequence of SEQ ID No: 64 to 68, the peptide may be provided in the form of a chimeric or fusion protein in which the peptide is joined directly or through a linker to a second peptide. In an embodiment, the second peptide of the chimeric or fusion protein includes:
  (i) part of, or all of a sequence that is the same as, or homologous to the sequence of an adhesin domain of the Lys-X-proteinase of *P. gingivalis*; or
  (ii) part of, or all of a sequence that is the same as, or homologous to the sequence of an adhesin domain of the Arg-X-proteinase of *P. gingivalis*; or
  (iii) part of, or all of a sequence that is the same as, or homologous to the sequence of a HagA adhesin domain of *P. gingivalis*.

In the above described embodiment a polypeptide is used in place of, or in other words instead of the second peptide. Thus, in another aspect there is provided a chimeric or fusion protein for inducing an immune response to *P. gingivalis*, the protein including a peptide joined directly or through a linker to a polypeptide, wherein:
  (A) said peptide includes:
    (i) a sequence that is the same as or homologous to the sequence shown in one of SEQ ID No: 64 to 66; or
    (ii) a sequence that is the same as or homologous to the sequence shown in SEQ ID No: 67 or 68.; and (B) said polypeptide includes:
   (i) part of, or all of a sequence that is the same as, or homologous to the sequence of an adhesin domain of the Lys-X-proteinase of *P. gingivalis*; or
   (ii) part of, or all of a sequence that is the same as, or homologous to the sequence of an adhesin domain of the Arg-X-proteinase of *P. gingivalis*; or
   (iii) part of, or all of a sequence that is the same as, or homologous to the sequence of a HagA adhesin domain of *P. gingivalis*.

As used herein, a reference to a "homologue" of a peptide or polypeptide is a reference to a peptide or polypeptide having an amino acid sequence that shares homology or that is homlogous to, or that has identity with the amino acid sequence of the first-mentioned peptide or polypeptide, preferably at least 90% sequence identity, more preferably at least 95% and even more preferably at least 98% sequence identity when the comparison is performed by a BLAST algorithm wherein the parameters of the algorithm are selected to give the largest match between the respective sequences over the entire length of the respective reference sequences. Sequence identity refers to exact matches between the amino acids of two sequences which are being compared. Such a homologue may derive from a naturally occurring variant or isolate of the Lys-X-proteinase or Arg-X-proteinase of *P. gingivalis*. Alternatively, it may be a "conservative-substitution" variant of a peptide or polypeptide from the Lys-X-proteinase or Arg-X-proteinase of *P. gingivalis* in which one or more amino acid residues have been changed without altering the overall conformation and function of the peptide or polypeptide; including, but by no means limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine. Preferably such conservative-substitution variants have less than 20, more preferably less than 15, more preferably less than 10, and most preferably less than 5 amino acid changes.

Figure 7:
FIG. 7. Protein model of the Kgp proteinase. KAS2 [Asn433-Lys468]. (A) KAS4 [Asp388-Val395] (B), KAS5 [Asn510-Asp516] (C) and KAS6 [Ile570-Tyr580] (D).

A region of a *P. gingivalis* trypsin-like enzyme—especially a Lys-X-proteinase (Kgp) or Arg-X-proteinase (RgpA)—that defines a site in an enzyme for cleavage of a peptide bond can be determined following the teaching of the specification herein, particularly in relation to FIG. 7 and Example 9, which exemplify the process for predicting three-dimensional conformation of the catalytic site as it appears on *P. gingivalis* for Lys-X-proteinase. Example 10 provides methodology for modelling of the Arg-X-proteinase three-dimensional conformation.

In certain embodiments, the chimeric or fusion protein, or first or second peptide components thereof may be formed from a peptidomimetic. A peptidomimetic is a molecule that mimics one or more characteristics of a given peptide, for example conformation, and that consists of amino acid residues, some of which may not be naturally occurring.

Having identified the immunogenic regions of the catalytic site, the inventors have determined the sequence of various peptide immunogens against which a humoral response can be raised. In particular, 'six' regions that flank or otherwise define the catalytic site have been defined as follows: KAS1/RAS1, KAS2/RAS2, KAS3/RAS3, KAS4/RAS4, KAS5/RAS5 and KAS6 (see Table 1). With this information, the inventors have been able to interrogate protein sequence databases to determine peptides that share homology with amino acid sequences that form regions that flank a catalytic site and hence that represent immunogenic epitopes found on *P. gingivalis*. The sequence of these peptides are identified by the following structural formula:

TABLE 1

Sequences that flank the active site of Kgp and RgpA.

| Region | Kgp Lys - X (numbering according to SEQ ID No.62) | Kgp Lys - X Consensus | RgpA Arg -X (numbering according to SEQ ID No.61) | RgpA Arg -X Consensus |
|---|---|---|---|---|
| PAS1K/ PAS1R | PAS 1K (432-453) | LNTGVSFANYTAHGS ETAWADP (SEQ ID NO: 30) | PAS1R(426-446) | FNGGISLANYTGHGSET AWGT (SEQ ID NO: 34) |
| KAS1/ RAS1 | KAS1 (432-454) | LNTGV[G/S]FANYTAH GSET[S/A]WADP[S/L] (SEQ ID NO: 27) | RAS1 (426-448) | FNGGISL[V/A]NYTGHG SETAWGTSH (SEQ ID NO: 31) |
| KAS2/ RAS2 | KAS2 (433-468) | NTGV[G/S]FANYTAHG SET[S/A]WADP[S/L][L/ V]T[A/T][T/S]Q[V/L]KAL TNK[D/N]K (SEQ ID NO: 28) | RAS2 (427-462) | NGGISL[V/A]NYTGHGS ETAWGTSHFGTTHVKQ LTNSNQ (SEQ ID NO: 32) |
| KAS3/ RAS3 | KAS3 (436-455) | V[G/S]FANYTAHGSET [S/A]WADP[S/L][L/V] (SEQ ID NO: 29) | RAS3 (430-449) | ISL[V/A]NYTGHGSETA WGTSHF (SEQ ID NO: 33) |
| KAS4/ RAS4 | KAS4 (388-395) | D[S/Y][Y/S]WN[P/S][K/ Q][I/V](SEQ ID NO: 64) | RAS4 (379-386) | EGGPSADN (SEQ ID NO: 67) |
| KAS5/ RAS5 | KAS5 (510-516) | NSYWGED (SEQ ID NO: 65) | RAS5 (508-514) | [N/D]Q[S/Y]WA[S/P]P (SEQ ID NO: 68) |
| KAS6 | KAS6 (570-580) | IGN[V/I]THIGAHY (SEQ ID NO: 66) | | |

The inventors have found that chimeric proteins including these peptides have a number of utilities. For example, as described herein, some produce a humoral response that is highly protective for treatment or prevention of bone loss as observed in chronic periodonitis. The peptides may also be used in a diagnostic assay wherein they can detect or monitor specificities in an individual's serum, thereby indicating whether or not the individual is infected and if so, whether treatments are required or if provided, whether they have been effective.

It will be understood that the region of a *P. gingivalis* trypsin-like enzyme that defines a site in the enzyme for cleavage of a peptide bond located C-terminal to Lys or Arg, does not comprise a complete sequence of the Lys-X-proteinase or Arg-X-proteinase.

As used herein, the terms "heterologous protein" or "chimeric or fusion protein" are used to refer to a protein that is composed of functional units, domains, sequences or regions of amino acids derived from different sources or that are derived from the same source and that have been assembled so as to have an organisation that is distinguished from that observed in a molecule from which the unit, domain, sequence or region is derived or related to. A common feature of the chimeric or fusion proteins of the invention is that they contain at least one peptide having an amino acid sequence that is the same as or that shares homology with a sequence of a *P. gingivalis* trypsin-like enzyme that defines a catalytic site for cleavage of a peptide bond.

In a preferred embodiment, where the first peptide comprises a peptide from the Kgp[432-468] region, it is preferably (i) a peptide which comprises a sequence selected from VSFANYT and VGFANYT, more preferably a sequence selected from GVSFANYT, GVGFANYT, VSFANYTA and VGFANYTA; or (ii) a peptide which comprises a sequence selected from ETAWAD, ETSWAD, TAWADP and TSWADP, preferably a sequence selected from SETAWAD, SETSWAD, ETAWADP, ETSWADP, TAWADPL and TSWADPL, more preferably a sequence selected from GSETAWAD, GSETSWAD, SETAWADP, SETSWADP, ETAWADPL, ETSWADPL, TAWADPLL and TSWADPLL. More preferably, this peptide is selected from the KAS1 [432-454], KAS2[433-468] and KAS3[436-455] peptides shown in Table 1. Alternatively, the first peptide may be the PAS1K[432-453] peptide, also known as PAS1(K48), disclosed in International Patent Application No. PCT/AU98/00311 (WO 98/049192). The sequence identifiers corresponding to these peptides are shown in Table 3.

Similarly, in another preferred embodiment, where the first peptide comprises a peptide from the RgpA[426-462] region, this peptide is preferably selected from the RAS1 [426-448], RAS2[427-462] and RAS3[430-449] peptides shown in Table 1. Alternatively, the first peptide may be the PAS1R[426-446] peptide, also known as PAS1(R45), disclosed in International Patent Application No. PCT/AU98/00311 (WO 98/049192).

In the chimeric or fusion protein of the invention, the second peptide may be a peptide from an adhesin domain of a *P. gingivalis* trypsin-like enzyme, such as Lys-X-proteinase (Kgp) or Arg-X-proteinase (RgpA) or HagA (see Table 2). These domains are sometimes also known as hemagglutinins. In the Lys-X-proteinase, the preferred domains are KA1, KA2, KA3, KA4, KA5 as identified in Table 2. In the Arg-X-proteinase, the preferred domains are RA1, RA2, RA3 and RA4 as identified in Table 2. In HagA, the preferred domains are HagA1, HagA1* and HagA1**

TABLE 2

Adhesin domains of the Kgp and RgpA proteinases.

|  | A1 | sA1 | LA1 | A2 | A3 | A4 | A5 |
|---|---|---|---|---|---|---|---|
| Kgp Lys-X proteinase SEQ ID No. 62 | KA1 (738-1099) SEQ ID NO: 35 | KsA1 (759-989) SEQ ID NO: 36 | KLA1 (751-1056) SEQ ID NO: 37 | KA2 (1157-1275) SEQ ID NO: 40 | KA3 (1292-1424) SEQ ID NO: 41 | KA4 (1427-1546) SEQ ID NO: 42 | KA5 (1548-1732) SEQ ID NO: 43 |
| RgpA Arg-X proteinase SEQ ID No. 61 | RA1 (720-1081) SEQ ID NO: 38 | RsA1 (831-971) SEQ ID NO: 39 | — | RA2 (1139-1257) SEQ ID NO: 44 | RA3 (1274-1404) SEQ ID NO: 45 | RA4 (1432-1706) SEQ ID NO: 46 | — |
| HagA SEQ ID NO. 63 | HagA1 (26-351) (SEQ ID NO: 80), HagA1* (366-625) (SEQ ID NO: 81), HagA1** (820-1077) (SEQ ID NO: 82) or HagA1** (1272-1529) (SEQ ID NO: 82) |  |  |  |  |  |  |

In addition to improving the humoral response to a peptide of the invention such as KAS1, KAS2, KAS3, KAS4, KAS5 and KAS6 or RAS1, RAS2 and RAS3, RAS4 and RAS5 when included with such a peptide in a chimeric or fusion protein, the adhesin domain also contains immunogenic epitopes, hence leading to the production of multiple specificities to elicit a protective immunogenic response. The finding that the immunogenic epitopes of the adhesin domain are retained in a form approaching that in a *P. gingivalis* trypsin-like enzyme when provided in the chimeric or fusion protein of the invention is unanticipated.

It will be understood that in these embodiments of the invention the chimeric or fusion protein may contain any one or more of the peptides selected from KAS1/RAS1, KAS2/RAS2, KAS3/RAS3, KAS4/RAS4, KAS5/RAS5 and KAS6/RAS6 together with any one or more adhesin domains of a *P. gingivalis* trypsin-like enzyme, in particular with any one or more of Lys-X-proteinase adhesin domains (KA1, KA2, KA3, KA4 and KA5) or Arg-X-proteinase adhesin domains (RA1, RA2, RA3 and RA4) or HagA domains HagA1, HagA1* and HagA1**.

It will also be understood that it is not necessary for the adhesin domain to be a complete domain as observed in a *P. gingivalis* trypsin-like enzyme. For example the adhesin domain may be a fragment of such a domain, in particular, preferred fragments are the KsA1 and KLA1 domain fragments of the Lys-X-proteinase A1 domain (see Table 2). Where the domain is a fragment of an adhesin domain it generally contains one or more adhesin domain specific epitopes.

The sequence identifiers corresponding to the adhesin related peptides are shown in Table 3.

In one embodiment the second peptide or polypeptide includes a sequence shown in one or more of SEQ ID No: 69 to 79 or one or more of 83 to 85.

The chimeric or fusion protein of the present invention may also include one or more additional peptides selected from the Kgp[432-468] region of the Lys-X-proteinase and/or one or more additional peptides selected from the RgpA[426-462] region of the Arg-X-proteinase.

In preferred embodiments of the present invention, the chimeric or fusion protein includes one or more of KAS1, KAS2, KAS3, KAS4, KAS5 and KAS6, or one or more of RAS1, RAS2, RAS3, RAS4 and RAS5, together with KsA1 or KLA1.

Thus in certain embodiments, the chimeric or fusion protein may include at least one further peptide wherein said further peptide includes:
(i) part of, or all of a sequence that is the same as, or homologous to the sequence shown in SEQ ID No:1; or
(ii) part of, or all of a sequence that is the same as, or homologous to the sequence shown in SEQ ID No:2; or
(iii) part of, or all of a sequence that is the same as, or homologous to the sequence of an adhesin domain of the Lys-X-proteinase of *P. gingivalis*; or
(iv) part of, or all of a sequence that is the same as, or homologous to the sequence of an adhesin domain of the Arg-X-proteinase of *P. gingivalis*; or
(v) part of, or all of a sequence that is the same as, or homologous to the sequence of a HagA adhesin domain of *P. gingivalis*.

Other examples of domains, units, sequences or regions that may be included in a chimeric or fusion protein as described herein include domains for binding to receptors or ligands such as Fc binding regions or Fc receptors, domains for improving half-life such as albumin or domains for facilitating expression or purification of the chimeric or fusion protein.

In the chimeric or fusion proteins of the present invention, the C-terminal residue of the first peptide may be covalently linked to the N-terminal residue of an adhesin domain polypeptide, or the N-terminal residue of the first peptide may be covalently linked to the C-terminal residue of an adhesin domain polypeptide. In this arrangement, the first peptide and adhesin domain polypeptide, are said to be "directly linked" or "adjacent".

In other embodiments, the chimeric or fusion protein includes a linker for linking the first peptide to an adhesin domain polypeptide. The linker may be any linker able to join a peptide to a polypeptide, including both amino acid and non-amino acid linkers. Preferably, the linker is non-immunogenic. Suitable linkers may be up to 15 amino acids in length, although less than five amino acids is preferred. The linker may function to bring the first peptide and adhesin domain polypeptide into a closer spatial arrangement than normally observed in a *P. gingivalis* trypsin-like enzyme. Alternatively, it may space the first peptide and adhesin domain polypeptide apart.

The chimeric or fusion proteins of the invention may be produced by recombinant expression systems (such as recombinant DNA technology) or by chemical synthesis (such as solid phase peptide synthesis). These techniques are well known in the art.

The heterologous or chimeric protein is particularly advantageous because it improves the humoral response obtained over that obtained using the first or second peptide components of the chimeric or fusion protein alone.

The inventors have found that chimeric proteins including these peptides have a number of utilities. For example, as described herein, some produce a humoral response that is highly protective for treatment or prevention of bone loss as observed in chronic periodontitis. The peptides may also be used in a diagnostic assay wherein they can detect or monitor specificities in an individual's serum, thereby indicating whether or not the individual is infected and if so, whether treatments are required or if provided, whether they have been effective.

In one embodiment, the chimeric or fusion protein induces a protective immune response, typically a response that at least minimises or limits connective tissue damage otherwise associated with *P. gingivalis* infection. In one embodiment the protective response at least minimises or limits *P. gingivalis* induced bone loss. A model system for measuring bone loss mediated by *P. gingivalis* infection is discussed herein. Typically the protective immune response is predominantly a humoral response. In certain embodiments the protective immune response also includes a cellular response.

The present invention also provides a composition including a chimeric or fusion protein as broadly described above. Typically the composition is antigenic or immunogenic. More particularly, the invention provides a composition suitable for eliciting a protective or therapeutic immune response against *P. gingivalis* infection, including the chimeric or fusion protein, optionally in association with an adjuvant. Such a composition may also include another component for modulating or potentiating the immune response. One embodiment, the composition takes the form of a vaccine.

Various adjuvants are known for use in conjunction with vaccine compositions. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant (IFA), Adjuvant 65 (containing peanut oil, mannide monooleate and aluminium monostearate), oil emulsions, Ribi adjuvant, the pluronic polyols, polyamines, Avridine, Quil A®, saponin, MPL®, QS-21, mineral gels such as aluminium salts and calcium salts, nanoparticles such as hydroxyapatite, calcium phosphate, aluminium salts, sugar oligomers and polymers such as mannan, chitosan. Other examples include oil in water emulsions such as SAF-1, SAF-O, MF59®, Seppic ISA720, and other particulate adjuvants such ISCOMs™ and ISCOM Matrix™. An extensive but not exhaustive list of other examples of adjuvants are listed in Cox and Coulter 1992 [In: Wong WK (ed.) *Animals parasite control utilising technology*. Bocca Raton; CRC press, 1992; 49-112]. In addition to the adjuvant, the vaccine composition may include conventional pharmaceutically acceptable carriers, excipients, fillers, buffers or diluents as appropriate. One or more doses of the vaccine composition containing adjuvant may be administered prophylactically to prevent periodontitis or therapeutically to treat already present periodontitis.

In a preferred composition, the chimeric or fusion protein is combined with a mucosal adjuvant and administered via the oral, buccal or nasal route. Examples of mucosal adjuvants are nanoparticles, cholera toxin and heat labile *E. coli* toxin, the non-toxic B subunits of these toxins, genetic mutants of these toxins which have a reduced toxicity. Other methods which may be utilised to deliver the antigenic protein orally/buccally/nasally include incorporation or absorption of the protein into or onto particles of biodegradable polymer (such as acrylates or polyesters) or nanoparticles (such as hydroxyapatite) by microencapsulation to aid uptake of the microspheres from the gastrointestinal tract or other mucosal surfaces and to protect degradation of the proteins. Liposomes, ISCOMs™, hydrogels are examples of other potential methods which may be further enhanced by the incorporation of targeting molecules such as LTB, CTB or lectins for delivery of the antigenic protein to the mucosal immune system. In addition to the antigenic protein and the mucosal adjuvant or delivery system, the vaccine composition may include conventional pharmaceutically acceptable carriers, excipients, fillers, coatings, dispersion media, antibacterial or antifungal agents, and buffers or diluents as appropriate.

In this aspect, the invention also provides a method of preventing or reducing the incidence or severity of a *P. gingivalis*-related condition or disease in a subject, which comprises administering to the subject a chimeric or fusion protein as described above, or an composition as described above.

The subject may be a human or other animal subject, and is preferably a human.

Typically, the *P. gingivalis*-related condition or disease is chronic periodontis, however it may also be bone loss, especially alveolar bone loss, or coronary artery disease.

Many methods are known for administration of a vaccine composition to a human or animal subject, including but not limited to intradermal, intramuscular, intraperitoneal, intravenous, subcutaneous, intranasal, sub-lingual, buccal and oral administration. These routes of administration are particularly useful for vaccination.

In another aspect, the invention provides an antibody, preferably a monoclonal antibody, raised against a chimeric or fusion protein as broadly described above.

These antibodies may be produced by standard techniques, and may be used in passive immunisation of a subject. Accordingly, in this aspect, the invention also provides a method of preventing or reducing the severity of a *P. gingivalis*-related disease or condition in a subject, which comprises administering to the subject an antibody as described above.

In a further aspect, the present invention provides a nucleic acid molecule including a nucleotide sequence encoding a chimeric or fusion protein as broadly described above, optionally operatively linked to at least one regulatory element. In one embodiment the nucleic acid is provided in isolated or substantially purified form.

The nucleic acid molecule may, for example, be inserted into a suitable expression vector for production of the chimeric protein as a recombinant protein by insertion of the expression vector into a prokaryotic or eukaryotic host cell. Successful expression of the recombinant protein requires that the expression vector contains the necessary regulatory elements for transcription and translation which are compatible with, and recognised by the particular host cell system used for expression. A variety of host cell systems may be utilized to express the recombinant protein, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc).

Using methods known in the art of molecular biology, various promoters and enhancers can be incorporated into the expression vector, to increase the expression of the recombinant protein, provided that the increased expression of the amino acid sequences is compatible with (for example, non-toxic to) the particular host cell system used.

The selection of the promoter will depend on the expression system used. Promoters vary in strength, i.e. ability to facilitate transcription. Generally, it is desirable to use a strong promoter in order to obtain a high level of transcription of the coding nucleotide sequence and expression into recombinant protein. For example, bacterial, phage, or plasmid promoters known in the art from which a high level of transcription have been observed in a host cell system including *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted nucleotide sequence encoding amino acid sequences.

Other control elements for efficient transcription or translation include enhancers, and regulatory signals. Enhancer sequences are DNA elements that appear to increase transcriptional efficiency in a manner relatively independent of their position and orientation with respect to a nearby coding nucleotide sequence. Thus, depending on the host cell expression vector system used, an enhancer may be placed either upstream or downstream from the inserted coding sequences to increase transcriptional efficiency. Other regulatory sites, such as transcription or translation initiation signals, can be used to regulate the expression of the coding sequence.

In another embodiment, the vector may be a viral or bacterial vaccine vector, and used to provide a recombinant viral vaccine, a recombinant bacterial vaccine, a recombinant attenuated bacterial vaccine, or an inactivated recombinant viral vaccine. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens thereby providing long lasting immunity.

Other live vaccine vectors include: adenovirus, cytomegalovirus, and preferably the poxviruses such as vaccinia [Paoletti and Panicali, U.S. Pat. No. 4,603,112] and attenuated *Salmonella* strains [Stocker of al., U.S. Pat. Nos. 5,210,035; 4,837,151; and 4,735,801; and Curtiss et al., 1988, *Vaccine* 6:155-160]. Live vaccines are particularly advantageous because they continually stimulate the immune system which can confer substantially long-lasting immunity. When the immune response is protective against subsequent *P. gingivalis* infection, the live vaccine itself may be used in a preventive vaccine against *P. gingivalis*. In particular, the live vaccine can be based on a bacterium that is a commensal inhabitant of the oral cavity. This bacterium can be transformed with a vector carrying a recombinant chimeric protein and then used to colonise the oral cavity, in particular the oral mucosa. Once colonised in the oral mucosa, the expression of the recombinant protein will stimulate the mucosal associated lymphoid tissue to produce neutralising antibodies. To further illustrate this embodiment, using molecular biological techniques well known in the art, nucleotide sequences encoding the chimeric proteins of this invention may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen and without substantially affecting the immunogenicity of the expressed immunogen. The inactivated recombinant-vaccine may be formulated with a suitable adjuvant in order to enhance the immunological response to the vaccine antigens.

The invention also provides for the use of a nucleic acid molecule including a nucleotide sequence encoding a chimeric or fusion protein of this invention directly as the vaccine formulation. Nucleotide sequences encoding the chimeric proteins, operatively linked to one or more regulatory elements, can be introduced directly to vaccinate an individual ("direct gene transfer") against pathogenic strains of *P. gingivalis*. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex [Zhu et al., 1993, *Science* 261:209-211]. Other effective methods for delivering vector DNA into a target cell are known in the art. In one example, purified recombinant plasmid DNA containing viral genes has been used to inoculate (whether parenterally, mucosally, or via gene-gun immunization) vaccines to induce a protective immune response [Fynan et al. 1993, *Proc Natl Acad Sci USA* 90:11478-11482]. In another example, cells removed from an individual can be transfected or electroporated by standard procedures known in the art, resulting in the introduction of the recombinant vector DNA intro the target cell. Cells containing the recombinant vector DNA may then be selected for using methods known in the art, such as by use of a selection marker expressed in the vector, and the selected cells may then be re-introduced into the individual to express the recombinant protein.

In this aspect, the invention further provides a method of preventing or reducing the incidence or severity of a *P. gingivalis*-related condition or disease in a subject, which comprises administering to the subject a nucleic acid molecule as described above, a vector as described above, or a prokaryotic or eukaryotic cell as described above.

In other embodiments there is provided a pharmaceutical composition including a chimeric or fusion protein or an antibody as described above. The composition may further include diluent, excipient, or carrier or chemotherapeutic agent for treatment of a *P. gingivalis*-related condition or disease and may be adapted for oral administration. The compositions of this invention may be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

An oral composition of this invention which contains the above-mentioned pharmaceutical composition may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. An oral composition according to this invention may further include additional well known ingredients depending on the type and form of a particular oral composition.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 5 to about 9 and typically from about 5.0 to 7.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In other desirable forms of this invention, the pharmaceutical composition may be substantially solid or pasty in character, such as toothpowder, a dental tablet or a toothpaste (dental cream) or gel dentifrice. The vehicle of such solid or pasty oral preparations generally contains dentally acceptable polishing material.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5- 30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite® (e.g. CP, SP 2002, D) marketed by Laporte Industries Limited. Laponite® D is, approximately by weight 58.00% SiO2, 25.40% MgO, 3.05% Na2O, 0.98% Li2O, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid® (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a bottle of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic® materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract or periodontal pocket and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives or antimicrobial agents, for example benzoates, such as ethyl, or n-propyl p-hydroxybenzoate another example is chlorhexidine gluconate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

In a further aspect, the present invention provides a method for the diagnosis or monitoring of a *P. gingivalis*-related condition or disease in a subject, which comprises use of a chimeric or fusion protein as described above to detect anti-*P. gingivalis* antibodies in a biological sample from said subject.

In yet another aspect, the invention provides a method for the diagnosis or monitoring of a *P. gingivalis*-related condition or disease in a subject, which comprises use of an antibody as described above, to detect the presence of *P. gingivalis* in a biological sample from said subject.

In yet another aspect, the invention provides a peptide for inducing an immune response to *P. gingivalis* including the sequence shown in one of SEQ ID No: 17, 18, 25 and 26. In one embodiment, the peptide has a sequence that is homologous to one of SEQ ID No: 17, 18, 25 and 26. The peptide may have a length of 5 to 40 amino acids.

In yet another aspect, the invention provides a nucleic acid encoding a peptide having a sequence shown in one of SEQ ID No: 17, 18, 25 and 26.

In yet another aspect, the invention provides a use of a peptide having a sequence shown in one of SEQ ID No: 17, 18, 25 and 26, or a nucleic acid encoding a peptide having a sequence shown in one of SEQ ID No: 17, 18, 25 and 26, for the manufacture of a chimeric or fusion protein for inducing an immune response to *P. gingivalis*.

In yet another aspect, the invention provides a use of a peptide having a sequence shown in one of SEQ ID No: 17, 18, 25 and 26, or a nucleic acid encoding a peptide having a sequence shown in one of SEQ ID No: 17, 18, 25 and 26, for inducing an immune response to *P. gingivalis*. In one embodiment, the peptide is administered simultaneously or sequentially with a second peptide including:

(i) part of, or all of a sequence that is the same as, or homologous to the sequence of an adhesin domain of the Lys-X-proteinase of *P. gingivalis*; or (ii) part of, or all of a sequence that is the same as, or homologous to the sequence of an adhesin domain of the Arg-X-proteinase of *P. gingivalis*; or (iii) part of, or all of a sequence that is the same as, or homologous to the sequence of a HagA adhesin domain of *P. gingivalis*.

TABLE 3

| SEQ ID NO: | Amino acid sequence | Fragment |
|---|---|---|
| 1 | LNTGV[G/S]FANYTAHGSET[S/A]WADP[S/L][L/V]T[A/T][T/S]Q[V/L]KALTNK[D/N]K | Kgp[432-468] |
| 2 | FNGGISL[V/A]NYTGHGSETAWGTSHFGTTHVKQLTNSNQ | RgpA[426-462] |
| 3 | VSFANYT | |
| 4 | VGFANYT | |
| 5 | GVSFANYT | |
| 6 | GVGFANYT | |
| 7 | VSFANYTA | |
| 8 | VGFANYTA | |
| 9 | ETAWAD | |
| 10 | ETSWAD | |
| 11 | TAWADP | |
| 12 | TSWADP | |
| 13 | SETAWAD | |
| 14 | SETSWAD | |
| 15 | ETAWADP | |
| 16 | ETSWADP | |
| 17 | TAWADPL | |
| 18 | TSWADPL | |
| 19 | GSETAWAD | |
| 20 | GSETSWAD | |
| 21 | SETAWADP | |
| 22 | SETSWADP | |
| 23 | ETAWADPL | |
| 24 | ETSWADPL | |

TABLE 3-continued

| | | |
|---|---|---|
| 25 | TAWADPLL | |
| 26 | TSWADPLL | |
| 27 | LNTGV[G/S]FANYTAHGSET[S/A]WADP[S/L] | KAS1 |
| 28 | NTGV[G/S]FANYTAHGSET[S/A]WADP[S/L][L/V]T[A/T][T/S]Q[V/L]KALTNK[D/N]K | KAS2 |
| 29 | V[G/S]FANYTAHGSET[S/A]WADP[S/L][L/V] | KAS3 |
| 30 | LNTGVSFANYTAHGSETAWADP | PAS1K |
| 31 | FNGGISL[V/A]NYTGHGSETAWGTSH | RAS 1 |
| 32 | NGGISL[V/A]NYTGHGSETAWGTSHFGTTHVKQLTNSNQ | RAS2 |
| 33 | ISL[V/A]NYTGHGSETAWGTSHF | RAS3 |
| 34 | FNGGISLANYTGHGSETAWGT | PAS1R |
| 35 | ANEAKVVLAADNVWGDNTGYQFLLDADHNTFGSVIPATGPLFTGTASSNLYSANFEYLIPANADPVVTTQNIIVTGQGEVVIPGGVYDYCITNPEPASGKMWIAGDGGNQPARYDDFTFEAGKKYTFTMRRAGMGDGTDMEVEDDSPASYTYTVYRDGTKIKEGLTATTFEEDGVAAGNHEYCVEVKYTAGVSPKVCKDVTVEGSNEFAPVQNLTGSSVGQKVTLKWDAPNGTPNPNPNPNPNPGTTLSESFENGIPASWKTIDADGDGHGWKPGNAPGIAGYNSNGCVYSESFGLGGIGVLTPDNYLITPALDLPNGGKLIFWVCAQDANYASEHYAVYASSTGNDASNFTNALLEETITA | KA1 |
| 36 | FLLDADHNTFGSVIPATGPLFTGTASSNLYSANFEYLIPANADPVVITQNIIVTGQGEVVIPGGVYDYCITNPEPASGKMWIAGDGGNQPARYDDFTFEAGKKYTFTMRRAGMGDGTDMEVEDDSPASYTYTVYRDGTKIKEGLTATTFEEDGVAAGNHEYCVEVKYTAGVSPKVCKDVTVEGSNEFAPVQNLTGSSVGQKVTLKWDAPNGTPNPNPNPNPNPGTTLSESF | KsA1 |
| 37 | WGDNTGYQFLLDADHNTFGSVIPATGPLFTGTASSNLYSANFEYLIPANADPVVTTQNIIVTGQGEVVIPGGVYDYCITNPEPASGKMWIAGDGGNQPARYDDFTFEAGKKYTFTMRRAGMGDGTDMEVEDDSPASYTYTVYRDGTKIKEGLTATTFEEDGVAAGNHEYCVEVKYTAGVSPKVCKDVTVEGSNEFAPVQNLTGSSVGQKVTLKVVDAPNGTPNPNPNPNPNPGTTLSESFENGIPASWKTIDADGDGHGWKPGNAPGIAGYNSNGCVYSESFGLGGIGVLTPDNYLITPALDLPNGG | KLA1 |
| 38 | SGQAEIVLEAHDVVVNDGSGYQILLDADHDQYGQVIPSDTHTLWPNCSVPANLFAPFEYTVPENADPSCSPTNMIMDGTASVNIPAGTYDFAIAAPQANAKIWIAGQGPTKEDDYVFEAGKKYHFLMKKMGSGDGTELTISEGGGSDYTYTVYRDGTKIKEGLTATTFEEDGVATGNHEYCVEVKYTAGVSPKVCKDVTVEGSNEFAPVQNLTGSAVGQKVTLKWDAPNGTPNPNPNPNPNPGTTTLSESFENGIPASWKTIDADGDGHGWKPGNAPGIAGYNSNGCVYSESFGLGGIGVLTPDNYLITPALDLPNGGKLTFVVVCAQDANYASEHYAVYASSTGNDASNFTNALLEETITA | RA1 |
| 39 | DDYVFEAGKKYHFLMKKMGSGDGTELTISEGGGSDYTYTVYRDGTKIKEGLTATTFEEDGVATGNHEYCVEVKYTAGVSPKVCKDVTVEGSNEFAPVQNLTGSAVGQKVTLKWDAPNGTPNPNPNPNPNPGTTTLSESF | RsA1 |
| 40 | ADFTETFESSTHGEAPAEWTTIDADGDGQGWLCLSSGQLDWLTAHGGSNVVSSFSWNGMALNPDNYLISKDVTGATKVKYYYAVNDGFPGDHYAVMISKTGTNAGDFTVVFEETPNGIN | KA2 |
| 41 | PQSVWIERTVDLPAGTKYVAFRHYNCSDLNYILLDDIQFTMGGSPTPTDYTYTVYRDGTKIKEGLTETTFEEDGVATGNHEYCVEVKYTAGVSPKKCVNVTVNSTQFNPVQNLTAEQAPNSMDAILKWNAPAS | KA3 |
| 42 | AEVLNEDFENGIPASWKTIDADGDGNNWTTTPPPGGSSFAGHNSAICVSSASYINFEGPQNPDNYLVTPELSLPGGGTLTFWVCAQDANYASEHYAVYASSTGNDASNFANALLEEVLTA | KA4 |

TABLE 3-continued

| 43 | TVVTAPEAIRGTRAQGTWYQKTVQLPAGTKYVAFRHFGC TDFFWINLDDVVITSGNAPSYTYTIYRNNTQIASGVTETTY RDPDLATGFYTYGVKVVYPNGESAIETATLNITSLADVTA QKPYTLTVVGKTITVICQGEAMIYDMNGRRLAAGRNTAVV YTAQGGHYAVMVVVDGKSYVEKLAVK | KA5 |
| --- | --- | --- |
| 44 | ADFTETFESSTHGEAPAEWTTIDADGDGQGWLCLSSGQ LDWLTAHGGTNVVSSFSWNGMALNPDNYLISKDVTGAT KVKYYYAVNDGFPGDHYAVMISKTGTNAGDFTVVFEETP NGIN | RA2 |
| 45 | PQSVWIERTVDLPAGTKYVAFRHYNCSDLNYILLDDIQFT MGGSPTPTDYTYTVYRDGTKIKEGLTETTFEEDGVATGN HEYCVEVKYTAGVSPKKCVNVTVNSTQFNPVKNLKAQP DGGDVVLKWEAPSA | RA3 |
| 46 | ANEAKVVLAADNVWGDNTGYQFLLDADHNTFGSVIPATG PLFTGTASSDLYSANFESLIPANADPVVTTQNIIVTGQGEV VIPGGVYDYCITNPEPASGKMWIAGDGGNQPARYDDFTF EAGKKYTFTMRRAGMGDGTDMEVEDDSPASYTYTVYRD GTKIKEGLTETTYRDAGMSAQSHEYCVEVKYTAGVSPKV CVDYIPDGVADVTAQKPYTLTVVGKTITVTCQGEAMIYDM NGRRLAAGRNTVVYTAQGGYYAVMVVVDGKSYVEKLAI K | RA4 |

| SEQ ID NO: | Nucleotide sequence | |
| --- | --- | --- |
| 47 | GACCATGGCTCATCACCATCACCATCACAATACCGG AGTCAGCTTTGCA | KAS2-FOR |
| 48 | GACTCGAGTTATTTGTCCTTATTAGTGAGTGCTTTC | KAS2-REV |
| 49 | GACCATGGCTTGGGGAGACAATACGGGTTAC | KLA1-FOR |
| 50 | GACTCGAGACCTCCGTTAGGCAAATCC | KLA1-REV |
| 51 | CCGTATTGTCTCCCCATTTGTCCTTATTAGTGAGTGC TTTC | KAS2-KLA1-REV |
| 52 | CACTAATAAGGACAAATGGGGAGACAATACGGGTTA C | KAS2-KLA1-FOR |
| 53 | CATGGATCTGAGACCGCATGGGCTGATCCACTTTTC TTGTTGGATGCCGAT | KAS1-KsA1-FOR1 |
| 54 | CCATGGCTTTGAATACCGGAGTCAGCTTTGCAAACT ATACAGCGCATGGATCTGAGACCGCA | KAS1-KsA1-FOR2 |
| 55 | CTCGAGGAATGATTCGGAAAGTGTT | KAS1-KsA1-REV |
| 56 | CCATGGCTGATTATAGCTGGAATTCCCAGGTAGTCA GCTTTGCAAACTATACA | multi-FOR1 |
| 57 | CTTTGCAAACTATACAGCGCATGGATCTGAGACCGC ATGGGCTGATCCACTT | multi-FOR2 |
| 58 | ATGGGCTGATCCACTTCTGAATTCTTATTGGGGCGA GATCGGCAATATTACC | multi-FOR3 |
| 59 | GATCGGCAATATTACCCATATTGGTGCTCATTACGC TTGGGGAGACAATACG | multi-FOR4 |

TABLE 3-continued

| | | |
|---|---|---|
| 60 | CTCGAGACCTCCGTTAGGCAAATCCAATGCCGGTGT TATCAGATAGTTGTCA | multi-REV |

| SEQ ID NO: | Amino acid sequence | Full length |
|---|---|---|
| 61 | MKNLNKFVSIALCSSLLGGMAFAQQTELGRNPNVRLLES TQQSVTKVQFRMDNLKFTEVQTPKGIGQVPTYTEGVNL SEKGMPTLPILSRSLAVSDTREMKVEVVSSKFIEKKNVLI APSKGMIMRNEDPKKIPYVYGKTYSQNKFFPGEIATLDD PFILRDVRGQVVNFAPLQYNPVTKTLRIYTEITVAVSETSE QGKNILNKKGTFAGFEDTYKRMFMNYEPGRYTPVEEKQ NGRMIVIVAKKYEGDIKDFVDWKNQRGLRTEVKVAEDIA SPVTANAIQQFVKQEYEKEGNDLTYVLLIGDHKDIPAKITP GIKSDQVYGQIVGNDHYNEVFIGRFSCESKEDLKTQIDRT IHYERNITTEDKWLGQALCIASAEGGPSADNGESDIQHE NVIANLLTQYGYTKIIKCYDPGVTPKNIIDAFNGGISLANYT GHGSETAWGTSHFGTTHVKQLTNSNQLPFIFDVACVNG DFLFSMPCFAEALMRAQKDGKPTGTVAIIASTINQSWAS PMRGQDEMNEILCEKHPNNIKRTFGGVTMNGMFAMVEK YKKDGEKMLDTWTVFGDPSLLVRTLVPTKMQVTAPAQI NLTDASVNVSCDYNGAIATISANGKMFGSAVVENGTATI NLTGLTNESTLTLTVVGYNKETVIKTINTNGEPNPYQPVS NLTATTQGQKVTLKWDAPSTKTNATTNTARSVDGIRELV LLSVSDAPELLRSGQAEIVLEAHDVWNDGSGYQILLDAD HDQYGQVIPSDTHTLWPNCSVPANLFAPFEYTVPENAD PSCSPTNMIMDGTASVNIPAGTYDFAIAAPQANAKIWIAG QGPTKEDDYVFEAGKKYHFLMKKMGSGDGTELTISEGG GSDYTYTVYRDGTKIKEGLTATTFEEDGVATGNHEYCVE VKYTAGVSPKVCKDVTVEGSNEFAPVQNLTGSAVGQKV TLKWDAPNGTPNPNPNPNPNPGTTTLSESFENGIPA SWKTIDADGDGHGWKPGNAPGIAGYNSNGCVYSESFG LGGIGVLTPDNYLITPALDLPNGGKLTFWVCAQDANYAS EHYAVYASSIGNDASNFTNALLEETITAKGVRSPEAMRG RIQGTWRQKTVDLPAGTKYVAFRHFQSTDMFYIDLDEVE IKANGKRADFTETFESSTHGEAPAEWTTIDADGDGQGW LCLSSGQLDWLTAHGGTNVVSSFSWNGMALNPDNYLIS KDVTGATKVKYYYAVNDGFPGDHYAVMISKTGTNAGDF TVVFEETPNGINKGGARFGLSTEADGAKPQSVWIERTVD LPAGTKYVAFRHYNCSDLNYILLDDIQFTMGGSPTPTDY TYTVYRDGTKIKEGLTETTFEEDGVATGNHEYCVEVKYT AGVSPKKCVNVTVNSTQFNPVKNLKAQPDGGDVVLKW EAPSAKKTEGSREVKRIGDGLFVTIEPANDVRANEAKVV LAADNVWGDNTGYQFLLDADHNTFGSVIPATGPLFTGTA SSDLYSANFESLIPANADPVVTTQNIIVTGQGEVVIPGGV YDYCITNPEPASGKMWIAGDGGNQPARYDDFTFEAGKK YTFTMRRAGMGDTDMEVEDDSPASYTYTVYRDGTKIK EGLTETTYRDAGMSAQSHEYCVEVKYTAGVSPKVCVDY IPDGVADVTAQKPYTLIVVGKTITVICQGEAMIYDMNGR RLAAGRNTVVYTAQGGYYAVMVVVDGKSYVEKLAIK | RgpA |
| 62 | MRKLLLLIAASLLGVGLYAQSAKIKLDAPTTRTTCTNNSF KQFDASFSFNEVELTKVETKGGTFASVSIPGAFPTGEVG SPEVPAVRKLIAVPVGATPWRVKSFTEQVYSLNQYGSE KLMPHQPSMSKSDDPEKVPFVYNAAAYARKGFVGQELT QVEMLGTMRGVRIAALTINPVQYDVVANQLKVRNNIEIEV SFQGADEVATQRLYDASFSPYFETAYKQLFNRDVYTDH GDLYNTPVRMLVVAGAKFKEALKPWLTWKAQKGFYLDV HYTDEAEVGTTNASIKAFIHKKYNDGLAASAAPVFLALVG DTDVISGEKGKKTKKVTDLYYSAVDGDYFPEMYTFRMS ASSPEELTNIIDKVLMYEKATMPDKSYLEKVLLIAGADYS WNSQVGQPTIKYGMQYYYNQEHGYTDVYNYLKAPYTG CYSHLNTGVSFANYTAHGSETAWADPLLTTSQLKALTNK DKYFLAIGNCCITAQFDYVQPCFGEVITRVKEKGAYAYIG SSPNSYWGEDYYVVSVGANAVFGVQPTFEGTSMGSYDA TFLEDSYNTVNSIMWAGNLAATHAGNIGNITHIGAHYYW EAYHVLGDGSVMPYRAMPKTNTYTLPASLPQNQASYSI QASAGSYVAISKDGVLYGTGVANASGVATVSMTKQITEN GNYDVVITRSNYLPVIKQIQVGEPSPYQPVSNLTATTQG QKVTLKWEAPSAKKAEGSREVKRIGDGLFVTIEPANDVR ANEAKVVLAADNVVVGDNTGYQFLLDADHNTFGSVIPAT GPLFTGTASSNLYSANFEYLIPANADPVVTTQNIIVTGQG EVVIPGGVYDYCITNPEPASGKMWIAGDGGNQPARYDD FTFEAGKKYTFTMRRAGMGDTDMEVEDDSPASYTYTV YRDGTKIKEGLTATTFEEDGVAAGNHEYCVEVKYTAGVS PKVCKDVTVEGSNEFAPVQNLTGSSVGQKVTLKWDAPN GTPNPNPNPNPNPGTTTLSESFENGIPASWKTIDADGDG HGWKPGNAPGIAGYNSNGCVYSESFGLGGIGVLTPDNY | Kgp |

TABLE 3-continued

| | | |
|---|---|---|
| | LITPALDLPNGGKLTFWVCAQDANYASEHYAVYASSTGN | |
| | DASNFTNALLEETITAKGVRSPKAIRGRIQGTWRQKTVDL | |
| | PAGTKYVAFRHFQSTDMFYIDLDEVEIKANGKRADFTET | |
| | FESSTHGEAPAEWTTIDADGDGQGWLCLSSGQLDWLT | |
| | AHGGSNVVSSFSWNGMALNPDNYLISKDVTGATKVKYY | |
| | YAVNDGFPGDHYAVMISKTGTNAGDFTVVFEETPNGINK | |
| | GGARFGLSTEANGAKPQSVWIERTVDLPAGTKYVAFRH | |
| | YNCSDLNYILLDDIQFTMGGSPTPTDYTYTVYRDGTKIKE | |
| | GLTETTFEEDGVATGNHEYCVEVKYTAGVSPKKCVNVT | |
| | VNSTQFNPVQNLTAEQAPNSMDAILKWNAPASKRAEVL | |
| | NEDFENGIPASWKTIDADGDGNNWTTTPPPGGSSFAGH | |
| | NSAICVSSASYINFEGPQNPDNYLVTPELSLPGGGTLTF | |
| | WVCAQDANYASEHYAVYASSTGNDASNFANALLEEVLT | |
| | AKTVVTAPEAIRGTRAQGTVVYQKTVQLPAGTKYVAFRH | |
| | FGCTDFFWINLDDWITSGNAPSYTYTIYRNNTQIASGVT | |
| | ETTYRDPDLATGFYTYGVKVVYPNGESAIETATLNITSLA | |
| | DVTAQKPYTLTVVGKTITVTCQGEAMIYDMNGRRLAAGR | |
| | NTVVYTAQGGHYAVMVVVDGKSYVEKLAVK | |
| 63 | MRKLNSLFSLAVLLSLLCWGQTAAAQGGPKTAPSVTHQ | HagA |
| | AVQKGIRTSKAKDLRDPIPAGMARIILEAHDVVVEDGTGY | |
| | QMLWDADHNQYGASIPEESFWFANGTIPAGLYDPFEYK | |
| | VPVNADASFSPTNFVLDGTASADIPAGTYDYVIINPNPGII | |
| | YIVGEGVSKGNDYVVEAGKTYHFTVQRQGPGDAASVVV | |
| | TGEGGNEFAPVQNLQWSVSGQTVTLTWQAPASDKRTY | |
| | VLNESFDTQTLPNGVVTMIDADGDGHNWLSTINVYNTAT | |
| | HTGDGAMFSKSVVTASSGAKIDLSPDNYLVTPKFTVPEN | |
| | GKLSYWVSSQEPWTNEHYGVFLSTTGNEAANFTIKLLEE | |
| | TLGSGKPAPMNLVKSEGVKAPAPYQERTIDLSAYAGQQ | |
| | VYLAFRHFGCTGIFRLYLDDVAVSGEGSSNDYTYTVYRD | |
| | NVVIAQNLTATTFNQENVAPGQYNYCVEVKYTAGVSPKV | |
| | CKDVTVEGSNEFAPVQNLTGSAVGQKVTLKWDAPNGTP | |
| | NPNPGTTTLSESFENGIPASWKTIDADGDGNNWTTTPPP | |
| | GGSSFAGHNSAICVSSASYINFEGPQNPDNYLVTPELSL | |
| | PNGGTLTFWVCAQDANYASEHYAVYASSTGNDASNFA | |
| | NALLEEVLTAKTVVTAPEAIRGTRVQGTWYQKTVQLPAG | |
| | TKYVAFRHFGCTDFFWINLDDVEIKANGKRADFTETFES | |
| | STHGEAPAEWTTIDADGDGQGWLCLSSGQLGWLTAHG | |
| | GTNVVASFSWNGMALNPDNYLISKDVTGATKVKYYYAV | |
| | NDGFPGDHYAVMISKTGTNAGDFTVVFEETPNGINKGG | |
| | ARFGLSTEANGAKPQSVWIERTVDLPAGTKYVAFRHYN | |
| | CSDLNYILLDDIQFTMGGSPTPTDYTYTVYRDGTKIKEGL | |
| | TETTFEEDGVATGNHEYCVEVKYTAGVSPKECVNVTVD | |
| | PVQFNPVQNLTGSAVGQKVTLKWDAPNGTPNPNPGTTT | |
| | LSESFENGIPASWKTIDADGDGNNWITTPPPGGTSFAG | |
| | HNSAICVSSASYINFEGPQNPDNYLVTPELSLPNGGTLTF | |
| | WVCAQDANYASEHYAVYASSTGNDASNFANALLEEVLT | |
| | AKTVVTAPEAIRGTRVQGTWYQKTVQLPAGTKYVAFRH | |
| | FGCTDFFWINLDDVEIKANGKRADFTETFESSTHGEAPA | |
| | EWTTIDADGDGQGWLCLSSGQLDWLTAHGGTNVVASF | |
| | SWNGMALNPDNYLISKDVTGATKVKYYYAVNDGFPGDH | |
| | YAVMISKTGTNAGDFTVVFEETPNGINKGGARFGLSTEA | |
| | NGAKPQSVVIERTVDLPAGTKYVAFRHYNCSDLNYILLD | |
| | DIQFTMGGSPTPTDYTYTVYRDGTKIKEGLTETTFEEDG | |
| | VATGNHEYCVEVKYTAGVSPKECVNVTVDPVQFNPVQN | |
| | LTGSAVGQKVTLKWDAPNGTPNPNPGTTTLSESFENGIP | |
| | ASWKTIDADGDGNNVVTTTPPPGGTSFAGHNSAICVSSA | |
| | SYINFEGPQNPDNYLVTPELSLPNGGTLTFWVCAQDAN | |
| | YASEHYAVYASSTGNDASNFANALLEEVLTAKTVVTAPE | |
| | AIRGTRVQGTWYQKTVQLPAGTKYVAFRHFGCTDFFWI | |
| | NLDDVEIKANGKRADFTETFESSTHGEAPAEWTTIDADG | |
| | DGQGWLCLSSGQLGWLTAHGGTNVVASFSWNGMALN | |
| | PDNYLISKDVTGATKVKYYYAVNDGFPGDHYAVMISKTG | |
| | TNAGDFTVVFEETPNGINKGGARFGLSTEANGAKPQSV | |
| | WIERTVDLPAGTKYVAFRHYNCSDLNYILLDDIQFTMGG | |
| | SPTPTDYTYTVYRDGTKIKEGLTETTFEEDGVATGNHEY | |
| | CVEVKYTAGVSPKECVNVTINPTQFNPVQNLTAEQAPNS | |
| | MDAILKWNAPASKRAEVLNEDFENGIPASWKTIDADGDG | |
| | NNWTTTPPPGGSSFAGHNSAICVSSASYINFEGPQNPD | |
| | NYLVTPELSLPGGGTLTFWVCAQDANYASEHYAVYASS | |
| | TGNDASNFANALLEEVLTAKTVVTAPEAIRGTRVQGTWY | |
| | QKTVQLPAGTKYVAFRHFGCTDFFWINLDDVVITSGNAP | |
| | SYTYTIYRNNTQIASGVTETTYRDPDLATGFYTYGVKVVY | |
| | PNGESAIETATLNITSLADVTAQKPYTLTWGKTITVTCQG | |
| | EAMIYDMNGRRLAAGRNTVVYTAQGGHYAVMVVVDGK | |
| | SYVEKLAVK | |

TABLE 3-continued

| SEQ ID NO: | Amino acid sequence | Fragment |
|---|---|---|
| 64 | D[S/Y][Y/S]WN[P/S][K/Q][I/V] | KAS4 |
| 65 | NSYWGED | KAS5 |
| 66 | IGN[V/I]THIGAHY | KAS6 |
| 67 | EGGPSADN | RAS4 |
| 68 | [N/D]Q[S/Y]WA[S/P]P | RAS5 |
| 69 | PVSNLTATTQGQKVTLKWDAPST | ABM1-RgpA$_{cat}$ |
| 70 | PVSNLTATTQGQKVTLKWEAPSA | ABM1-Kgpcat |
| 71 | PVQNLIGSSVGQKVTLKWDAPST | ABM1-KgpA1 |
| 72 | PVQNLTGSAVGQKVTLKWDAPNG | ABM1-RgpA1 & RgpAA3 |
| 73 | PVKNLKAQPDGGDVVLKWEAPSA | ABM1-HagAA1*/** |
| 74 | PVQNLTAEQAPNSMDAILKWNAP | ABM1-KgpA3 & HagAA3 |
| 75 | PVQNLTQWSVSGQTVTLTWQAPAS | ABM2-HagAA1 |
| 76 | YTYTVYRDGTKIKEGLTETTFEEDGVA | ABM2-ABM2-RgpAA4 |
| 77 | YTYTVYRDNVVIAQNLTATTFNQENVA | ABM2-HagA1* |
| 78 | YTYTVYRDGTKIKEGLTA/ETTFEEDGVA | ABM2 All other adhesins |
| 79 | PNGTP(NP)$_{1-6}$GTT(T)LSESF | ABM3- All adhesins |
| 80 | GGPKTAPSVTHQAVQKGIRTSKAKDLRDPIPAGMARIILE AHDVVVEDGTGYQMLWDADHNQYGASIPEESFVVFANGTI PAGLYDPFEYKVPVNADASFSPTNFVLDGTASADIPAGTY DYVIINPNPG1IYIVGEGVSKGNDYVVEAGKTYHFTVQRQ GPGDAASVVVTGEGGNEFAPVQNLQWSVSGQTVTLTVV QAPASDKRTYVLNESFDTQTLPNGWTMIDADGDGHNWL STINVYNTATHTGDGAMFSKSWTASSGAKIDLSPDNYLVT PKFTVPENGKLSYWVSSQEFAWNEHYGVFLSTTGNEAA NFTIKLLEETLGSG | HagA1 [26-351] |
| 81 | APAPYQERTIDLSAYAGQQVYLAFRHFGCTGIFRLYLDDV AVSGEGSSNDYTYTVYRDNWIAQNLTATTFNQENVAPG QYNYCVEVKYTAGVSPKVCKDVTVEGSNEFAPVQNLTG SAVGQKVTLKWDAPNGTPNPNPGTTTLSESFENGIPASW KTIDADGDGNNWTTTPPPGGSSFAGHNSAICVSSASYIN FEGPQNPDNYLVTPELSLPNGGTLTF1NVCAQDANYASE HYAVYASSTGNDASNFANALLEEVLTA | HagA1* [366-625] |
| 82 | PQSVWIERTVDLPAGTKYVAFRHYNCSDLNYILLDDIQFT MGGSPTPTDYTYTVYRDGTKIKEGLTETTFEEDGVATGN HEYCVEVKYTAGVSPKECVNVTVDPVQFNPVQNLTGSA VGQKVTLKWDAPNGTPNPNPGTTTLSESFENGIPASWKT IDADGDGNNWTTTPPPGGTSFAGHNSAICVSSASYINFE GPQNPDNYLVTPELSLPNGGTLTFWVCAQDANYASEHY AVYASSTGNDASNFANALLEEVLTA | HagA1** [820-1077] or HagA1** [1272-1529] |

TABLE 3-continued

| 83 | PYQPVSNLTATTQGQ | ABM1[436-450] |
| 84 | EGLTATTFEEDGVAA | ABM2[672-686] |
| 85 | GTPNPNPNPNPNPNPGT | ABM3[455-471] |

The invention is further illustrated by the following Examples which are included by way of exemplification and not limitation of the invention.

Example 1

Methods and Materials

Bacterial strains and growth conditions. Lyophilised cultures of *Porphyromonas gingivalis* W50 were grown anaerobically at 37° C. on lysed horse blood agar plates supplemented with 5 µg/ml haemin, 0.5 µg/ml cysteine (HB agar, <10 passages). After 3-4 days colonies were used to inoculate brain heart infusion medium containing 5 µg/ml haemin, 0.5 µg/ml cysteine (1). Batch cultures were grown anaerobically in a MK3 Anaerobic Workstation (Don Whitley Scientific Ltd., Adelaide, Australia). Cells were harvested during exponential growth phase by centrifugation (7500 g, 30 min, 4° C.) and washed twice with PG buffer (50 mM Tris-HCl, 150 mM NaCl, 5 mM $CaCl_2$, and 5 mM cysteine-HCl, pH 8.0) in the anaerobic workstation. Growth of batch cultures was monitored at 650 nm using a spectrophotometer (model 295E, Perkin-Elmer). Culture purity was checked routinely by Gram stain, microscopic examination and using a variety of biochemical tests according to Slots (2).

Construction of pET28 constructs containing adhesin sequences and adhesin sequences with N-terminal addition of Kgp proteinase sequences. Kgp residues representing peptides and chimeric peptides of the active site (AS) and KgpA1 adhesin (A1) domains were over-expressed in *E. coli* as recombinant (r) proteins with hexa-His tags using pET expression vectors (Novagen). The r-proteins expressed were rKAS2, and rKLA1 and the r-chimeric proteins were rKAS2-KLA1, rKAS1-KsA1 and rKAS4-KAS3-KAS5-KAS6-KLA1 (also referred to as multiKAS-KLA1). The amino acid sequences representing the various A1 and AS domains are described in Tables 1 and 2.

The various KAS and KA1 domains of the kgp gene were amplified from pNS1 (3.5 kb BamHI lys fragment in pUC18) or *P. gingivalis* genomic DNA respectively using primers listed in Table 4, Taq DNA polymerase (Invitrogen) and a PC-960 thermal cycler (Corbett Research Technologies). Primer pairs KAS2-FOR and KAS2-REV and KLA1-FOR and KLA1-REV were used to generate PCR fragments encoding KAS2 and KLA1 respectively using the following reaction conditions: 94° C., 3 minutes, followed by 28 cycles of 94° C., 45 sec (denaturing); 62° C., 40 seconds (annealing) and 72° C., 20 seconds (extension) followed by a final cycle of 72° C., 5 min.

The KAS2-KLA1 chimeric PCR product was produced by gene splicing by overlap extension (SOEing) as follows: PCR products were produced using primer pairs KAS2-FOR and KAS2-KLA1-chimera-REV and KAS2-KLA1-chimera-FOR and KLA1-REV using the conditions described above. The PCR products were then annealed and a final PCR was performed with primers KAS2-FOR and KLA1-REV (94° C., 2 minutes, followed by 28 cycles of 94° C., 30 sec; 50° C., 30 seconds and 72° C., 40 seconds followed by a final cycle of 72° C., 5 min.

For the preparation of the KAS1-KsA1 PCR product, two successive PCR's were conducted using the KAS1-KsA1-REV primer with each of the KAS1-KsA1-FOR primers 1 and, 2 in succession (reaction conditions 94° C. for 2 minutes followed by 35 cycles of 94° C., 15 seconds; 63° C., 30 seconds and 72° C., 2 minutes) to produce the KAS1-KsA1 PCR product. The KAS1-KsA1-FOR1 and KAS1-KsA1-FOR2 primers contain an 3' extension overlapping the 5' of the previous PCR product.

For the preparation of the multiKAS-KLA1 PCR fragment, four successive PCR's were conducted using the multi-REV primer with each of the multi-FOR primers 1, 2, 3 and 4 in succession (reaction conditions were 95° C., 2 minutes followed by 35 cycles of 95° C., 20 seconds; 68° C., 1.5 minutes) to produce the multiKAS-KLA1 PCR product. Each multi-FOR primer contains a 3' extension overlapping the 5' of the previous PCR product.

All of the PCR fragments encoding KAS2, KLA1, KAS2-KLA1, KAS1-KsA1 and multiKAS-KLA1. were purified using PCR purification columns (Qiagen), ligated into the TA cloning vector, pGem®-T Easy (Promega) and transformed into *E. coli* JM109 following the manufacturer's protocol. Purified recombinant pGem®-T Easy constructs were digested with NcoI and XhoI and directionally cloned into NcoI/XhoI digested pET28b (Novagen) and transformed into the non-expression host, *E. coli* JM109 [DH5a]. The recombinant pET28 constructs were purified and transformed into the *E. coli* expression host, BL21 (DE3) [HMS174(DE3)] (Novagen) and selected on LB containing 50 µg kanamycin following the manufacturer's instructions. The integrity of each insert was confirmed by DNA sequence analysis.

The oligonucleotide primers (Table 4) have been designed to incorporate restriction enzyme sites, stop codons and hexa-His Tags where necessary. The primers used for the rKAS2, rKLA1 and rKAS2-KLA1 were designed to limit the inclusion of extraneous coding sequence to no more than three amino acids plus the hexa-his tag in r-proteins. The rKAS1 and the rKLA1 were designed to contain a hexa-His tag at the N-terminal and C-terminal ends respectively, so that they may be directly compared to the rKAS2-KLA1 which has a hexa-his tag at both N- and C-termini. In rKAS1-KsA1 and rmultiKAS-KLA1 the His Tags are found at the C-termini.

TABLE 4

Oligonucleotide primers used for the amplification of the nucleotide sequences encoding the various fragments and chimeras of Kgp A1 and AS

| Recombinant (r) protein | Oil | Sequence (5'-3') | Characteristics* (5'-3') |
|---|---|---|---|
| rKAS2 | KAS2-FOR | GACCATGGCTCATCACCATCACC ATCACAATACCGGAGTCAGCTTT GCA (SEQ ID NO: 47) | GA buffer-NcoI (including ATG start)-CT-(His)$_6$-AS (nt 1992-2012) |
|  | KAS2-REV | GACTCGAGTTATTTGTCCTTATTA GTGAGTGCTTTC (SEQ ID NO: 48) | GA buffer-XhoI-TTA Stop-KAS1 (nt 2099-2075) |
| rKLA1 | KLA1-FOR | GACCATGGCTTGGGGAGACAATA CGGGTTAC (SEQ ID NO: 49) | GA buffer-NcoI (including ATG start)-CT-A1 (nt 2946-2966) |
|  | KLA1-REV | GACTCGAGACCTCCGTTAGGCAA ATCC (SEQ ID NO: 50) | GA buffer-XhoI-A1 (nt 3863-3845) |
| rKAS2-KLA1 | KAS2-KLA1-REV | CCGTATTGTCTCCCCATTTGTCCT TATTAGTGAGTGCTTTC (SEQ ID NO: 51) | A1 (nt 2961-2946)-KAS1 (nt 2099-2075) |
|  | KAS2-KLA1-FOR | CACTAATAAGGACAAATGGGGAG ACAATACGGGTTAC (SEQ ID NO: 52) | KAS1 (nt 2084-2099)-A1 (nt 2946-2966) |
| rKAS1-KsA1 | KAS1-KsA1-FOR1 | CATGGATCTGAGACCGCATGGG CTGATCCACTTTTCTTGTTGGATG CCGAT (SEQ ID NO: 53) | AS (nt 2025-2057)-A1 (nt 2970-2987)- |
|  | KAS1-KsA1-FOR2 | CCATGGCTTTGAATACCGGAGTC AGCTTTGCAAACTATACAGCGCA TGGATCTGAGACCGCA SEQ ID NO: 54) | NcoI-CT-AS (nt 1989-2042) |
|  | KAS1-KsA1-REV | CTCGAGGAATGATTCGGAAAGTG TT (SEQ ID NO: 55) | XhoI-A1(nt 3663-3644) |
| rmultiKAS-KLA1 | multi-FOR1 | CCATGGCTGATTATAGCTGGAAT TCCCAGGTAGTCAGCTTTGCAAA CTATACA (SEQ ID NO: 56) | NcoI-CT-KAS4 (nt 1857-1880)-KAS3 (nt 2001-2021) |
|  | multi-FOR2 | CTTTGCAAACTATACAGCGCATG GATCTGAGACCGCATGGGCTGAT CCACTT (SEQ ID NO: 57) | KAS3 (nt 2006-2057) |
|  | multi-FOR3 | ATGGGCTGATCCACTTCTGAATT CTTATTGGGCGAGATCGGCAAT ATTACC (SEQ ID NO: 58) | KAS3 (nt 2042-2060)-KAS5 (nt 2223-2240)-KAS6 (nt 2403-2417) |
|  | multi-FOR4 | GATCGGCAATATTACCCATATTG GTGCTCATTACGCTTGGGGAGAC AATACG (SEQ ID NO: 59) | G-KAS6 (nt 2403-2435)-GCT (Ala spacer)-A1(nt 2946-2960) |
|  | multi-REV | CTCGAGACCTCCGTTAGGCAAAT CCAATGCCGGTGTTATCAGATAG TTGTCA (SEQ ID NO: 60) | Xho-A1 (nt 3863-3818) |

*nucleotide (nt) sequence numbers from lysine-specific cysteine proteinase gene sequence accession number U75366

Expression and purification of recombinant proteins. Recombinant proteins were expressed from pET28::KLA1 (KAS2, KAS2-LA1, KAS1-SA1, multiKAS-KLA1) constructs by induction with isopropyl β-D-thiogalactosidase (IPTG). All recombinant proteins were produced as 6-His Tag fusion proteins and purified with NI-NTA purification system (Invitrogen) under denaturing conditions. Briefly, E. coli (DE3) single colony transformants were used to inoculate 20 mL of Luria-Bertani (LB) broth containing 50 μg/ml kanamycin at 37° C. on an orbital shaker overnight. This inoculum was then used to inoculate 1 L of LB containing 50 μg/ml kanamycin. The $OD_{600}$ of this culture was allowed to reach 0.5-0.7 (mid-log phase) before inducing protein expression with isopropyl IPTG at 0.1 mM for 2 hours at 37° C. with shaking of 200 rpm. Cells were harvested (7,500 g) and resuspended in a denaturing binding buffer (8M Urea, 20 mM Sodium Phosphate pH 8.0 & 500 mM NaCl) and sonicated on ice for 3×15 s bursts at 30 s intervals using a Branson Sonifer 250 Cell disrupter (Branson Ultronics Corporation, Danbury, Conn.) with the microtip on setting 3, then centrifuged at 39,000 g for 30 min at 4° C. Recombinant proteins were purified from the supernatant by loading onto a pre-equilibrated Ni-NTA Agarose column and then washing with denaturing washing buffer (8M Urea, 20 mM Sodium Phosphate pH 6.0 & 500 mM NaCl) to elute unbound proteins. The column was then washed using 10 volumes of binding buffer B and the recombinant protein was eluted with denaturing elution buffer (8M Urea, 20 mM Sodium Phosphate pH 6.0, 500 mM NaCl & 0.5 M Imidazole). Purified protein was dialyzed against 2M Urea-PBS and stored at −80° C.

Recombinant protein samples were analysed by SDS-PAGE and their molecular masses determined using Prot-Param on-line (au.expasy.org/tools/protparam.html). Protein concentration of all samples was determined by the Bio-Rad Protein Assay using BSA as a standard.

Immunisation and the mouse periodontitis model. The mouse periodontitis experiments were performed as described previously (3) and were approved by the University of Melbourne Ethics Committee for Animal Experimentation. BALB/c mice 6-8 weeks old (12 mice per group) housed in microisolators were immunized subcutaneously (s.c. 100 μL) with either 50 μg of one of the recombinant proteins or RgpA-Kgp complex, $2 \times 10^9$ formalin killed cells of P. gingivalis strain W50 or PBS; each antigen was emulsified in incomplete Freund's adjuvant (IFA). After 30 days the mice were boosted with antigen (s.c. injection, emulsified in IFA) and then bled from the retrobulbar plexus 12 days later. Four days after the second immunisation mice were given kanamycin (Sigma-Aldrich, New South Wales, Australia) at 1 mg/ml in deionized water ad libitum for 7 days. Three days after the antibiotic treatment (2 days after bleeding), mice were orally inoculated four times 2 days apart with $1 \times 10^{10}$ viable P. gingivalis W50 (25 μl) in PG buffer (50 mM Tris-HCl, 150 mM NaCl, 5 mM $CaCl_2$, and 5 mM cysteine-HCl, pH 8.0) containing 2% (wt/vol) carboxymethyl cellulose (CMC; Sigma-Aldrich, New South Wales, Australia), and a control group was sham infected with PG buffer containing 2% (wt/vol) CMC alone. The inocula were prepared in the anaerobic chamber and then immediately applied to the gingival margin of the maxillary molar teeth. Two weeks later, mice received another four doses (2 days apart) of $1 \times 10^{10}$ cells of viable P. gingivalis W50 (25 μl) in PG buffer containing 2% (wt/vol) CMC. The number of viable bacteria in each inoculum was verified by enumeration on blood agar. Mice were fed a soft powdered diet (Barastock, Australia) and housed in cages fitted with a raised wire mesh bottom to prevent access to bedding. Four weeks after the last dose, mice were bled from the retrobulbar plexus and killed, and the maxillae were removed and cut in half with one half (right) used for alveolar bone loss measurement and the other half (left) used for real-time PCR.

The right half maxillae were boiled (1 min) in deionized water, mechanically defleshed, and immersed in 2% (wt/vol) potassium hydroxide (16 h, 25° C.). The half maxillae were then washed (two times with deionized water) and immersed in 3% (wt/vol) hydrogen peroxide (6 h, 25° C.). After the half maxillae were washed (two times with deionized water), they were stained with 0.1% (wt/vol) aqueous methylene blue, and a digital image of the buccal aspect of each half maxilla was captured with an Olympus DP12 digital camera mounted on a dissecting microscope, using OLYSIA BioReport software version 3.2 (Olympus Australia Pty Ltd., New South Wales, Australia) to assess horizontal bone loss. Horizontal bone loss is loss occurring in a horizontal plane, perpendicular to the alveolar bone crest (ABC) that results in a reduction of the crest height. Each half maxilla was aligned so that the molar buccal and lingual cusps of each tooth image were superimposed, and the image was captured with a micrometer scale in frame, so that measurements could be standardized for each image. The area from the cementoenamel junction to the ABC for each molar tooth was measured using OLYSIA BioReport software version 3.2 imaging software. Bone loss measurements were determined twice by a single examiner using a randomized and blinded protocol.

Determination of subclass antibody by an elisa. To determine the subclass antibody responses of mouse sera, enzyme-linked immunosorbent assays (ELISAs) were performed in triplicate using a 5-μg/ml solution of formalin killed P. gingivalis W50 in phosphate-buffered saline (PBS) (0.01 M $Na_2HPO_4$, 1.5 mM $KH_2PO_4$, 0.15 M NaCl), pH 7.0, containing 0.1% (vol/vol) Tween 20 (PBST) to coat wells of flat-bottom polyvinyl microtiter plates (Dynatech Laboratories, McLean, Va.). After removal of the coating solution, PBST containing 2% (wt/vol) skim milk powder was added to wells to block the uncoated plastic for 1 h at room temperature. After the wells were washed four times with PBST, serial dilutions of mouse sera in PBST containing 0.5% (wt/vol) skim milk (SK-PBST) were added to each well and incubated for 16 h at room temperature. After the wells were washed six times with PBST, a 1/2,000 dilution of goat IgG to mouse IgM, IgA, IgG1, IgG2a, IgG2b, or IgG3 (Sigma, New South Wales, Australia) was added in SK-PBST and allowed to bind for 2 h at room temperature. Plates were washed six times in PBST, and a 1/5,000 dilution of horseradish peroxidase-conjugated rabbit anti-goat immunoglobulin (Sigma, New South Wales, Australia) in SK-PBST was added to each well and incubated for 1 h at room temperature. After the wells were washed six times with PBST, bound antibody was detected by the addition of 100 μl of ABTS substrate[0.9 mM 2,2'-azino-bis(3-ethylbenz-thiazoline-6) sulfonic acid in 80 mM citric acid containing 0.005% (vol/vol) hydrogen peroxide, pH 4.0] to each well. The optical density at 415 nm was measured using a microplate reader (Bio-Rad microplate reader, model 450).

SDS-PAGE gel electrophoresis and western blotting. Recombinant proteins (10 μg) were analysed using the XCell surelock Mini-Cell electrophoresis system. Recombinant proteins were mixed in 20 μl of reducing sample buffer (10% [wt/vol] SDS, 0.05% [wt/vol] bromophenol blue, 25% [vol/vol] glycerol, and 0.05% [vol/vol] 2-mercaptoethanol). The pH was adjusted to pH 8.0 with 1.5 M Tris-HCl, and then the solution was heated for 5 min at 100° C. Recombinant proteins (10 μg/lane) were loaded onto Novex 12% (wt/vol) Tris-glycine precast mini gels, and electrophoresis was performed using a current of 30 to 50 mA and a potential difference of 125 V using a Novex electrophoresis system (Novex, San Diego, Calif.). Proteins were visualized using 0.25% w/v Coomassie blue R250.

Epitope analysis of the Kgp proteinase active site peptide (KAS-2) sequence. The antibody binding sites for the Lys-specific proteinase active site peptide KAS2 (433-468 SEQ ID No: 28) was determined by synthesising N-terminally biotinylated overlapping eight residue peptides (offset by one, overlapping by seven residues) on a multipin peptide synthesis system (Chiron Technologies, Melbourne, Australia) using standard solid-phase peptide synthesis protocols for Fmoc chemistry. Biotinylated peptides (5 μg/mL) in 0.1 M PBS, pH 7.4 were bound to strepavidin coated plates, overnight at 4° C. (Nunc, NSW Australia). After the wells were washed four times with PBST epitope mapping of the plate-bound peptides was carried out by ELISA as per Chiron Technologies instructions using mouse sera at a dilution of 1:1000 in 1% w/v non-fat skim milk powder in 0.1 M PBS, pH 7.4, containing 0.1% v/v Tween 20 (SK-PBST). After the wells were washed six times with PBST, a 1/2,000 dilution of goat IgG to mouse IgG (Sigma, New South Wales, Australia) was added in SK-PBST and allowed to bind for 2 h at room temperature. Plates were washed six times in PBST, and a 1/5,000 dilution of horseradish peroxidase-conjugated rabbit anti-goat immunoglobulin (Sigma, New South Wales, Australia) in SK-PBST was added to each well and incubated for 1 h at room temperature. After the wells were washed six times with PBST, bound antibody was detected by the addition of 100 μl of ABTS substrate[0.9 mM 2,2'-azino-bis(3-ethylbenz-thiazoline-6) sulfonic acid in 80 mM citric acid containing 0.005% (vol/vol) hydrogen peroxide, pH 4.0] to each well. The optical density at 415 nm was measured using a microplate reader (Bio-Rad microplate reader, model 450).

Statistical analysis. The bone loss data were statistically analyzed using a one-way analysis of variance (ANOVA) and Dunnett's T3 test (SPSS for Windows, version 12). The IgA, IgM, and IgG subclass antibody titers were statistically analyzed using Student's t test using SPSS software (SPSS for Windows, version 12).

Example 2

Figure 2:
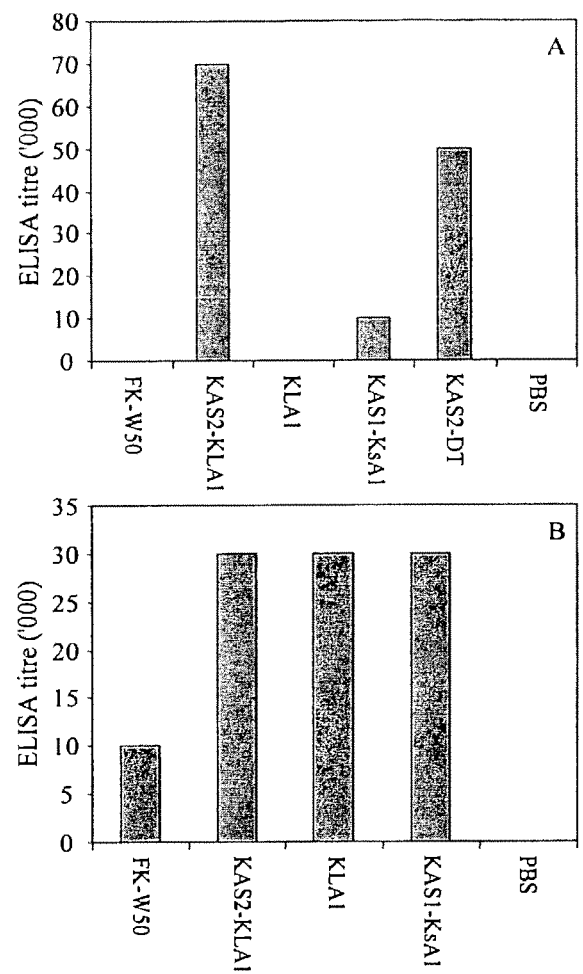
FIG. 2 shows antibody recognition of KAS2 peptide and formalin killed *P. gingivalis* W50 cells. (A) KAS2 peptide was probed with antisera raised to formalin killed *P. gingivalis* W50 cells (FK-W50), recombinant proteins KAS1-KsA1, KAS2-KLA1, and synthetic KAS2-DT conjugate and PBS in an ELISA. (B) formalin killed *P. gingivalis* W50 cells were probed with antisera raised to formalin killed *P. gingivalis* W50 cells (FK-W50), recombinant proteins KAS1-KsA1, KAS2-KLA1, KLA1 and PBS in an ELISA. Antibody responses are expressed as the ELISA titre $OD_{415}$ obtained minus double the background level, with each titre representing the mean±standard deviation of three values.

Characterisation and purification of the recombinant proteins (KsA1, KLA1, KAS1-KsA1 and KAS2-KLA1). In order to characterise the ability of Kgp adhesin A1 domain fragments and chimera Kgp proteinase and Kgp adhesin A1 domain fragments to protect against P. gingivalis infection, we expressed and purified the recombinant proteins:-KsA1, KLA1, KAS1-KsA1 and KAS2-KLA1. Recombinant proteins (KsA1 and KLA1) and recombinant chimera proteins (KAS1-KsA1 and KAS2-KLA1) were purified from inclusion bodies using nickel chelate affinity chromatography and the purified proteins analysed by SDS-PAGE (FIG. 1). Each of the purified recombinant proteins consisted of one major protein band with molecular weights of 40, 36, 31 and 32 kDa corresponding to KAS2-KLA1, KLA1, KsA1 and KAS1-KsA1, and these weights corresponded to the calculated molecular masses of the His-tag recombinant proteins using ProtParam. To characterize the immunogenicity of the recombinant proteins KsA1, KLA1, KAS1-KsA1 and KAS2-KLA1 were used to immunize mice and the sera was used to probe KAS2 peptide coated plates and formalin killed P. gingivalis W50 cells coated plates (FIG. 2). Recombinant chimera proteins KAS1-KsA1 and KAS2-KLA1 antisera were found to recognize KAS2 peptide (FIG. 2A) at a similar level to KAS2 specific antisera (KAS2-diptheria toxoid conjugate) as well as formalin killed P. gingivalis W50 cells (FIG. 2B). However, antisera against the recombinant protein KLA1 only recognized killed P. gingivalis W50 cells (FIG. 2B).

Example 3

Figure 3:
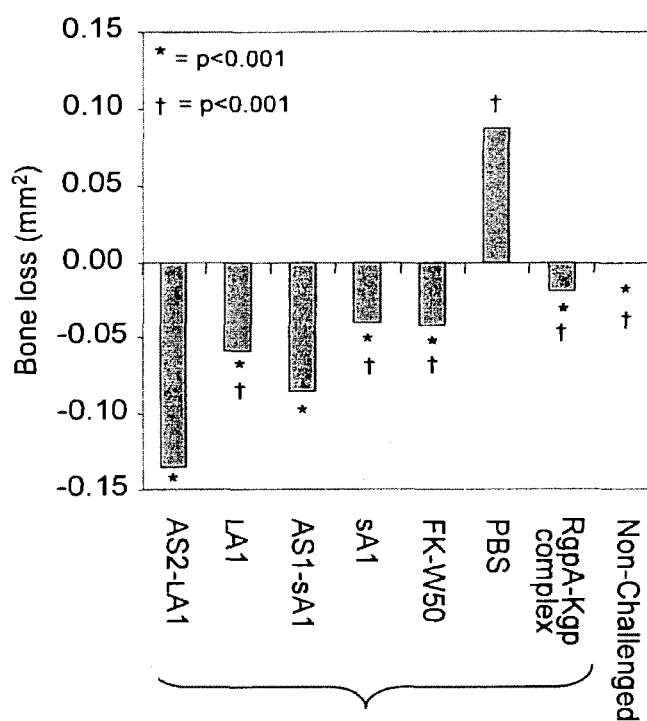
FIG. 3 shows *P. gingivalis*-induced horizontal bone loss of maxillae molars of mice immunised with the recombinant proteins and recombinant chimera proteins, formalin-killed *P. gingivalis* and adjuvant alone (PBS, FA) or non-orally infected (non-challenged) mice. In this figure KAS2-KLA1 is shown as AS2-LA1, KLA1 is shown as LA1, KAS1-KsA1 is shown as AS1-sA1, KsA1 is shown as sA1. Measurement of bone loss is the mean of the area measured in millimeters squared (mm2) from the cementoenamel junction (CEJ) to the alveolar bone crest (ABC) of the buccal side of each maxillary molar of both the left and right maxillae. Data was normally distributed as measured by Levene's homogeneity of variance and are presented as mean (n=12) in mm2 and were analyzed using the One-Way analysis of variance and Dunnett's T3 test. *, indicates group has significantly (P<0.001) less bone loss than control (infected) group. †, indicates group has significantly (P<0.001) more bone loss than the AS2-LA1 group.

Effect of immunization with the recombinant proteins (KsA1, KLA1, KAS1-KsA1 and KAS2-KLA1) on P. gingivalis induced alveolar bone loss in the mouse periodontitis model. The recombinant proteins KsA1, KLA1, KAS1-KsA1 and KAS2-KLA1, formalin killed P. gingivalis strain W50 and the RgpA-Kgp complex were used to determine and compare the protection induced against P. gingivalis induced alveolar bone loss using a modified mouse model of periodontal bone loss based on that reported by Baker et al (4). Mice were immunized (days 0 and 30) with either recombinant proteins KsA1, KLA1, KAS1-KsA1 or KAS2-KLA1, RgpA-Kgp complex or formalin killed P. gingivalis strain W50 (FK-W50) cells or PBS adjuvant alone and were then orally challenged with viable P. gingivalis W50. Immunization with all of the recombinant antigens, RgpA-Kgp complex and FK-W50 cells protected BALB/c mice against P. gingivalis-induced alveolar bone loss as these animals exhibited significantly (p<0.001) less bone loss compared to the PBS immunized group (FIG. 3). However the KAS2-KLA1 immunised mice had significantly less bone loss than mice immunised with KLA1 (p<0.01); KsA1 (p<0.001), RgpA-Kgp complex (p<0.001), FK-W50 cells (p<0.001) and non-challenged mice (p<0.001). There was no significant difference in bone loss between the KAS2-KLA1 and KAS1-KsA1 immunised mice. Furthermore, KAS1-KsA1 immunised mice exhibited significantly less bone loss than non-challenged mice (p<0.01) and RgpA-Kgp complex immunised mice (p<0.05), but were not significantly different from KsA1, KLA1, and FK-W50 immunised mice. There was no significant difference in bone loss between the KsA1, KLA1, RgpA-Kgp complex and FK-W50 immunised mice.

Example 4

Figure 4:
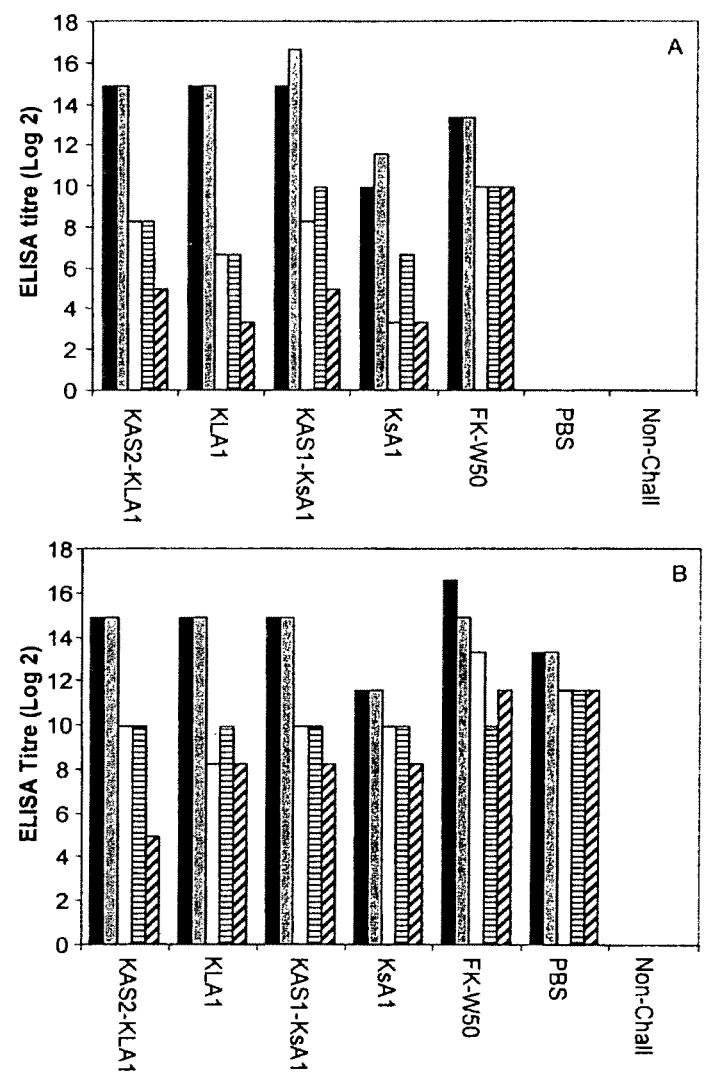
FIG. 4 shows serum antibody subclass responses of immunised mice in the periodontitis model. Sera from mice; A (pre-oral inoculation) and B (post-oral inoculation) immunised with recombinant proteins KsA1, KLA1, KAS1-KsA1 and KAS2-KLA1 and formalin killed *P. gingivalis* strain W50 were used in the ELISA with the formalin killed *P. gingivalis* strain W50 as the adsorbed antigen. Antibody responses IgG (black bars), IgG1 (grey bars), IgG2a (white bars), IgG2b (horizontal striped bars), IgG3 (diagonal striped bars), are expressed as the ELISA titre (log 2) obtained minus the background level, with each titre representing the mean±standard deviation of three values.

Antibody subclass responses induced by immunization with the recombinant proteins (KsA1, KLA1, KAS1-KsA1 and KAS2-KLA1) in the mouse periodontitis models. Prior and post to oral inoculation challenge with viable P. gingivalis cells mice were bled and the sera collected by centrifugation. FIG. 4 shows the antibody subclass reactivity to formalin-killed P. gingivalis W50 cells for each immunogen (KsA1, KLA1, KAS1-KsA1 or KAS2-KLA1 or formalin killed P. gingivalis strain W50 (FK-W50) cells) in the mouse periodontitis model. All of the protective immunogens induced a high IgG antibody titre to FK-W50. Furthermore, the predominant antibody subclass each protective immunogen induced was IgG1 with only weakly immunoreactive IgG2b and IgG3 FK-W50-specific antibodies (FIG. 4). The predominant antibody subclass induced by each immunogen both pre (FIG. 4A) and post-oral inoculation (FIG. 4B) was IgG1.

Example 5

Figure 5:
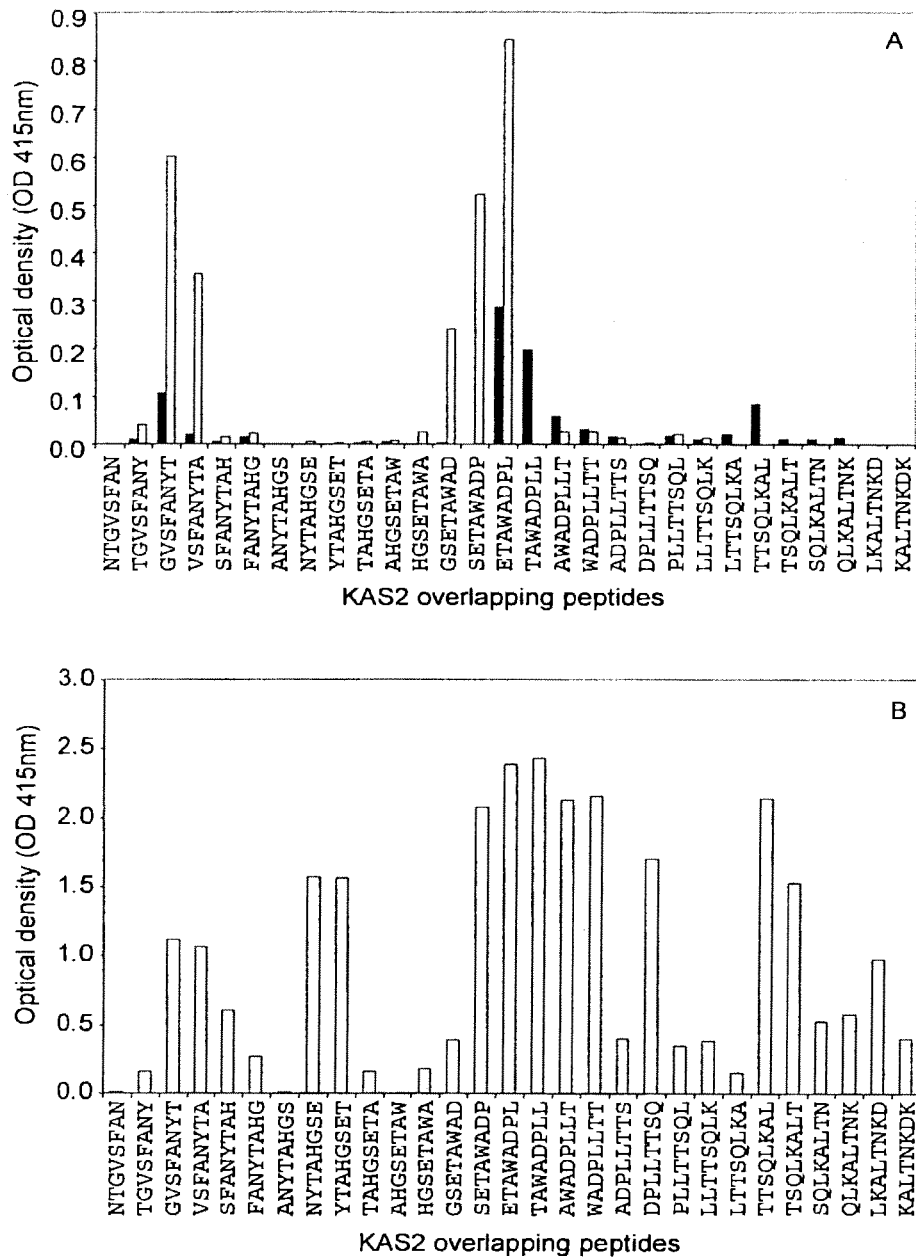
FIG. 5 shows a PEPSCAN analysis of peptide-specific antibody reactivity to overlapping peptides representing the KAS2 peptide sequence 433-468. (A) KAS2 overlapping peptides (offset 1, overlap 7) probed with KAS1-KsA1 (white bars), KAS2-KLA1 (black bars) antisera. (B) KAS2 overlapping peptides (offset, overlap 7) probed with KAS2-DT conjugate antisera. Each bar displays the antibody reactivity (optical density [OD] at 415 nm).

Epitope mapping of KAS2 (433-468). Overlapping biotinylated eight residue peptides (offset by one, overlap by seven) for KAS2 (433-468) were synthesised and used to coat streptavidin coated plates. The antibody binding epitopes were then identified using antisera from mice immunized with KAS1-KsA1, KAS2-KLA1 and KAS2-diphtheria toxoid conjugate (FIG. 5). A two fold increase in optical density (415 nm) above background was considered as a positive antibody response (threshold OD). The antisera recognised the following peptide sequences derived from SEQ ID No.28 viz. KAS1-KsA1 recognised peptides 435-442, 436-443, 445-452, 446-453 and 447-454 (threshold OD=0.07, FIG. 5A) whereas KAS2-KLA1 recognised peptides 435-442, 447-454 and 448-455 (threshold ID=0.07, FIG. 5A). This suggests recognition of a number of minimal epitopes viz. peptide 436-442 (VSFANYT and its variant VGFANYT), peptide 447-452 (ETAWAD and its variant ETSWAD), and peptide 448-453 (TAWADP and its variant TSWADP). Peptides which include the peptide 436-442 epitope include GVSFANYT, GVGFANYT, VSFANYTA and VGFANYTA. Peptides which include the peptide 447-452 and/or 448-453 epitopes include SETAWAD, SETSWAD, ETAWADP, ETSWADP, TAWADPL and TSWADPL, more particularly GSETAWAD, GSETSWAD, SETAWADP, SETSWADP, ETAWADPL, ETSWADPL, TAWADPLL and TSWADPLL.

Example 6

Synthesis of KAS and RAS peptides for conjugation to a protein.

Peptides were synthesized manually or using a CEM Microwave peptide synthesizer. Standard solid-phase peptide synthesis protocols for Fmoc chemistry were used throughout. Peptides were assembled as the carboxyamide form using Rink-linker derived AM-sure™ resin (AAPPTEC, KY, USA). Coupling was accomplished with HBTU/HOBt activation using 4 equiv of Fmoc-amino acid and 6 equiv of DIPEA. The Fmoc group was removed by 20% piperidine in 1 M HOBt/DMF Resins bearing KAS or RAS peptides were swollen in DMF and the N-terminal Fmoc group removed by 2% v/v DBU in DMF containing 2% v/v piperidine. The N-terminal amino group was then derivatised with S-Acetylmercaptoacetic acid (SAMA) group using 5 equiv of SAMA-OPfp and 5 equiv of HOBt. The reaction was monitored by the trinitrobenzene sulphonic acid (TNBSA) test. When a negative TNBSA test was returned the resin was washed (5×DMF, 3×DCM and 3×diethyl ether). The resin was then dried under vacuum. Cleavage of peptides from the resin support was performed using TFA:phenol:TIPS:EDT:water (92:2:2:2:2) cleavage cocktail for 2.5 hours or 4 hours depending on the arginine content of the peptide. After cleavage the resin was removed by filtration and the filtrate concentrated to approximately 1mL under a stream of nitrogen. After the peptide products were precipitated in cold ether, they were centrifuged and washed three times. The peptide precipitates were dissolved in 5 to 10 mL of water containing 0.1% v/v TFA and insoluble residue removed by centrifugation. Peptides were purified by RP-HPLC.

A number of different chemical moieties can be used for derivatising peptides for conjugation to proteins, these would introduced reactive groups such as; halides (bromo, chloro and iodo), maleimido, succinimidyl, hydrazinyl, oxime, thiol, which would then be used conjugate the derivatised peptide to a protein such as KgpA1 through its native cysteine residues or has been derivatised with the complementary reactive group that allows the chemical ligation to proceed to form a peptide-protein conjugate.

Conjugation of SAMA-peptides to KA1. To a solution, containing 10 mg/mL of recombinant KA1 or other adhesin domain of the RgpA-Kgp complex in phosphate-buffered saline (0.1M sodium phosphate, 0.9% NaCl, pH 7.4) was added 0.1 mL of a 1% w/v solution of m-maleimido benzoyl-N-hydroxysuccinimide ester (MBS) in DMF. After 30 min unreacted MBS was removed and MBS-modified KA1 collected by gel filtration using a PD10 column (Pharmacia, NSW, Australia) equilibrated in conjugation buffer (0.1M sodium phosphate, 5 mM EDTA; pH 6.0). Purified SAMA-peptide (1.3 µmole) was dissolved in 200 µL 6M guanidine HCl containing 0.5 M Tris; 2 mM EDTA, pH 6.0 and diluted with 8004 MilliQ water and deprotected in-situ by addition of 25 µL of 2M $NH_2OH$ (40 equiv) dissolved in MilliQ water. The collected MBS-KA1 was immediately reacted with deprotected SAMA-peptide and stirred for one hour at room temperature. The peptide-KA1 conjugate was separated from unreacted peptide by gel filtration using a PD10 column equilibrated in PBS pH 7.4 and lyophilized. The reaction was monitored using the Ellmans test.

Example 7

Preparation of antibodies. Polyclonal antiserum to recombinant proteins are raised in mice by immunising with the proteins subcutaneously. The mice are immunised at day 0 with 25 µg of protein in incomplete Freund's adjuvant and day 30 with 25 µg of protein in incomplete Freund's adjuvant. Immunisations are carried out using standard procedures. Polyclonal antisera having a high titre against the proteins are obtained. If desired monoclonal antibodies directed specifically against recombinant proteins are obtained using standard procedures.

Example 8

Immunization for the generation of antibodies. BALB/c mice or CD1 (Swiss out bred mices) 6-8 weeks old (10 mice per group) were immunized subcutaneously (s.c. 100 µl) with either 50 µg of the KAS2-LA1 chimera and the antigen emulsified in incomplete Freund's adjuvant (IFA). After 30 days the mice were boosted with antigen (s.c. injection, emulsified in IFA) and 12 days later the mice were killed and cardiac bled to collect sera.

Determination of subclass antibody by an ELISA. To determine the subclass antibody responses of mouse sera, enzyme-linked immunosorbent assays (ELISAs) were performed in triplicate using a 5-µg/ml solution of KAS2-LA1 chimera or formalin killed *P. gingivalis* W50 or the RgpA-Kgp complex in phosphate-buffered saline (PBS) (0.01 M $Na_2HPO_4$, 1.5 mM $KH_2PO_4$, 0.15 M NaCl), pH 7.0, containing 0.1% (vol/vol) Tween 20 (PBST) to coat wells of flat-bottom polyvinyl microtiter plates (Dynatech Laboratories, McLean, Va.). After removal of the coating solution, PBST containing 2% (wt/vol) skim milk powder was added to wells to block the uncoated plastic for 1 h at room temperature. After the wells were washed four times with PBST, serial dilutions of mouse sera in PBST containing 0.5% (wt/vol) skim milk (SK-PBST) were added to each well and incubated for 16 h at room temperature. After the wells were washed six times with PBST, a 1/2,000 dilution of goat IgG to mouse IgM, IgA, IgG1, IgG2a, IgG2b, or IgG3 (Sigma, New South Wales, Australia) was added in SK-PBST and allowed to bind for 2 h at room temperature. Plates were washed six times in PBST, and a 1/5,000 dilution of horseradish peroxidase-conjugated rabbit anti-goat immunoglobulin (Sigma, New South Wales, Australia) in SK-PBST was added to each well and incubated for 1 h at room temperature. After the wells were washed six times with PBST, bound antibody was detected by the addition of 100 µl of ABTS substrate[0.9 mM 2,2'-azino-bis(3-ethyl-benz-thiazoline-6) sulfonic acid in 80 mM citric acid containing 0.005% (vol/vol) hydrogen peroxide, pH 4.0] to each well. The optical density at 415 nm was measured using a microplate reader (Bio-Rad microplate reader, model 450).

Figure 6:
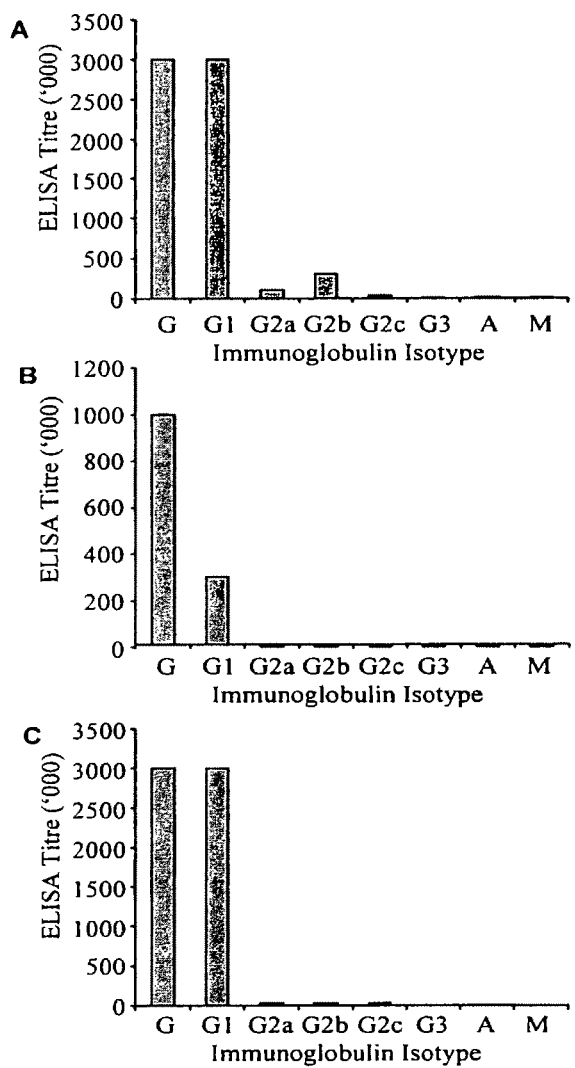
FIG. 6. Chimera AS2-LA1 induces an antibody response in outbred mice that recognises *P. gingivalis* whole cells and the RgpA-Kgp complex. CD1 outbred mice were immunised with chimera AS2-LA1 (50 mg/mouse) and the collected sera used in ELISA with AS2-LA1 (A), formalin killed *P. gingivalis* strain W50 (B) and RgpA-Kgp complex (C) as the absorbed antigens. In this figure KAS2-KLA1 is shown as AS2-LA1. The titre for each immunoglulgin isotype to each antigen was determined and the data expressed as the ELISA titre ('000) obtained minus double the background level, with each titre representing the mean±standard deviation of three values.

Antibody subclass responses induced by immunization with the recombinant protein KAS2-KLA1 in outbred (CD1, Swiss) mice. CD1 (Swiss) mice were immunised with the KAS2-LA1 chimera, bled and the sera collected by centrifugation. FIG. 6 shows the antibody subclass reactivity to KAS2-LA1 chimera, formalin-killed *P. gingivalis* W50 cells and the RgpA-Kgp complex. The KAS2-LA1 chimera induced a strong IgG antibody with a predominant IgG1 antibody response that recognised the KAS2-LA1 chimera and cross reacted strongly with FK *P. gingivalis* W50 cells and the RgpA-Kgp complex (FIG. 6). Furthermore, the KAS2-LA1 chimera induced only weak immunoreactive IgG2a, IgG2b and IgG3 antigen-specific antibodies (FIG. 6).

Example 9

Development of a Kgp structural model and identification of active site surface accessible sequences.

Our work has shown that Kgp proteinase active site peptides are highly immunogenic and induce high levels of protection, against *P. gingivalis*-induced bone loss. In an attempt to identify further proteinase active site peptides as vaccine candidates a model of the catalytic domain of Kgp was developed using the Orchestrar suite of programs within Sybyl7.3 (FIG. 7). The model is based on PDB structure 1 cry of the RgpB protease from *P. gingivalis*, the proteins have a 23.58% pairwise identity and the Z-score is 25.09 (a high-confidence model). The Meta-PPisp protein interaction server predicts two protein-protein interaction surfaces for Kgp: the substrate binding surface (as in RgpB), and a second surface unique to Kgp. The major differences between the RgpB and Kgp models are in the loops that frame the second interaction surface and a 19-residue gap (Val526 to Phe545) that couldn't be modeled in Kgp that falls within the second interaction surface. FIG. 7 shows the Kgp model with the thicker ribbons showing surface accessible sequences around the proteinase active site of Kgp, the surface accessible sequences were found to be Asp388-Gln394, Leu421-Ala423, Ala443-Glu447 with Ala451, Asn510-Trp513, and Ile570-Gly577 with Tyr580. From the model (FIG. 6) it is evident that along with KAS2 (A) three other sequences KAS4 (Asp388-Val395) (B), KAS5 (Asn510-Asp516) (C) and KAS6 (Ile570-Tyr580) (D) are prominent and of sufficient length to be vaccine targets. Thus a recombinant chimera protein can be produced that has each of these peptides in sequence and joined on to the N-terminus of KLA1 to produce multiKAS-KLA1, that can be used to induce an immune response and hence to protect against *P. gingivalis* related diseases or conditions.

Example 10

Process for modelling Arg-X-proteinase to identify immunogenic regions flanking the catalytic site.

The Arg-X proteinase three dimensional structure was determined according to the methods of Eichinger A, Beisel H G, Jacob U, Huber R, Medrano F J, Banbula A, Potempa J, Travis J, Bode W. Crystal structure of gingipain R: an Arg-specific bacterial cysteine proteinasewith a caspase-like fold. EMBO J. 1999 Oct. 15; 18(20):5453-62

Example 11

The following is an example of a toothpaste formulation containing antibodies.

| Ingredient | % w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Goat serum containing specific antibodies | 0.2 |
| Water | balance |

Example 12

The following is an example of a toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroylسarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing specific antibodies | 0.2 |
| Water | balance |

Example 13

The following is an example of a toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine milk Ig containing specific antibodies | 0.1 |
| Water | balance |

Example 14

The following is an example of a toothpaste formulation.

| Ingredient | % w/w |
|---|---|
| Sorbitol | 22.0 |
| Irish moss | 1.0 |
| Sodium Hydroxide (50%) | 1.0 |
| Gantrez ® | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| Mouse monoclonal antibodies 0.3 sodium lauryl sulphate | 2.00 |

Example 15

The following is an example of a liquid toothpaste formulation.

| Ingredient | % w/w |
|---|---|
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |

-continued

| Ingredient | % w/w |
| --- | --- |
| Equine Ig containing specific antibodies | 0.2 |
| Linolic acid | 0.05 |
| Water | balance |

Example 16

The following is an example of a mouthwash formulation.

| Ingredient | % w/w |
| --- | --- |
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Rabbit Ig containing specific antibodies | 0.2 |
| Water | balance |

Example 17

The following is an example of a mouthwash formulation.

| Ingredient | % w/w |
| --- | --- |
| Gantrez ® S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Mouse monoclonal antibodies | 0.3 |
| Water | balance |

Example 18

The following is an example of a lozenge formulation.

| Ingredient | % w/w |
| --- | --- |
| Sugar | 75-80 |
| Corn syrup | 1-20 |
| Flavour oil | 1-2 |
| NaF | 0.01-0.05 |
| Mouse monoclonal antibodies | 0.3 |
| Mg stearate | 1-5 |
| Water | balance |

Example 19

The following is an example of a gingival massage cream formulation.

| Ingredient | % w/w |
| --- | --- |
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |

-continued

| Ingredient | % w/w |
| --- | --- |
| Chlorohexidine gluconate | 0.1 |
| Mouse monoclonal antibodies | 0.3 |
| Water | balance |

Example 20

The following is an example of a chewing gum formulation.

| Ingredient | % w/w |
| --- | --- |
| Gum base | 30.0 |
| Calcium carbonate | 2.0 |
| Crystalline sorbitol | 53.0 |
| Glycerine | 0.5 |
| Flavour oil | 0.1 |
| Mouse monoclonal antibodies | 0.3 |
| Water | balance |

Example 21

The following is an example of a pharmaceutical formulation

| Ingredient | % w/w |
| --- | --- |
| Humanised specific monoclonal antibodies | 10 |
| Sterile phosphate buffered saline | 90 |

Example 22

The following is an example of a periodontal gel formulation.

| Ingredient | % w/w |
| --- | --- |
| Pluronic ® F127 | 20.0 |
| Stearyl alcohol | 8.0 |
| Specific antibodies | 3.0 |
| Colloidal silicon dioxide (Aerosil ® 200) | 1.0 |
| Chlorhexidine gluconate | 0.1 |
| Water | balance |

It should be understood that while the invention has been described in details herein, the examples are for illustrative purposes only. Other modifications of the embodiments of the present invention that are obvious to those skilled in the art of molecular biology, dental diagnostics, and related disciplines are intended to be within the scope of the invention.

REFERENCES

1. McKee, A. S., A. S. McDermid, A. Baskerville, A. B. Dowsett, D. C. Ellwood, and P. D. Marsh. 1986. Effect of hemin on the physiology and virulence of *Bacteroides gingivalis* W50. *Infect. Immun.* 52:349-355.
2. Slots, J. 1982. *Importance of black-pigmented Bacteroides in human periodontal disease. Host parasite interactions in periodontal diseases.* American Society for Microbiology.

3. O'Brien-Simpson, N. M., R. Pathirana, R. A. Paolini, Y.-Y. Chen, P. D. Veith, T. V., R. N. Pike, N. Alley, and E. C. Reynolds. 2005. An immune response directed to proteinase and adhesin functional epitopes protects against *Porphyromonas gingivalis*-induced bone loss. *Journal of Immunology* 175:3980-3989.

4. Baker, P. J., R. T. Evans, and D. C. Roopenian. 1994. Oral infection with *Porphyromonas gingivalis* and induced alveolar bone loss in immunocompetent and severe combined immunodeficient mice. *Arch Oral Biol* 39:1035-1040.

The claims defining the invention are as follows:

1. A method of reducing the secerity of a *P. gingivalis*-related disease or condition in a subject, comprising administering to the subject an antibody raised against a chimeric or fusion protein comprising a first peptide joined directly or through a linker to a second peptide or polypeptide, wherein:

(A) said first peptide comprises a region of a *P. gingivalis* trypsin-like enzyme selected from the group consisting of the amino acid sequence that is the same as, or at least 90% homologous to, the sequence shown in any one of SEQ ID NOs: 1-34; and
(B) said second peptide or polypeptide is selected from the group consisting of:
  (i) the amino acid sequence that is the same as, or at least 90% homologous to, the sequence of an adhesin domain of the Lys-X-proteinase of *P. gingivalis* shown in any one of SEQ ID NOs: 35-37 and 40-43; and
  (ii) the amino acid sequence that is the same as, or at least 90% homologous to, the sequence of an adhesin domain of the Arg-X-proteinase of *P. gingivalis* shown in any one of SEQ ID NOs: 38-39 and 44-46;
  (iii) the amino acid sequence that is the same as, or at least 90% homologous to, the sequence of a HagA adhesin domain of *P. gingivalis* shown in any one of SEQ ID NOs: 80-82; and
  (iv) the amino acid sequence that is the same as or at least 90% homologous to, the sequence shown in any one of SEQ ID NOs: 69-79 and 83 to 85.

2. The method according to claim 1, wherein the first peptide of the chimeric or fusion peptide comprises or consists of a sequence shown in one of more of SEQ ID NOs. 3 to 26.

3. The method according to claim 1, wherein the antibody is a monoclonal antibody.

4. The method according to claim 1, wherein:
(A) the first peptide of the chimeric or fusion protein comprises a sequence selected from the group consisting of KAS1 (SEQ ID NO: 27), KAS2 (SEQ ID NO: 28), KAS3 (SEQ ID NO: 29), PAS1K (SEQ ID NO: 30), RAS1 (SEQ ID NO: 31), RAS2 (SEQ ID NO:32), KAS3 (SEQ ID NO: 33), and PAS1R (SEQ ID NO: 34), and
(B) the second peptide or polypeptide of the chimeric or fusion protein comprises a sequence (i) selected from the group consisting of KA1 (SEQ ID NO: 35), KA2 (SEQ ID NO: 40), KA3 (SEQ ID NO: 41), KA4 (SEQ ID NO: 42), KA5 (SEQ ID NO: 43), RA1 (SEQ ID NO: 38), RA2 (SEQ ID NO: 44), RA3 (SEQ ID NO: 45), RA4 (SEQ ID NO: 46), HA1 (SEQ ID NO: 80), HA1* (SEQ ID NO: 81), HA1** (SEQ ID NO: 82), or (ii) selected from the group consisting of SEQ ID NOs. 69-79, or (iii) selected from the group consisting of SEQ ID NOs. 83-85.

5. The method according to claim 1, wherein the chimeric or fusion protein comprises at least two sequences that are the same as, or at least 90% homologous to, a sequence selected from the group consisting of KAS1 (SEQ ID NO: 27), KAS2(SEQ ID NO: 28), KAS3 (SEQ ID NO: 29), PAS1K (SEQ ID NO: 30), RAS1 (SEQ ID NO: 31), RAS2 (SEQ ID NO: 32), RAS3 (SEQ ID NO: 33), and PAS1R (SEQ ID NO: 34).

6. The method according to claim 1, wherein said first peptide of the chimeric or fusion protein comprises the amino acid sequence selected from the group consisting of SEQ ID NOs: 3-34 and sequences at least 90% homologous thereto.

7. The method according to claim 1, wherein said second peptide or polypeptide of the chimeric or fusion protein comprises the amino acid sequence selected from the group consisting of SEQ ID NOs: 35-39 and sequences at least 90% homologous thereto.

8. The method according to claim 1, wherein:
(a) said first peptide of the chimeric or fusion protein comprises the amino acid sequence that is the same as or at least 90% homologous to the sequence shown in any one of SEQ ID NOs: 27-30 and said second peptide or polypeptide of the chimeric or fusion protein comprises the amino sequence that is the same as or at least 90% homologous to the sequence shown in any one of SEQ ID NOs: 36-37; or
(b) said first peptide of the chimeric or fusion protein comprises the amino acid sequence that is the same as or at least 90% homologous to the sequence shown in any one of SEQ ID NOs: 31-34 and said second peptide or polypeptide of the chimeric or fusion protein comprises a sequence that is the same as or at least 90% homologous to SEQ ID NO:39.

9. The method according to claim 1, wherein said second peptide or polypeptide of the chimeric or fusion protein comprises or consists of the sequence shown in one or more of SEQ ID NOs. 69 to 79 or one or more of SEQ ID NOs. 83 to 85.

10. The method according to claim 9, wherein said first peptide of the chimeric or fusion protein comprises or consists of the sequence shown in one of more of SEQ ID NOs. 3 to 26.

11. The method according to claim 1, wherein said first peptide of the chimeric or fusion protein comprises the sequence that is the same as or at least 90% homologous to the sequence shown in SEQ ID NO:28 and said second peptide or polypeptide of the chimeric or fusion protein comprises the sequence that is the same as or at least 90% homologous to the sequence shown in SEQ ID NO: 37.

12. The method according to claim 1, wherein said first peptide of the chimeric or fusion protein comprises the sequence that is the same as or at least 90% homologous to the sequence shown in SEQ ID NO:27 and said second peptide or polypeptide comprises the sequence that is the same as or at least 90% homologous to the sequence shown in SEQ ID NO:36.

\* \* \* \* \*

UNITED STATES PATENT AND TRADEMARK OFFICE
CERTIFICATE OF CORRECTION

| | | |
|---|---|---|
| PATENT NO. | : 9,518,109 B2 | Page 1 of 1 |
| APPLICATION NO. | : 14/487461 | |
| DATED | : December 13, 2016 | |
| INVENTOR(S) | : Eric Charles Reynolds et al. | |

It is certified that error appears in the above-identified patent and that said Letters Patent is hereby corrected as shown below:

On the Title Page

Item (63), in the Related U.S. Application Data, please delete:
"Continuation of application no. 13/060,653, filed as application No. PCT/AU2009/001112 on Aug. 28, 2009, now Pat. No. 8,871,213."

And insert: -- Divisional of application no. 13/060,653, filed as application No. PCT/AU2009/001112 on Aug. 28, 2009, now Pat. No. 8,871,213. --.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*

```
                           SEQUENCE LISTING

<160> NUMBER OF SEQ ID NOS: 85

<210> SEQ ID NO 1
<211> LENGTH: 37
<212> TYPE: PRT
<213> ORGANISM: Porphyromonas gingivalis
<220> FEATURE:
<221> NAME/KEY: MISC_FEATURE
<222> LOCATION: (6)..(6)
<223> OTHER INFORMATION: X can be either G or S
<220> FEATURE:
<221> NAME/KEY: MISC_FEATURE
<222> LOCATION: (18)..(18)
<223> OTHER INFORMATION: X can be either S or A
<220> FEATURE:
<221> NAME/KEY: MISC_FEATURE
<222> LOCATION: (23)..(23)
<223> OTHER INFORMATION: X can be either S or L
<220> FEATURE:
<221> NAME/KEY: MISC_FEATURE
<222> LOCATION: (24)..(24)
<223> OTHER INFORMATION: X can be either L or V
<220> FEATURE:
<221> NAME/KEY: MISC_FEATURE
<222> LOCATION: (26)..(26)
<223> OTHER INFORMATION: X can be either A or T
<220> FEATURE:
<221> NAME/KEY: MISC_FEATURE
<222> LOCATION: (27)..(27)
<223> OTHER INFORMATION: X can be either T or S
<220> FEATURE:
<221> NAME/KEY: MISC_FEATURE
<222> LOCATION: (29)..(29)
<223> OTHER INFORMATION: X can be either V or L
<220> FEATURE:
<221> NAME/KEY: MISC_FEATURE
<222> LOCATION: (36)..(36)
<223> OTHER INFORMATION: X can be either D or N

<400> SEQUENCE: 1

Leu Asn Thr Gly Val Xaa Phe Ala Asn Tyr Thr Ala His Gly Ser Glu
1               5                   10                  15

Thr Xaa Trp Ala Asp Pro Xaa Xaa Thr Xaa Xaa Gln Xaa Lys Ala Leu
            20                  25                  30

Thr Asn Lys Xaa Lys
        35

<210> SEQ ID NO 2
<211> LENGTH: 37
<212> TYPE: PRT
<213> ORGANISM: Porphyromonas gingivalis
<220> FEATURE:
<221> NAME/KEY: MISC_FEATURE
<222> LOCATION: (8)..(8)
<223> OTHER INFORMATION: X can be either V or A

<400> SEQUENCE: 2

Phe Asn Gly Gly Ile Ser Leu Xaa Asn Tyr Thr Gly His Gly Ser Glu
1               5                   10                  15

Thr Ala Trp Gly Thr Ser His Phe Gly Thr Thr His Val Lys Gln Leu
            20                  25                  30

Thr Asn Ser Asn Gln
        35
```

```
<210> SEQ ID NO 3
<211> LENGTH: 7
<212> TYPE: PRT
<213> ORGANISM: Porphyromonas gingivalis

<400> SEQUENCE: 3

Val Ser Phe Ala Asn Tyr Thr
1               5

<210> SEQ ID NO 4
<211> LENGTH: 7
<212> TYPE: PRT
<213> ORGANISM: Porphyromonas gingivalis

<400> SEQUENCE: 4

Val Gly Phe Ala Asn Tyr Thr
1               5

<210> SEQ ID NO 5
<211> LENGTH: 8
<212> TYPE: PRT
<213> ORGANISM: Porphyromonas gingivalis

<400> SEQUENCE: 5

Gly Val Ser Phe Ala Asn Tyr Thr
1               5

<210> SEQ ID NO 6
<211> LENGTH: 8
<212> TYPE: PRT
<213> ORGANISM: Porphyromonas gingivalis

<400> SEQUENCE: 6

Gly Val Gly Phe Ala Asn Tyr Thr
1               5

<210> SEQ ID NO 7
<211> LENGTH: 8
<212> TYPE: PRT
<213> ORGANISM: Porphyromonas gingivalis

<400> SEQUENCE: 7

Val Ser Phe Ala Asn Tyr Thr Ala
1               5

<210> SEQ ID NO 8
<211> LENGTH: 8
<212> TYPE: PRT
<213> ORGANISM: Porphyromonas gingivalis

<400> SEQUENCE: 8

Val Gly Phe Ala Asn Tyr Thr Ala
1               5

<210> SEQ ID NO 9
<211> LENGTH: 6
<212> TYPE: PRT
<213> ORGANISM: Porphyromonas gingivalis

<400> SEQUENCE: 9

Glu Thr Ala Trp Ala Asp
1               5
```

```
<210> SEQ ID NO 10
<211> LENGTH: 6
<212> TYPE: PRT
<213> ORGANISM: Porphyromonas gingivalis

<400> SEQUENCE: 10

Glu Thr Ser Trp Ala Asp
1               5

<210> SEQ ID NO 11
<211> LENGTH: 6
<212> TYPE: PRT
<213> ORGANISM: Porphyromonas gingivalis

<400> SEQUENCE: 11

Thr Ala Trp Ala Asp Pro
1               5

<210> SEQ ID NO 12
<211> LENGTH: 6
<212> TYPE: PRT
<213> ORGANISM: Porphyromonas gingivalis

<400> SEQUENCE: 12

Thr Ser Trp Ala Asp Pro
1               5

<210> SEQ ID NO 13
<211> LENGTH: 7
<212> TYPE: PRT
<213> ORGANISM: Porphyromonas gingivalis

<400> SEQUENCE: 13

Ser Glu Thr Ala Trp Ala Asp
1               5

<210> SEQ ID NO 14
<211> LENGTH: 7
<212> TYPE: PRT
<213> ORGANISM: Porphyromonas gingivalis

<400> SEQUENCE: 14

Ser Glu Thr Ser Trp Ala Asp
1               5

<210> SEQ ID NO 15
<211> LENGTH: 7
<212> TYPE: PRT
<213> ORGANISM: Porphyromonas gingivalis

<400> SEQUENCE: 15

Glu Thr Ala Trp Ala Asp Pro
1               5

<210> SEQ ID NO 16
<211> LENGTH: 7
<212> TYPE: PRT
<213> ORGANISM: Porphyromonas gingivalis

<400> SEQUENCE: 16

Glu Thr Ser Trp Ala Asp Pro
1               5

<210> SEQ ID NO 17
<211> LENGTH: 7
```

```
<212> TYPE: PRT
<213> ORGANISM: Porphyromonas gingivalis

<400> SEQUENCE: 17

Thr Ala Trp Ala Asp Pro Leu
1               5

<210> SEQ ID NO 18
<211> LENGTH: 7
<212> TYPE: PRT
<213> ORGANISM: Porphyromonas gingivalis

<400> SEQUENCE: 18

Thr Ser Trp Ala Asp Pro Leu
1               5

<210> SEQ ID NO 19
<211> LENGTH: 8
<212> TYPE: PRT
<213> ORGANISM: Porphyromonas gingivalis

<400> SEQUENCE: 19

Gly Ser Glu Thr Ala Trp Ala Asp
1               5

<210> SEQ ID NO 20
<211> LENGTH: 8
<212> TYPE: PRT
<213> ORGANISM: Porphyromonas gingivalis

<400> SEQUENCE: 20

Gly Ser Glu Thr Ser Trp Ala Asp
1               5

<210> SEQ ID NO 21
<211> LENGTH: 8
<212> TYPE: PRT
<213> ORGANISM: Porphyromonas gingivalis

<400> SEQUENCE: 21

Ser Glu Thr Ala Trp Ala Asp Pro
1               5

<210> SEQ ID NO 22
<211> LENGTH: 8
<212> TYPE: PRT
<213> ORGANISM: Porphyromonas gingivalis

<400> SEQUENCE: 22

Ser Glu Thr Ser Trp Ala Asp Pro
1               5

<210> SEQ ID NO 23
<211> LENGTH: 8
<212> TYPE: PRT
<213> ORGANISM: Porphyromonas gingivalis

<400> SEQUENCE: 23

Glu Thr Ala Trp Ala Asp Pro Leu
1               5

<210> SEQ ID NO 24
<211> LENGTH: 8
<212> TYPE: PRT
<213> ORGANISM: Porphyromonas gingivalis
```

<400> SEQUENCE: 24

Glu Thr Ser Trp Ala Asp Pro Leu
1               5

<210> SEQ ID NO 25
<211> LENGTH: 8
<212> TYPE: PRT
<213> ORGANISM: Porphyromonas gingivalis

<400> SEQUENCE: 25

Thr Ala Trp Ala Asp Pro Leu Leu
1               5

<210> SEQ ID NO 26
<211> LENGTH: 8
<212> TYPE: PRT
<213> ORGANISM: Porphyromonas gingivalis

<400> SEQUENCE: 26

Thr Ser Trp Ala Asp Pro Leu Leu
1               5

<210> SEQ ID NO 27
<211> LENGTH: 23
<212> TYPE: PRT
<213> ORGANISM: Porphyromonas gingivalis
<220> FEATURE:
<221> NAME/KEY: MISC_FEATURE
<222> LOCATION: (6)..(6)
<223> OTHER INFORMATION: X can be either G or S
<220> FEATURE:
<221> NAME/KEY: MISC_FEATURE
<222> LOCATION: (18)..(18)
<223> OTHER INFORMATION: X can be either S or A
<220> FEATURE:
<221> NAME/KEY: MISC_FEATURE
<222> LOCATION: (23)..(23)
<223> OTHER INFORMATION: X can be either S or L

<400> SEQUENCE: 27

Leu Asn Thr Gly Val Xaa Phe Ala Asn Tyr Thr Ala His Gly Ser Glu
1               5                   10                  15
Thr Xaa Trp Ala Asp Pro Xaa
            20

<210> SEQ ID NO 28
<211> LENGTH: 36
<212> TYPE: PRT
<213> ORGANISM: Porphyromonas gingivalis
<220> FEATURE:
<221> NAME/KEY: MISC_FEATURE
<222> LOCATION: (5)..(5)
<223> OTHER INFORMATION: X can be either G or S
<220> FEATURE:
<221> NAME/KEY: MISC_FEATURE
<222> LOCATION: (17)..(17)
<223> OTHER INFORMATION: X can be either S or A
<220> FEATURE:
<221> NAME/KEY: MISC_FEATURE
<222> LOCATION: (22)..(22)
<223> OTHER INFORMATION: X can be either S or L
<220> FEATURE:
<221> NAME/KEY: MISC_FEATURE
<222> LOCATION: (23)..(23)
<223> OTHER INFORMATION: X can be either L or V
<220> FEATURE:
<221> NAME/KEY: MISC_FEATURE
<222> LOCATION: (25)..(25)
<223> OTHER INFORMATION: X can be either A or T

```
<220> FEATURE:
<221> NAME/KEY: MISC_FEATURE
<222> LOCATION: (26)..(26)
<223> OTHER INFORMATION: X can be either T or S
<220> FEATURE:
<221> NAME/KEY: MISC_FEATURE
<222> LOCATION: (28)..(28)
<223> OTHER INFORMATION: X can be either V or L
<220> FEATURE:
<221> NAME/KEY: MISC_FEATURE
<222> LOCATION: (35)..(35)
<223> OTHER INFORMATION: X can be either D or N

<400> SEQUENCE: 28

Asn Thr Gly Val Xaa Phe Ala Asn Tyr Thr Ala His Gly Ser Glu Thr
1               5                   10                  15

Xaa Trp Ala Asp Pro Xaa Xaa Thr Xaa Xaa Gln Xaa Lys Ala Leu Thr
            20                  25                  30

Asn Lys Xaa Lys
        35

<210> SEQ ID NO 29
<211> LENGTH: 20
<212> TYPE: PRT
<213> ORGANISM: Porphyromonas gingivalis
<220> FEATURE:
<221> NAME/KEY: MISC_FEATURE
<222> LOCATION: (2)..(2)
<223> OTHER INFORMATION: X can be either G or S
<220> FEATURE:
<221> NAME/KEY: MISC_FEATURE
<222> LOCATION: (14)..(14)
<223> OTHER INFORMATION: X can be either S or A
<220> FEATURE:
<221> NAME/KEY: MISC_FEATURE
<222> LOCATION: (19)..(19)
<223> OTHER INFORMATION: X can be either S or L
<220> FEATURE:
<221> NAME/KEY: MISC_FEATURE
<222> LOCATION: (20)..(20)
<223> OTHER INFORMATION: X can be either L or V

<400> SEQUENCE: 29

Val Xaa Phe Ala Asn Tyr Thr Ala His Gly Ser Glu Thr Xaa Trp Ala
1               5                   10                  15

Asp Pro Xaa Xaa
            20

<210> SEQ ID NO 30
<211> LENGTH: 22
<212> TYPE: PRT
<213> ORGANISM: Porphyromonas gingivalis

<400> SEQUENCE: 30

Leu Asn Thr Gly Val Ser Phe Ala Asn Tyr Thr Ala His Gly Ser Glu
1               5                   10                  15

Thr Ala Trp Ala Asp Pro
            20

<210> SEQ ID NO 31
<211> LENGTH: 23
<212> TYPE: PRT
<213> ORGANISM: Porphyromonas gingivalis
<220> FEATURE:
<221> NAME/KEY: MISC_FEATURE
<222> LOCATION: (8)..(8)
<223> OTHER INFORMATION: X can be either V or A

<400> SEQUENCE: 31
```

```
Phe Asn Gly Gly Ile Ser Leu Xaa Asn Tyr Thr Gly His Gly Ser Glu
1               5                   10                  15

Thr Ala Trp Gly Thr Ser His
            20
```

<210> SEQ ID NO 32
<211> LENGTH: 36
<212> TYPE: PRT
<213> ORGANISM: Porphyromonas gingivalis
<220> FEATURE:
<221> NAME/KEY: MISC_FEATURE
<222> LOCATION: (7)..(7)
<223> OTHER INFORMATION: X can be either V or A

<400> SEQUENCE: 32

```
Asn Gly Gly Ile Ser Leu Xaa Asn Tyr Thr Gly His Gly Ser Glu Thr
1               5                   10                  15

Ala Trp Gly Thr Ser His Phe Gly Thr Thr His Val Lys Gln Leu Thr
            20                  25                  30

Asn Ser Asn Gln
            35
```

<210> SEQ ID NO 33
<211> LENGTH: 20
<212> TYPE: PRT
<213> ORGANISM: Porphyromonas gingivalis
<220> FEATURE:
<221> NAME/KEY: MISC_FEATURE
<222> LOCATION: (4)..(4)
<223> OTHER INFORMATION: X can be either V or A

<400> SEQUENCE: 33

```
Ile Ser Leu Xaa Asn Tyr Thr Gly His Gly Ser Glu Thr Ala Trp Gly
1               5                   10                  15

Thr Ser His Phe
            20
```

<210> SEQ ID NO 34
<211> LENGTH: 21
<212> TYPE: PRT
<213> ORGANISM: Porphyromonas gingivalis

<400> SEQUENCE: 34

```
Phe Asn Gly Gly Ile Ser Leu Ala Asn Tyr Thr Gly His Gly Ser Glu
1               5                   10                  15

Thr Ala Trp Gly Thr
            20
```

<210> SEQ ID NO 35
<211> LENGTH: 362
<212> TYPE: PRT
<213> ORGANISM: Porphyromonas gingivalis

<400> SEQUENCE: 35

```
Ala Asn Glu Ala Lys Val Val Leu Ala Ala Asp Asn Val Trp Gly Asp
1               5                   10                  15

Asn Thr Gly Tyr Gln Phe Leu Leu Asp Ala Asp His Asn Thr Phe Gly
            20                  25                  30

Ser Val Ile Pro Ala Thr Gly Pro Leu Phe Thr Gly Thr Ala Ser Ser
            35                  40                  45

Asn Leu Tyr Ser Ala Asn Phe Glu Tyr Leu Ile Pro Ala Asn Ala Asp
        50                  55                  60
```

```
Pro Val Val Thr Thr Gln Asn Ile Ile Val Thr Gly Gln Gly Glu Val
 65                  70                  75                  80

Val Ile Pro Gly Gly Val Tyr Asp Tyr Cys Ile Thr Asn Pro Glu Pro
                 85                  90                  95

Ala Ser Gly Lys Met Trp Ile Ala Gly Asp Gly Asn Gln Pro Ala
            100                 105                 110

Arg Tyr Asp Asp Phe Thr Phe Glu Ala Gly Lys Lys Tyr Thr Phe Thr
            115                 120                 125

Met Arg Arg Ala Gly Met Gly Asp Gly Thr Asp Met Glu Val Glu Asp
            130                 135                 140

Asp Ser Pro Ala Ser Tyr Thr Tyr Thr Val Tyr Arg Asp Gly Thr Lys
145                 150                 155                 160

Ile Lys Glu Gly Leu Thr Ala Thr Thr Phe Glu Glu Asp Gly Val Ala
                165                 170                 175

Ala Gly Asn His Glu Tyr Cys Val Glu Val Lys Tyr Thr Ala Gly Val
            180                 185                 190

Ser Pro Lys Val Cys Lys Asp Val Thr Val Glu Gly Ser Asn Glu Phe
            195                 200                 205

Ala Pro Val Gln Asn Leu Thr Gly Ser Ser Val Gly Gln Lys Val Thr
210                 215                 220

Leu Lys Trp Asp Ala Pro Asn Gly Thr Pro Asn Pro Asn Pro Asn Pro
225                 230                 235                 240

Asn Pro Asn Pro Gly Thr Thr Leu Ser Glu Ser Phe Glu Asn Gly Ile
                245                 250                 255

Pro Ala Ser Trp Lys Thr Ile Asp Ala Asp Gly Asp Gly His Gly Trp
            260                 265                 270

Lys Pro Gly Asn Ala Pro Gly Ile Ala Gly Tyr Asn Ser Asn Gly Cys
            275                 280                 285

Val Tyr Ser Glu Ser Phe Gly Leu Gly Gly Ile Gly Val Leu Thr Pro
            290                 295                 300

Asp Asn Tyr Leu Ile Thr Pro Ala Leu Asp Leu Pro Asn Gly Gly Lys
305                 310                 315                 320

Leu Thr Phe Trp Val Cys Ala Gln Asp Ala Asn Tyr Ala Ser Glu His
                325                 330                 335

Tyr Ala Val Tyr Ala Ser Ser Thr Gly Asn Asp Ala Ser Asn Phe Thr
            340                 345                 350

Asn Ala Leu Leu Glu Glu Thr Ile Thr Ala
            355                 360

<210> SEQ ID NO 36
<211> LENGTH: 231
<212> TYPE: PRT
<213> ORGANISM: Porphyromonas gingivalis

<400> SEQUENCE: 36

Phe Leu Leu Asp Ala Asp His Asn Thr Phe Gly Ser Val Ile Pro Ala
 1               5                  10                  15

Thr Gly Pro Leu Phe Thr Gly Thr Ala Ser Ser Asn Leu Tyr Ser Ala
                20                  25                  30

Asn Phe Glu Tyr Leu Ile Pro Ala Asn Ala Asp Pro Val Thr Thr
             35                  40                  45

Gln Asn Ile Ile Val Thr Gly Gln Gly Glu Val Ile Pro Gly Gly
         50                  55                  60

Val Tyr Asp Tyr Cys Ile Thr Asn Pro Glu Pro Ala Ser Gly Lys Met
```

```
                65                  70                  75                  80
Trp Ile Ala Gly Asp Gly Gly Asn Gln Pro Ala Arg Tyr Asp Asp Phe
                    85                  90                  95

Thr Phe Glu Ala Gly Lys Lys Tyr Thr Phe Thr Met Arg Arg Ala Gly
                    100                 105                 110

Met Gly Asp Gly Thr Asp Met Glu Val Glu Asp Asp Ser Pro Ala Ser
                    115                 120                 125

Tyr Thr Tyr Thr Val Tyr Arg Asp Gly Thr Lys Ile Lys Glu Gly Leu
                130                 135                 140

Thr Ala Thr Thr Phe Glu Glu Asp Gly Val Ala Ala Gly Asn His Glu
145                 150                 155                 160

Tyr Cys Val Glu Val Lys Tyr Thr Ala Gly Val Ser Pro Lys Val Cys
                    165                 170                 175

Lys Asp Val Thr Val Glu Gly Ser Asn Glu Phe Ala Pro Val Gln Asn
                    180                 185                 190

Leu Thr Gly Ser Ser Val Gly Gln Lys Val Thr Leu Lys Trp Asp Ala
                    195                 200                 205

Pro Asn Gly Thr Pro Asn Pro Asn Pro Asn Pro Asn Pro Asn Pro Gly
                    210                 215                 220

Thr Thr Leu Ser Glu Ser Phe
225                 230

<210> SEQ ID NO 37
<211> LENGTH: 306
<212> TYPE: PRT
<213> ORGANISM: Porphyromonas gingivalis

<400> SEQUENCE: 37

Trp Gly Asp Asn Thr Gly Tyr Gln Phe Leu Leu Asp Ala Asp His Asn
1               5                   10                  15

Thr Phe Gly Ser Val Ile Pro Ala Thr Gly Pro Leu Phe Thr Gly Thr
                20                  25                  30

Ala Ser Ser Asn Leu Tyr Ser Ala Asn Phe Glu Tyr Leu Ile Pro Ala
            35                  40                  45

Asn Ala Asp Pro Val Val Thr Thr Gln Asn Ile Ile Val Thr Gly Gln
        50                  55                  60

Gly Glu Val Val Ile Pro Gly Gly Val Tyr Asp Tyr Cys Ile Thr Asn
65                  70                  75                  80

Pro Glu Pro Ala Ser Gly Lys Met Trp Ile Ala Gly Asp Gly Gly Asn
                    85                  90                  95

Gln Pro Ala Arg Tyr Asp Asp Phe Thr Phe Glu Ala Gly Lys Lys Tyr
                100                 105                 110

Thr Phe Thr Met Arg Arg Ala Gly Met Gly Asp Gly Thr Asp Met Glu
            115                 120                 125

Val Glu Asp Asp Ser Pro Ala Ser Tyr Thr Tyr Thr Val Tyr Arg Asp
        130                 135                 140

Gly Thr Lys Ile Lys Glu Gly Leu Thr Ala Thr Thr Phe Glu Glu Asp
145                 150                 155                 160

Gly Val Ala Ala Gly Asn His Glu Tyr Cys Val Glu Val Lys Tyr Thr
                    165                 170                 175

Ala Gly Val Ser Pro Lys Val Cys Lys Asp Val Thr Val Glu Gly Ser
                180                 185                 190

Asn Glu Phe Ala Pro Val Gln Asn Leu Thr Gly Ser Ser Val Gly Gln
            195                 200                 205
```

```
Lys Val Thr Leu Lys Trp Asp Ala Pro Asn Gly Thr Pro Asn Pro Asn
            210                 215                 220

Pro Asn Pro Asn Pro Asn Pro Gly Thr Thr Leu Ser Glu Ser Phe Glu
225                 230                 235                 240

Asn Gly Ile Pro Ala Ser Trp Lys Thr Ile Asp Ala Asp Gly Asp Gly
                245                 250                 255

His Gly Trp Lys Pro Gly Asn Ala Pro Gly Ile Ala Gly Tyr Asn Ser
                260                 265                 270

Asn Gly Cys Val Tyr Ser Glu Ser Phe Gly Leu Gly Ile Gly Val
                275                 280                 285

Leu Thr Pro Asp Asn Tyr Leu Ile Thr Pro Ala Leu Asp Leu Pro Asn
    290                 295                 300

Gly Gly
305

<210> SEQ ID NO 38
<211> LENGTH: 362
<212> TYPE: PRT
<213> ORGANISM: Porphyromonas gingivalis

<400> SEQUENCE: 38

Ser Gly Gln Ala Glu Ile Val Leu Glu Ala His Asp Val Trp Asn Asp
1               5                   10                  15

Gly Ser Gly Tyr Gln Ile Leu Asp Ala Asp His Asp Gln Tyr Gly
            20                  25                  30

Gln Val Ile Pro Ser Asp Thr His Thr Leu Trp Pro Asn Cys Ser Val
                35                  40                  45

Pro Ala Asn Leu Phe Ala Pro Phe Glu Tyr Thr Val Pro Glu Asn Ala
50                  55                  60

Asp Pro Ser Cys Ser Pro Thr Asn Met Ile Met Asp Gly Thr Ala Ser
65                  70                  75                  80

Val Asn Ile Pro Ala Gly Thr Tyr Asp Phe Ala Ile Ala Ala Pro Gln
                85                  90                  95

Ala Asn Ala Lys Ile Trp Ile Ala Gly Gln Gly Pro Thr Lys Glu Asp
                100                 105                 110

Asp Tyr Val Phe Glu Ala Gly Lys Lys Tyr His Phe Leu Met Lys Lys
            115                 120                 125

Met Gly Ser Gly Asp Gly Thr Glu Leu Thr Ile Ser Glu Gly Gly Gly
        130                 135                 140

Ser Asp Tyr Thr Tyr Thr Val Tyr Arg Asp Gly Thr Lys Ile Lys Glu
145                 150                 155                 160

Gly Leu Thr Ala Thr Thr Phe Glu Glu Asp Gly Val Ala Thr Gly Asn
                165                 170                 175

His Glu Tyr Cys Val Glu Val Lys Tyr Thr Ala Gly Val Ser Pro Lys
            180                 185                 190

Val Cys Lys Asp Val Thr Val Glu Gly Ser Asn Glu Phe Ala Pro Val
        195                 200                 205

Gln Asn Leu Thr Gly Ser Ala Val Gly Gln Lys Val Thr Leu Lys Trp
    210                 215                 220

Asp Ala Pro Asn Gly Thr Pro Asn Pro Asn Pro Asn Pro Asn Pro Asn
225                 230                 235                 240

Pro Asn Pro Gly Thr Thr Thr Leu Ser Glu Ser Phe Glu Asn Gly Ile
                245                 250                 255

Pro Ala Ser Trp Lys Thr Ile Asp Ala Asp Gly Asp Gly His Gly Trp
            260                 265                 270
```

```
Lys Pro Gly Asn Ala Pro Gly Ile Ala Gly Tyr Asn Ser Asn Gly Cys
            275                 280                 285

Val Tyr Ser Glu Ser Phe Gly Leu Gly Gly Ile Gly Val Leu Thr Pro
        290                 295                 300

Asp Asn Tyr Leu Ile Thr Pro Ala Leu Asp Leu Pro Asn Gly Gly Lys
305                 310                 315                 320

Leu Thr Phe Trp Val Cys Ala Gln Asp Ala Asn Tyr Ala Ser Glu His
                325                 330                 335

Tyr Ala Val Tyr Ala Ser Ser Thr Gly Asn Asp Ala Ser Asn Phe Thr
            340                 345                 350

Asn Ala Leu Leu Glu Glu Thr Ile Thr Ala
            355                 360

<210> SEQ ID NO 39
<211> LENGTH: 141
<212> TYPE: PRT
<213> ORGANISM: Porphyromonas gingivalis

<400> SEQUENCE: 39

Asp Asp Tyr Val Phe Glu Ala Gly Lys Lys Tyr His Phe Leu Met Lys
1               5                   10                  15

Lys Met Gly Ser Gly Asp Gly Thr Glu Leu Thr Ile Ser Glu Gly Gly
            20                  25                  30

Gly Ser Asp Tyr Thr Tyr Thr Val Tyr Arg Asp Gly Thr Lys Ile Lys
        35                  40                  45

Glu Gly Leu Thr Ala Thr Thr Phe Glu Glu Asp Gly Val Ala Thr Gly
    50                  55                  60

Asn His Glu Tyr Cys Val Glu Val Lys Tyr Thr Ala Gly Val Ser Pro
65                  70                  75                  80

Lys Val Cys Lys Asp Val Thr Val Glu Gly Ser Asn Glu Phe Ala Pro
                85                  90                  95

Val Gln Asn Leu Thr Gly Ser Ala Val Gly Gln Lys Val Thr Leu Lys
            100                 105                 110

Trp Asp Ala Pro Asn Gly Thr Pro Asn Pro Asn Pro Asn Pro Asn Pro
        115                 120                 125

Asn Pro Asn Pro Gly Thr Thr Leu Ser Glu Ser Phe
    130                 135                 140

<210> SEQ ID NO 40
<211> LENGTH: 119
<212> TYPE: PRT
<213> ORGANISM: Porphyromonas gingivalis

<400> SEQUENCE: 40

Ala Asp Phe Thr Glu Thr Phe Glu Ser Ser Thr His Gly Glu Ala Pro
1               5                   10                  15

Ala Glu Trp Thr Thr Ile Asp Ala Asp Gly Asp Gly Gln Gly Trp Leu
            20                  25                  30

Cys Leu Ser Ser Gly Gln Leu Asp Trp Leu Thr Ala His Gly Gly Ser
        35                  40                  45

Asn Val Val Ser Ser Phe Ser Trp Asn Gly Met Ala Leu Asn Pro Asp
    50                  55                  60

Asn Tyr Leu Ile Ser Lys Asp Val Thr Gly Ala Thr Lys Val Lys Tyr
65                  70                  75                  80

Tyr Tyr Ala Val Asn Asp Gly Phe Pro Gly Asp His Tyr Ala Val Met
                85                  90                  95
```

Ile Ser Lys Thr Gly Thr Asn Ala Gly Asp Phe Thr Val Val Phe Glu
                100                 105                 110

Glu Thr Pro Asn Gly Ile Asn
        115

<210> SEQ ID NO 41
<211> LENGTH: 133
<212> TYPE: PRT
<213> ORGANISM: Porphyromonas gingivalis

<400> SEQUENCE: 41

Pro Gln Ser Val Trp Ile Glu Arg Thr Val Asp Leu Pro Ala Gly Thr
1               5                   10                  15

Lys Tyr Val Ala Phe Arg His Tyr Asn Cys Ser Asp Leu Asn Tyr Ile
            20                  25                  30

Leu Leu Asp Asp Ile Gln Phe Thr Met Gly Gly Ser Pro Thr Pro Thr
        35                  40                  45

Asp Tyr Thr Tyr Thr Val Tyr Arg Asp Gly Thr Lys Ile Lys Glu Gly
    50                  55                  60

Leu Thr Glu Thr Thr Phe Glu Glu Asp Gly Val Ala Thr Gly Asn His
65                  70                  75                  80

Glu Tyr Cys Val Glu Val Lys Tyr Thr Ala Gly Val Ser Pro Lys Lys
                85                  90                  95

Cys Val Asn Val Thr Val Asn Ser Thr Gln Phe Asn Pro Val Gln Asn
            100                 105                 110

Leu Thr Ala Glu Gln Ala Pro Asn Ser Met Asp Ala Ile Leu Lys Trp
        115                 120                 125

Asn Ala Pro Ala Ser
    130

<210> SEQ ID NO 42
<211> LENGTH: 120
<212> TYPE: PRT
<213> ORGANISM: Porphyromonas gingivalis

<400> SEQUENCE: 42

Ala Glu Val Leu Asn Glu Asp Phe Glu Asn Gly Ile Pro Ala Ser Trp
1               5                   10                  15

Lys Thr Ile Asp Ala Asp Gly Asp Gly Asn Asn Trp Thr Thr Thr Pro
            20                  25                  30

Pro Pro Gly Gly Ser Ser Phe Ala Gly His Asn Ser Ala Ile Cys Val
        35                  40                  45

Ser Ser Ala Ser Tyr Ile Asn Phe Glu Gly Pro Gln Asn Pro Asp Asn
    50                  55                  60

Tyr Leu Val Thr Pro Glu Leu Ser Leu Pro Gly Gly Gly Thr Leu Thr
65                  70                  75                  80

Phe Trp Val Cys Ala Gln Asp Ala Asn Tyr Ala Ser Glu His Tyr Ala
                85                  90                  95

Val Tyr Ala Ser Ser Thr Gly Asn Asp Ala Ser Asn Phe Ala Asn Ala
            100                 105                 110

Leu Leu Glu Glu Val Leu Thr Ala
        115                 120

<210> SEQ ID NO 43
<211> LENGTH: 185
<212> TYPE: PRT
<213> ORGANISM: Porphyromonas gingivalis

<400> SEQUENCE: 43

Thr Val Val Thr Ala Pro Glu Ala Ile Arg Gly Thr Arg Ala Gln Gly
1               5                   10                  15

Thr Trp Tyr Gln Lys Thr Val Gln Leu Pro Ala Gly Thr Lys Tyr Val
            20                  25                  30

Ala Phe Arg His Phe Gly Cys Thr Asp Phe Phe Trp Ile Asn Leu Asp
        35                  40                  45

Asp Val Val Ile Thr Ser Gly Asn Ala Pro Ser Tyr Thr Tyr Thr Ile
    50                  55                  60

Tyr Arg Asn Asn Thr Gln Ile Ala Ser Gly Val Thr Glu Thr Thr Tyr
65                  70                  75                  80

Arg Asp Pro Asp Leu Ala Thr Gly Phe Tyr Thr Tyr Gly Val Lys Val
                85                  90                  95

Val Tyr Pro Asn Gly Glu Ser Ala Ile Glu Thr Ala Thr Leu Asn Ile
            100                 105                 110

Thr Ser Leu Ala Asp Val Thr Ala Gln Lys Pro Tyr Thr Leu Thr Val
        115                 120                 125

Val Gly Lys Thr Ile Thr Val Thr Cys Gln Gly Glu Ala Met Ile Tyr
    130                 135                 140

Asp Met Asn Gly Arg Arg Leu Ala Ala Gly Arg Asn Thr Val Val Tyr
145                 150                 155                 160

Thr Ala Gln Gly Gly His Tyr Ala Val Met Val Val Asp Gly Lys
                165                 170                 175

Ser Tyr Val Glu Lys Leu Ala Val Lys
            180                 185

<210> SEQ ID NO 44
<211> LENGTH: 119
<212> TYPE: PRT
<213> ORGANISM: Porphyromonas gingivalis

<400> SEQUENCE: 44

Ala Asp Phe Thr Glu Thr Phe Glu Ser Ser Thr His Gly Glu Ala Pro
1               5                   10                  15

Ala Glu Trp Thr Thr Ile Asp Ala Asp Gly Asp Gly Gln Gly Trp Leu
            20                  25                  30

Cys Leu Ser Ser Gly Gln Leu Asp Trp Leu Thr Ala His Gly Gly Thr
        35                  40                  45

Asn Val Val Ser Ser Phe Ser Trp Asn Gly Met Ala Leu Asn Pro Asp
    50                  55                  60

Asn Tyr Leu Ile Ser Lys Asp Val Thr Gly Ala Thr Lys Val Lys Tyr
65                  70                  75                  80

Tyr Tyr Ala Val Asn Asp Gly Phe Pro Gly Asp His Tyr Ala Val Met
                85                  90                  95

Ile Ser Lys Thr Gly Thr Asn Ala Gly Asp Phe Thr Val Phe Glu
            100                 105                 110

Glu Thr Pro Asn Gly Ile Asn
        115

<210> SEQ ID NO 45
<211> LENGTH: 131
<212> TYPE: PRT
<213> ORGANISM: Porphyromonas gingivalis

<400> SEQUENCE: 45

```
Pro Gln Ser Val Trp Ile Glu Arg Thr Val Asp Leu Pro Ala Gly Thr
1               5                   10                  15

Lys Tyr Val Ala Phe Arg His Tyr Asn Cys Ser Asp Leu Asn Tyr Ile
            20                  25                  30

Leu Leu Asp Asp Ile Gln Phe Thr Met Gly Gly Ser Pro Thr Pro Thr
        35                  40                  45

Asp Tyr Thr Tyr Thr Val Tyr Arg Asp Gly Thr Lys Ile Lys Glu Gly
    50                  55                  60

Leu Thr Glu Thr Thr Phe Glu Glu Asp Gly Val Ala Thr Gly Asn His
65                  70                  75                  80

Glu Tyr Cys Val Glu Val Lys Tyr Thr Ala Gly Val Ser Pro Lys Lys
            85                  90                  95

Cys Val Asn Val Thr Val Asn Ser Thr Gln Phe Asn Pro Val Lys Asn
            100                 105                 110

Leu Lys Ala Gln Pro Asp Gly Gly Asp Val Val Leu Lys Trp Glu Ala
            115                 120                 125

Pro Ser Ala
    130

<210> SEQ ID NO 46
<211> LENGTH: 275
<212> TYPE: PRT
<213> ORGANISM: Porphyromonas gingivalis

<400> SEQUENCE: 46

Ala Asn Glu Ala Lys Val Val Leu Ala Ala Asp Asn Val Trp Gly Asp
1               5                   10                  15

Asn Thr Gly Tyr Gln Phe Leu Leu Asp Ala Asp His Asn Thr Phe Gly
            20                  25                  30

Ser Val Ile Pro Ala Thr Gly Pro Leu Phe Thr Gly Thr Ala Ser Ser
            35                  40                  45

Asp Leu Tyr Ser Ala Asn Phe Glu Ser Leu Ile Pro Ala Asn Ala Asp
    50                  55                  60

Pro Val Thr Thr Gln Asn Ile Ile Val Thr Gly Gln Gly Glu Val
65                  70                  75                  80

Val Ile Pro Gly Gly Val Tyr Asp Tyr Cys Ile Thr Asn Pro Glu Pro
            85                  90                  95

Ala Ser Gly Lys Met Trp Ile Ala Gly Asp Gly Asn Gln Pro Ala
            100                 105                 110

Arg Tyr Asp Asp Phe Thr Phe Glu Ala Gly Lys Lys Tyr Thr Phe Thr
            115                 120                 125

Met Arg Arg Ala Gly Met Gly Asp Gly Thr Asp Met Glu Val Glu Asp
            130                 135                 140

Asp Ser Pro Ala Ser Tyr Thr Tyr Thr Val Tyr Arg Asp Gly Thr Lys
145                 150                 155                 160

Ile Lys Glu Gly Leu Thr Glu Thr Thr Tyr Arg Asp Ala Gly Met Ser
            165                 170                 175

Ala Gln Ser His Glu Tyr Cys Val Glu Val Lys Tyr Thr Ala Gly Val
            180                 185                 190

Ser Pro Lys Val Cys Val Asp Tyr Ile Pro Asp Gly Val Ala Asp Val
            195                 200                 205

Thr Ala Gln Lys Pro Tyr Thr Leu Thr Val Val Gly Lys Thr Ile Thr
            210                 215                 220

Val Thr Cys Gln Gly Glu Ala Met Ile Tyr Asp Met Asn Gly Arg Arg
225                 230                 235                 240
```

```
Leu Ala Ala Gly Arg Asn Thr Val Val Tyr Thr Ala Gln Gly Gly Tyr
            245                 250                 255

Tyr Ala Val Met Val Val Val Asp Gly Lys Ser Tyr Val Glu Lys Leu
            260                 265                 270

Ala Ile Lys
        275

<210> SEQ ID NO 47
<211> LENGTH: 49
<212> TYPE: DNA
<213> ORGANISM: Porphyromonas gingivalis

<400> SEQUENCE: 47
gaccatggct catcaccatc accatcacaa taccggagtc agctttgca                49

<210> SEQ ID NO 48
<211> LENGTH: 36
<212> TYPE: DNA
<213> ORGANISM: Porphyromonas gingivalis

<400> SEQUENCE: 48
gactcgagtt atttgtcctt attagtgagt gctttc                              36

<210> SEQ ID NO 49
<211> LENGTH: 31
<212> TYPE: DNA
<213> ORGANISM: Porphyromonas gingivalis

<400> SEQUENCE: 49
gaccatggct tggggagaca atacgggtta c                                   31

<210> SEQ ID NO 50
<211> LENGTH: 27
<212> TYPE: DNA
<213> ORGANISM: Porphyromonas gingivalis

<400> SEQUENCE: 50
gactcgagac ctccgttagg caaatcc                                        27

<210> SEQ ID NO 51
<211> LENGTH: 41
<212> TYPE: DNA
<213> ORGANISM: Porphyromonas gingivalis

<400> SEQUENCE: 51
ccgtattgtc tccccatttg tccttattag tgagtgcttt c                        41

<210> SEQ ID NO 52
<211> LENGTH: 37
<212> TYPE: DNA
<213> ORGANISM: Porphyromonas gingivalis

<400> SEQUENCE: 52
cactaataag gacaaatggg gagacaatac gggttac                             37

<210> SEQ ID NO 53
<211> LENGTH: 51
<212> TYPE: DNA
<213> ORGANISM: Porphyromonas gingivalis

<400> SEQUENCE: 53
catggatctg agaccgcatg gctgatcca cttttcttgt tggatgccga t              51
```

<210> SEQ ID NO 54
<211> LENGTH: 62
<212> TYPE: DNA
<213> ORGANISM: Porphyromonas gingivalis

<400> SEQUENCE: 54
ccatggcttt gaataccgga gtcagctttg caaactatac agcgcatgga tctgagaccg    60
ca                                                                   62

<210> SEQ ID NO 55
<211> LENGTH: 25
<212> TYPE: DNA
<213> ORGANISM: Porphyromonas gingivalis

<400> SEQUENCE: 55
ctcgaggaat gattcggaaa gtgtt                                          25

<210> SEQ ID NO 56
<211> LENGTH: 53
<212> TYPE: DNA
<213> ORGANISM: Porphyromonas gingivalis

<400> SEQUENCE: 56
ccatggctga ttatagctgg aattcccagg tagtcagctt tgcaaactat aca           53

<210> SEQ ID NO 57
<211> LENGTH: 52
<212> TYPE: DNA
<213> ORGANISM: Porphyromonas gingivalis

<400> SEQUENCE: 57
ctttgcaaac tatacagcgc atggatctga ccgcatgg gctgatccac tt              52

<210> SEQ ID NO 58
<211> LENGTH: 52
<212> TYPE: DNA
<213> ORGANISM: Porphyromonas gingivalis

<400> SEQUENCE: 58
atgggctgat ccacttctga attcttattg gggcgagatc ggcaatatta cc            52

<210> SEQ ID NO 59
<211> LENGTH: 52
<212> TYPE: DNA
<213> ORGANISM: Porphyromonas gingivalis

<400> SEQUENCE: 59
gatcggcaat attacccata ttggtgctca ttacgcttgg ggagacaata cg            52

<210> SEQ ID NO 60
<211> LENGTH: 52
<212> TYPE: DNA
<213> ORGANISM: Porphyromonas gingivalis

<400> SEQUENCE: 60
ctcgagacct ccgttaggca aatccaatgc cggtgttatc agatagttgt ca            52

<210> SEQ ID NO 61
<211> LENGTH: 1706
<212> TYPE: PRT
<213> ORGANISM: Porphyromonas gingivalis

<400> SEQUENCE: 61

```
Met Lys Asn Leu Asn Lys Phe Val Ser Ile Ala Leu Cys Ser Ser Leu
1               5                   10                  15
Leu Gly Gly Met Ala Phe Ala Gln Gln Thr Glu Leu Gly Arg Asn Pro
            20                  25                  30
Asn Val Arg Leu Leu Glu Ser Thr Gln Gln Ser Val Thr Lys Val Gln
        35                  40                  45
Phe Arg Met Asp Asn Leu Lys Phe Thr Glu Val Gln Thr Pro Lys Gly
    50                  55                  60
Ile Gly Gln Val Pro Thr Tyr Thr Glu Gly Val Asn Leu Ser Glu Lys
65                  70                  75                  80
Gly Met Pro Thr Leu Pro Ile Leu Ser Arg Ser Leu Ala Val Ser Asp
                85                  90                  95
Thr Arg Glu Met Lys Val Glu Val Val Ser Ser Lys Phe Ile Glu Lys
            100                 105                 110
Lys Asn Val Leu Ile Ala Pro Ser Lys Gly Met Ile Met Arg Asn Glu
        115                 120                 125
Asp Pro Lys Lys Ile Pro Tyr Val Tyr Gly Lys Thr Tyr Ser Gln Asn
    130                 135                 140
Lys Phe Phe Pro Gly Glu Ile Ala Thr Leu Asp Asp Pro Phe Ile Leu
145                 150                 155                 160
Arg Asp Val Arg Gly Gln Val Val Asn Phe Ala Pro Leu Gln Tyr Asn
                165                 170                 175
Pro Val Thr Lys Thr Leu Arg Ile Tyr Thr Glu Ile Thr Val Ala Val
            180                 185                 190
Ser Glu Thr Ser Glu Gln Gly Lys Asn Ile Leu Asn Lys Lys Gly Thr
        195                 200                 205
Phe Ala Gly Phe Glu Asp Thr Tyr Lys Arg Met Phe Met Asn Tyr Glu
    210                 215                 220
Pro Gly Arg Tyr Thr Pro Val Glu Glu Lys Gln Asn Gly Arg Met Ile
225                 230                 235                 240
Val Ile Val Ala Lys Lys Tyr Glu Gly Asp Ile Lys Asp Phe Val Asp
                245                 250                 255
Trp Lys Asn Gln Arg Gly Leu Arg Thr Glu Val Lys Val Ala Glu Asp
            260                 265                 270
Ile Ala Ser Pro Val Thr Ala Asn Ala Ile Gln Gln Phe Val Lys Gln
        275                 280                 285
Glu Tyr Glu Lys Glu Gly Asn Asp Leu Thr Tyr Val Leu Leu Ile Gly
    290                 295                 300
Asp His Lys Asp Ile Pro Ala Lys Ile Thr Pro Gly Ile Lys Ser Asp
305                 310                 315                 320
Gln Val Tyr Gly Gln Ile Val Gly Asn Asp His Tyr Asn Glu Val Phe
                325                 330                 335
Ile Gly Arg Phe Ser Cys Glu Ser Lys Glu Asp Leu Lys Thr Gln Ile
            340                 345                 350
Asp Arg Thr Ile His Tyr Glu Arg Asn Ile Thr Thr Glu Asp Lys Trp
        355                 360                 365
Leu Gly Gln Ala Leu Cys Ile Ala Ser Ala Glu Gly Gly Pro Ser Ala
    370                 375                 380
Asp Asn Gly Glu Ser Asp Ile Gln His Glu Asn Val Ile Ala Asn Leu
385                 390                 395                 400
Leu Thr Gln Tyr Gly Tyr Thr Lys Ile Ile Lys Cys Tyr Asp Pro Gly
                405                 410                 415
```

```
Val Thr Pro Lys Asn Ile Ile Asp Ala Phe Asn Gly Gly Ile Ser Leu
            420                 425                 430

Ala Asn Tyr Thr Gly His Gly Ser Glu Thr Ala Trp Gly Thr Ser His
            435                 440                 445

Phe Gly Thr Thr His Val Lys Gln Leu Thr Asn Ser Asn Gln Leu Pro
            450                 455                 460

Phe Ile Phe Asp Val Ala Cys Val Asn Gly Asp Phe Leu Phe Ser Met
465                 470                 475                 480

Pro Cys Phe Ala Glu Ala Leu Met Arg Ala Gln Lys Asp Gly Lys Pro
                485                 490                 495

Thr Gly Thr Val Ala Ile Ile Ala Ser Thr Ile Asn Gln Ser Trp Ala
            500                 505                 510

Ser Pro Met Arg Gly Gln Asp Glu Met Asn Glu Ile Leu Cys Glu Lys
            515                 520                 525

His Pro Asn Asn Ile Lys Arg Thr Phe Gly Gly Val Thr Met Asn Gly
            530                 535                 540

Met Phe Ala Met Val Glu Lys Tyr Lys Lys Asp Gly Glu Lys Met Leu
545                 550                 555                 560

Asp Thr Trp Thr Val Phe Gly Asp Pro Ser Leu Leu Val Arg Thr Leu
                565                 570                 575

Val Pro Thr Lys Met Gln Val Thr Ala Pro Ala Gln Ile Asn Leu Thr
            580                 585                 590

Asp Ala Ser Val Asn Val Ser Cys Asp Tyr Asn Gly Ala Ile Ala Thr
            595                 600                 605

Ile Ser Ala Asn Gly Lys Met Phe Gly Ser Ala Val Val Glu Asn Gly
            610                 615                 620

Thr Ala Thr Ile Asn Leu Thr Gly Leu Thr Asn Glu Ser Thr Leu Thr
625                 630                 635                 640

Leu Thr Val Val Gly Tyr Asn Lys Glu Thr Val Ile Lys Thr Ile Asn
                645                 650                 655

Thr Asn Gly Glu Pro Asn Pro Tyr Gln Pro Val Ser Asn Leu Thr Ala
            660                 665                 670

Thr Thr Gln Gly Gln Lys Val Thr Leu Lys Trp Asp Ala Pro Ser Thr
            675                 680                 685

Lys Thr Asn Ala Thr Thr Asn Thr Ala Arg Ser Val Asp Gly Ile Arg
            690                 695                 700

Glu Leu Val Leu Leu Ser Val Ser Asp Ala Pro Glu Leu Leu Arg Ser
705                 710                 715                 720

Gly Gln Ala Glu Ile Val Leu Glu Ala His Asp Val Trp Asn Asp Gly
                725                 730                 735

Ser Gly Tyr Gln Ile Leu Leu Asp Ala Asp His Asp Gln Tyr Gly Gln
            740                 745                 750

Val Ile Pro Ser Asp Thr His Thr Leu Trp Pro Asn Cys Ser Val Pro
            755                 760                 765

Ala Asn Leu Phe Ala Pro Phe Glu Tyr Thr Val Pro Glu Asn Ala Asp
            770                 775                 780

Pro Ser Cys Ser Pro Thr Asn Met Ile Met Asp Gly Thr Ala Ser Val
785                 790                 795                 800

Asn Ile Pro Ala Gly Thr Tyr Asp Phe Ala Ile Ala Ala Pro Gln Ala
                805                 810                 815

Asn Ala Lys Ile Trp Ile Ala Gly Gln Gly Pro Thr Lys Glu Asp Asp
            820                 825                 830
```

Tyr Val Phe Glu Ala Gly Lys Lys Tyr His Phe Leu Met Lys Lys Met
            835                 840                 845

Gly Ser Gly Asp Gly Thr Glu Leu Thr Ile Ser Glu Gly Gly Gly Ser
850                 855                 860

Asp Tyr Thr Tyr Thr Val Tyr Arg Asp Gly Thr Lys Ile Lys Glu Gly
865                 870                 875                 880

Leu Thr Ala Thr Thr Phe Glu Glu Asp Gly Val Ala Thr Gly Asn His
                885                 890                 895

Glu Tyr Cys Val Glu Val Lys Tyr Thr Ala Gly Val Ser Pro Lys Val
            900                 905                 910

Cys Lys Asp Val Thr Val Glu Gly Ser Asn Glu Phe Ala Pro Val Gln
        915                 920                 925

Asn Leu Thr Gly Ser Ala Val Gly Gln Lys Val Thr Leu Lys Trp Asp
    930                 935                 940

Ala Pro Asn Gly Thr Pro Asn Pro Asn Pro Asn Pro Asn Pro Asn Pro
945                 950                 955                 960

Asn Pro Gly Thr Thr Thr Leu Ser Glu Ser Phe Glu Asn Gly Ile Pro
                965                 970                 975

Ala Ser Trp Lys Thr Ile Asp Ala Asp Gly Asp Gly His Gly Trp Lys
            980                 985                 990

Pro Gly Asn Ala Pro Gly Ile Ala Gly Tyr Asn Ser Asn Gly Cys Val
        995                 1000                1005

Tyr Ser Glu Ser Phe Gly Leu Gly Gly Ile Gly Val Leu Thr Pro
    1010                1015                1020

Asp Asn Tyr Leu Ile Thr Pro Ala Leu Asp Leu Pro Asn Gly Gly
    1025                1030                1035

Lys Leu Thr Phe Trp Val Cys Ala Gln Asp Ala Asn Tyr Ala Ser
    1040                1045                1050

Glu His Tyr Ala Val Tyr Ala Ser Ser Thr Gly Asn Asp Ala Ser
    1055                1060                1065

Asn Phe Thr Asn Ala Leu Leu Glu Glu Thr Ile Thr Ala Lys Gly
    1070                1075                1080

Val Arg Ser Pro Glu Ala Met Arg Gly Arg Ile Gln Gly Thr Trp
    1085                1090                1095

Arg Gln Lys Thr Val Asp Leu Pro Ala Gly Thr Lys Tyr Val Ala
    1100                1105                1110

Phe Arg His Phe Gln Ser Thr Asp Met Phe Tyr Ile Asp Leu Asp
    1115                1120                1125

Glu Val Glu Ile Lys Ala Asn Gly Lys Arg Ala Asp Phe Thr Glu
    1130                1135                1140

Thr Phe Glu Ser Ser Thr His Gly Glu Ala Pro Ala Glu Trp Thr
    1145                1150                1155

Thr Ile Asp Ala Asp Gly Asp Gly Gln Gly Trp Leu Cys Leu Ser
    1160                1165                1170

Ser Gly Gln Leu Asp Trp Leu Thr Ala His Gly Gly Thr Asn Val
    1175                1180                1185

Val Ser Ser Phe Ser Trp Asn Gly Met Ala Leu Asn Pro Asp Asn
    1190                1195                1200

Tyr Leu Ile Ser Lys Asp Val Thr Gly Ala Thr Lys Val Lys Tyr
    1205                1210                1215

Tyr Tyr Ala Val Asn Asp Gly Phe Pro Gly Asp His Tyr Ala Val
    1220                1225                1230

Met Ile Ser Lys Thr Gly Thr Asn Ala Gly Asp Phe Thr Val Val

```
                1235                1240                1245

Phe Glu Glu Thr Pro Asn Gly Ile Asn Lys Gly Gly Ala Arg Phe
    1250                1255                1260

Gly Leu Ser Thr Glu Ala Asp Gly Ala Lys Pro Gln Ser Val Trp
    1265                1270                1275

Ile Glu Arg Thr Val Asp Leu Pro Ala Gly Thr Lys Tyr Val Ala
    1280                1285                1290

Phe Arg His Tyr Asn Cys Ser Asp Leu Asn Tyr Ile Leu Leu Asp
    1295                1300                1305

Asp Ile Gln Phe Thr Met Gly Gly Ser Pro Thr Pro Thr Asp Tyr
    1310                1315                1320

Thr Tyr Thr Val Tyr Arg Asp Gly Thr Lys Ile Lys Glu Gly Leu
    1325                1330                1335

Thr Glu Thr Thr Phe Glu Glu Asp Gly Val Ala Thr Gly Asn His
    1340                1345                1350

Glu Tyr Cys Val Glu Val Lys Tyr Thr Ala Gly Val Ser Pro Lys
    1355                1360                1365

Lys Cys Val Asn Val Thr Val Asn Ser Thr Gln Phe Asn Pro Val
    1370                1375                1380

Lys Asn Leu Lys Ala Gln Pro Asp Gly Asp Val Val Leu Lys
    1385                1390                1395

Trp Glu Ala Pro Ser Ala Lys Lys Thr Glu Gly Ser Arg Glu Val
    1400                1405                1410

Lys Arg Ile Gly Asp Gly Leu Phe Val Thr Ile Glu Pro Ala Asn
    1415                1420                1425

Asp Val Arg Ala Asn Glu Ala Lys Val Val Leu Ala Ala Asp Asn
    1430                1435                1440

Val Trp Gly Asp Asn Thr Gly Tyr Gln Phe Leu Leu Asp Ala Asp
    1445                1450                1455

His Asn Thr Phe Gly Ser Val Ile Pro Ala Thr Gly Pro Leu Phe
    1460                1465                1470

Thr Gly Thr Ala Ser Ser Asp Leu Tyr Ser Ala Asn Phe Glu Ser
    1475                1480                1485

Leu Ile Pro Ala Asn Ala Asp Pro Val Val Thr Thr Gln Asn Ile
    1490                1495                1500

Ile Val Thr Gly Gln Gly Glu Val Val Ile Pro Gly Gly Val Tyr
    1505                1510                1515

Asp Tyr Cys Ile Thr Asn Pro Glu Pro Ala Ser Gly Lys Met Trp
    1520                1525                1530

Ile Ala Gly Asp Gly Gly Asn Gln Pro Ala Arg Tyr Asp Asp Phe
    1535                1540                1545

Thr Phe Glu Ala Gly Lys Lys Tyr Thr Phe Thr Met Arg Arg Ala
    1550                1555                1560

Gly Met Gly Asp Gly Thr Asp Met Glu Val Glu Asp Asp Ser Pro
    1565                1570                1575

Ala Ser Tyr Thr Tyr Thr Val Tyr Arg Asp Gly Thr Lys Ile Lys
    1580                1585                1590

Glu Gly Leu Thr Glu Thr Thr Tyr Arg Asp Ala Gly Met Ser Ala
    1595                1600                1605

Gln Ser His Glu Tyr Cys Val Glu Val Lys Tyr Thr Ala Gly Val
    1610                1615                1620

Ser Pro Lys Val Cys Val Asp Tyr Ile Pro Asp Gly Val Ala Asp
    1625                1630                1635
```

Val Thr Ala Gln Lys Pro Tyr Thr Leu Thr Val Val Gly Lys Thr
1640            1645                1650

Ile Thr Val Thr Cys Gln Gly Glu Ala Met Ile Tyr Asp Met Asn
    1655            1660                1665

Gly Arg Arg Leu Ala Ala Gly Arg Asn Thr Val Val Tyr Thr Ala
    1670            1675                1680

Gln Gly Gly Tyr Tyr Ala Val Met Val Val Val Asp Gly Lys Ser
    1685            1690                1695

Tyr Val Glu Lys Leu Ala Ile Lys
    1700            1705

<210> SEQ ID NO 62
<211> LENGTH: 1732
<212> TYPE: PRT
<213> ORGANISM: Porphyromonas gingivalis

<400> SEQUENCE: 62

Met Arg Lys Leu Leu Leu Ile Ala Ala Ser Leu Leu Gly Val Gly
1               5                   10                  15

Leu Tyr Ala Gln Ser Ala Lys Ile Lys Leu Asp Ala Pro Thr Thr Arg
            20                  25                  30

Thr Thr Cys Thr Asn Asn Ser Phe Lys Gln Phe Asp Ala Ser Phe Ser
        35                  40                  45

Phe Asn Glu Val Glu Leu Thr Lys Val Glu Thr Lys Gly Gly Thr Phe
50                  55                  60

Ala Ser Val Ser Ile Pro Gly Ala Phe Pro Thr Gly Glu Val Gly Ser
65                  70                  75                  80

Pro Glu Val Pro Ala Val Arg Lys Leu Ile Ala Val Pro Val Gly Ala
                85                  90                  95

Thr Pro Val Val Arg Val Lys Ser Phe Thr Glu Gln Val Tyr Ser Leu
            100                 105                 110

Asn Gln Tyr Gly Ser Glu Lys Leu Met Pro His Gln Pro Ser Met Ser
            115                 120                 125

Lys Ser Asp Asp Pro Glu Lys Val Pro Phe Val Tyr Asn Ala Ala Ala
130                 135                 140

Tyr Ala Arg Lys Gly Phe Val Gly Gln Glu Leu Thr Gln Val Glu Met
145                 150                 155                 160

Leu Gly Thr Met Arg Gly Val Arg Ile Ala Ala Leu Thr Ile Asn Pro
                165                 170                 175

Val Gln Tyr Asp Val Val Ala Asn Gln Leu Lys Val Arg Asn Asn Ile
            180                 185                 190

Glu Ile Glu Val Ser Phe Gln Gly Ala Asp Gly Val Ala Thr Gln Arg
            195                 200                 205

Leu Tyr Asp Ala Ser Phe Ser Pro Tyr Phe Glu Thr Ala Tyr Lys Gln
        210                 215                 220

Leu Phe Asn Arg Asp Val Tyr Thr Asp His Gly Asp Leu Tyr Asn Thr
225                 230                 235                 240

Pro Val Arg Met Leu Val Val Ala Gly Ala Lys Phe Lys Glu Ala Leu
                245                 250                 255

Lys Pro Trp Leu Thr Trp Lys Ala Gln Lys Gly Phe Tyr Leu Asp Val
                260                 265                 270

His Tyr Thr Asp Glu Ala Glu Val Gly Thr Thr Asn Ala Ser Ile Lys
            275                 280                 285

Ala Phe Ile His Lys Lys Tyr Asn Asp Gly Leu Ala Ala Ser Ala Ala

-continued

```
                290                 295                 300
Pro Val Phe Leu Ala Leu Val Gly Asp Thr Asp Val Ile Ser Gly Glu
305                 310                 315                 320

Lys Gly Lys Lys Thr Lys Lys Val Thr Asp Leu Tyr Tyr Ser Ala Val
                325                 330                 335

Asp Gly Asp Tyr Phe Pro Glu Met Tyr Thr Phe Arg Met Ser Ala Ser
                340                 345                 350

Ser Pro Glu Glu Leu Thr Asn Ile Ile Asp Lys Val Leu Met Tyr Glu
            355                 360                 365

Lys Ala Thr Met Pro Asp Lys Ser Tyr Leu Glu Lys Val Leu Leu Ile
            370                 375                 380

Ala Gly Ala Asp Tyr Ser Trp Asn Ser Gln Val Gly Gln Pro Thr Ile
385                 390                 395                 400

Lys Tyr Gly Met Gln Tyr Tyr Asn Gln His Gly Tyr Thr Asp
                405                 410                 415

Val Tyr Asn Tyr Leu Lys Ala Pro Tyr Thr Gly Cys Tyr Ser His Leu
                420                 425                 430

Asn Thr Gly Val Ser Phe Ala Asn Tyr Thr Ala His Gly Ser Glu Thr
            435                 440                 445

Ala Trp Ala Asp Pro Leu Leu Thr Thr Ser Gln Leu Lys Ala Leu Thr
            450                 455                 460

Asn Lys Asp Lys Tyr Phe Leu Ala Ile Gly Asn Cys Cys Ile Thr Ala
465                 470                 475                 480

Gln Phe Asp Tyr Val Gln Pro Cys Phe Gly Glu Val Ile Thr Arg Val
                485                 490                 495

Lys Glu Lys Gly Ala Tyr Ala Tyr Ile Gly Ser Ser Pro Asn Ser Tyr
                500                 505                 510

Trp Gly Glu Asp Tyr Tyr Trp Ser Val Gly Ala Asn Ala Val Phe Gly
            515                 520                 525

Val Gln Pro Thr Phe Glu Gly Thr Ser Met Gly Ser Tyr Asp Ala Thr
            530                 535                 540

Phe Leu Glu Asp Ser Tyr Asn Thr Val Asn Ser Ile Met Trp Ala Gly
545                 550                 555                 560

Asn Leu Ala Ala Thr His Ala Gly Asn Ile Gly Asn Ile Thr His Ile
                565                 570                 575

Gly Ala His Tyr Tyr Trp Glu Tyr His Val Leu Gly Asp Gly Ser
                580                 585                 590

Val Met Pro Tyr Arg Ala Met Pro Lys Thr Asn Thr Tyr Thr Leu Pro
            595                 600                 605

Ala Ser Leu Pro Gln Asn Gln Ala Ser Tyr Ser Ile Gln Ala Ser Ala
            610                 615                 620

Gly Ser Tyr Val Ala Ile Ser Lys Asp Gly Val Leu Tyr Gly Thr Gly
625                 630                 635                 640

Val Ala Asn Ala Ser Gly Val Ala Thr Val Ser Met Thr Lys Gln Ile
                645                 650                 655

Thr Glu Asn Gly Asn Tyr Asp Val Val Ile Thr Arg Ser Asn Tyr Leu
                660                 665                 670

Pro Val Ile Lys Gln Ile Gln Val Gly Glu Pro Ser Pro Tyr Gln Pro
            675                 680                 685

Val Ser Asn Leu Thr Ala Thr Thr Gln Gly Gln Lys Val Thr Leu Lys
            690                 695                 700

Trp Glu Ala Pro Ser Ala Lys Lys Ala Glu Gly Ser Arg Glu Val Lys
705                 710                 715                 720
```

```
Arg Ile Gly Asp Gly Leu Phe Val Thr Ile Glu Pro Ala Asn Asp Val
                725                 730                 735

Arg Ala Asn Glu Ala Lys Val Val Leu Ala Ala Asp Asn Val Trp Gly
            740                 745                 750

Asp Asn Thr Gly Tyr Gln Phe Leu Leu Asp Ala Asp His Asn Thr Phe
        755                 760                 765

Gly Ser Val Ile Pro Ala Thr Gly Pro Leu Phe Thr Gly Thr Ala Ser
    770                 775                 780

Ser Asn Leu Tyr Ser Ala Asn Phe Glu Tyr Leu Ile Pro Ala Asn Ala
785                 790                 795                 800

Asp Pro Val Val Thr Thr Gln Asn Ile Ile Val Thr Gly Gln Gly Glu
                805                 810                 815

Val Val Ile Pro Gly Gly Val Tyr Asp Tyr Cys Ile Thr Asn Pro Glu
            820                 825                 830

Pro Ala Ser Gly Lys Met Trp Ile Ala Gly Asp Gly Gly Asn Gln Pro
        835                 840                 845

Ala Arg Tyr Asp Asp Phe Thr Phe Glu Ala Gly Lys Lys Tyr Thr Phe
    850                 855                 860

Thr Met Arg Arg Ala Gly Met Gly Asp Gly Thr Asp Met Glu Val Glu
865                 870                 875                 880

Asp Asp Ser Pro Ala Ser Tyr Thr Tyr Thr Val Tyr Arg Asp Gly Thr
                885                 890                 895

Lys Ile Lys Glu Gly Leu Thr Ala Thr Thr Phe Glu Glu Asp Gly Val
            900                 905                 910

Ala Ala Gly Asn His Glu Tyr Cys Val Glu Val Lys Tyr Thr Ala Gly
        915                 920                 925

Val Ser Pro Lys Val Cys Lys Asp Val Thr Val Glu Gly Ser Asn Glu
    930                 935                 940

Phe Ala Pro Val Gln Asn Leu Thr Gly Ser Ser Val Gly Gln Lys Val
945                 950                 955                 960

Thr Leu Lys Trp Asp Ala Pro Asn Gly Thr Pro Asn Pro Asn Pro Asn
                965                 970                 975

Pro Asn Pro Asn Pro Gly Thr Thr Leu Ser Glu Ser Phe Glu Asn Gly
            980                 985                 990

Ile Pro Ala Ser Trp Lys Thr Ile Asp Ala Asp Gly Asp Gly His Gly
        995                 1000                1005

Trp Lys Pro Gly Asn Ala Pro Gly Ile Ala Gly Tyr Asn Ser Asn
    1010                1015                1020

Gly Cys Val Tyr Ser Glu Ser Phe Gly Leu Gly Gly Ile Gly Val
    1025                1030                1035

Leu Thr Pro Asp Asn Tyr Leu Ile Thr Pro Ala Leu Asp Leu Pro
    1040                1045                1050

Asn Gly Gly Lys Leu Thr Phe Trp Val Cys Ala Gln Asp Ala Asn
    1055                1060                1065

Tyr Ala Ser Glu His Tyr Ala Val Tyr Ala Ser Ser Thr Gly Asn
    1070                1075                1080

Asp Ala Ser Asn Phe Thr Asn Ala Leu Leu Glu Glu Thr Ile Thr
    1085                1090                1095

Ala Lys Gly Val Arg Ser Pro Lys Ala Ile Arg Gly Arg Ile Gln
    1100                1105                1110

Gly Thr Trp Arg Gln Lys Thr Val Asp Leu Pro Ala Gly Thr Lys
    1115                1120                1125
```

```
Tyr Val Ala Phe Arg His Phe Gln Ser Thr Asp Met Phe Tyr Ile
1130                1135                1140

Asp Leu Asp Glu Val Glu Ile Lys Ala Asn Gly Lys Arg Ala Asp
1145                1150                1155

Phe Thr Glu Thr Phe Glu Ser Ser Thr His Gly Glu Ala Pro Ala
1160                1165                1170

Glu Trp Thr Thr Ile Asp Ala Asp Gly Asp Gln Gly Trp Leu
1175                1180                1185

Cys Leu Ser Ser Gly Gln Leu Asp Trp Leu Thr Ala His Gly Gly
1190                1195                1200

Ser Asn Val Val Ser Ser Phe Ser Trp Asn Gly Met Ala Leu Asn
1205                1210                1215

Pro Asp Asn Tyr Leu Ile Ser Lys Asp Val Thr Gly Ala Thr Lys
1220                1225                1230

Val Lys Tyr Tyr Tyr Ala Val Asn Asp Gly Phe Pro Gly Asp His
1235                1240                1245

Tyr Ala Val Met Ile Ser Lys Thr Gly Thr Asn Ala Gly Asp Phe
1250                1255                1260

Thr Val Val Phe Glu Glu Thr Pro Asn Gly Ile Asn Lys Gly Gly
1265                1270                1275

Ala Arg Phe Gly Leu Ser Thr Glu Ala Asn Gly Ala Lys Pro Gln
1280                1285                1290

Ser Val Trp Ile Glu Arg Thr Val Asp Leu Pro Ala Gly Thr Lys
1295                1300                1305

Tyr Val Ala Phe Arg His Tyr Asn Cys Ser Asp Leu Asn Tyr Ile
1310                1315                1320

Leu Leu Asp Asp Ile Gln Phe Thr Met Gly Gly Ser Pro Thr Pro
1325                1330                1335

Thr Asp Tyr Thr Tyr Thr Val Tyr Arg Asp Gly Thr Lys Ile Lys
1340                1345                1350

Glu Gly Leu Thr Glu Thr Thr Phe Glu Gly Asp Gly Val Ala Thr
1355                1360                1365

Gly Asn His Glu Tyr Cys Val Glu Val Lys Tyr Thr Ala Gly Val
1370                1375                1380

Ser Pro Lys Lys Cys Val Asn Val Thr Val Asn Ser Thr Gln Phe
1385                1390                1395

Asn Pro Val Gln Asn Leu Thr Ala Glu Gln Ala Pro Asn Ser Met
1400                1405                1410

Asp Ala Ile Leu Lys Trp Asn Ala Pro Ala Ser Lys Arg Ala Glu
1415                1420                1425

Val Leu Asn Glu Asp Phe Glu Asn Gly Ile Pro Ala Ser Trp Lys
1430                1435                1440

Thr Ile Asp Ala Asp Gly Asp Gly Asn Asn Trp Thr Thr Pro
1445                1450                1455

Pro Pro Gly Gly Ser Ser Phe Ala Gly His Asn Ser Ala Ile Cys
1460                1465                1470

Val Ser Ser Ala Ser Tyr Ile Asn Phe Glu Gly Pro Gln Asn Pro
1475                1480                1485

Asp Asn Tyr Leu Val Thr Pro Glu Leu Ser Leu Pro Gly Gly Gly
1490                1495                1500

Thr Leu Thr Phe Trp Val Cys Ala Gln Asp Ala Asn Tyr Ala Ser
1505                1510                1515

Glu His Tyr Ala Val Tyr Ala Ser Ser Thr Gly Asn Asp Ala Ser
```

Asn Phe Ala Asn Ala Leu Leu Glu Glu Val Leu Thr Ala Lys Thr
    1535                1540                1545

Val Val Thr Ala Pro Glu Ala Ile Arg Gly Thr Arg Ala Gln Gly
    1550                1555                1560

Thr Trp Tyr Gln Lys Thr Val Gln Leu Pro Ala Gly Thr Lys Tyr
    1565                1570                1575

Val Ala Phe Arg His Phe Gly Cys Thr Asp Phe Phe Trp Ile Asn
    1580                1585                1590

Leu Asp Asp Val Val Ile Thr Ser Gly Asn Ala Pro Ser Tyr Thr
    1595                1600                1605

Tyr Thr Ile Tyr Arg Asn Asn Thr Gln Ile Ala Ser Gly Val Thr
    1610                1615                1620

Glu Thr Thr Tyr Arg Asp Pro Asp Leu Ala Thr Gly Phe Tyr Thr
    1625                1630                1635

Tyr Gly Val Lys Val Val Tyr Pro Asn Gly Glu Ser Ala Ile Glu
    1640                1645                1650

Thr Ala Thr Leu Asn Ile Thr Ser Leu Ala Asp Val Thr Ala Gln
    1655                1660                1665

Lys Pro Tyr Thr Leu Thr Val Val Gly Lys Thr Ile Thr Val Thr
    1670                1675                1680

Cys Gln Gly Glu Ala Met Ile Tyr Asp Met Asn Gly Arg Arg Leu
    1685                1690                1695

Ala Ala Gly Arg Asn Thr Val Val Tyr Thr Ala Gln Gly Gly His
    1700                1705                1710

Tyr Ala Val Met Val Val Asp Gly Lys Ser Tyr Val Glu Lys
    1715                1720                1725

Leu Ala Val Lys
    1730

<210> SEQ ID NO 63
<211> LENGTH: 2164
<212> TYPE: PRT
<213> ORGANISM: Porphyromonas gingivalis

<400> SEQUENCE: 63

Met Arg Lys Leu Asn Ser Leu Phe Ser Leu Ala Val Leu Leu Ser Leu
1               5                   10                  15

Leu Cys Trp Gly Gln Thr Ala Ala Gln Gly Gly Pro Lys Thr Ala
                20                  25                  30

Pro Ser Val Thr His Gln Ala Val Gln Lys Gly Ile Arg Thr Ser Lys
                35                  40                  45

Ala Lys Asp Leu Arg Asp Pro Ile Pro Ala Gly Met Ala Arg Ile Ile
50                  55                  60

Leu Glu Ala His Asp Val Trp Glu Asp Gly Thr Gly Tyr Gln Met Leu
65                  70                  75                  80

Trp Asp Ala Asp His Asn Gln Tyr Gly Ala Ser Ile Pro Glu Glu Ser
                85                  90                  95

Phe Trp Phe Ala Asn Gly Thr Ile Pro Ala Gly Leu Tyr Asp Pro Phe
                100                 105                 110

Glu Tyr Lys Val Pro Val Asn Ala Asp Ala Ser Phe Ser Pro Thr Asn
                115                 120                 125

Phe Val Leu Asp Gly Thr Ala Ser Ala Asp Ile Pro Ala Gly Thr Tyr
                130                 135                 140

```
Asp Tyr Val Ile Ile Asn Pro Asn Pro Gly Ile Tyr Ile Val Gly
145                 150                 155                 160

Glu Gly Val Ser Lys Gly Asn Asp Tyr Val Glu Ala Gly Lys Thr
            165                 170                 175

Tyr His Phe Thr Val Gln Arg Gln Gly Pro Gly Asp Ala Ala Ser Val
                180                 185                 190

Val Val Thr Gly Glu Gly Gly Asn Glu Phe Ala Pro Val Gln Asn Leu
        195                 200                 205

Gln Trp Ser Val Ser Gly Gln Thr Val Thr Leu Thr Trp Gln Ala Pro
210                 215                 220

Ala Ser Asp Lys Arg Thr Tyr Val Leu Asn Glu Ser Phe Asp Thr Gln
225                 230                 235                 240

Thr Leu Pro Asn Gly Trp Thr Met Ile Asp Ala Asp Gly Asp His
                245                 250                 255

Asn Trp Leu Ser Thr Ile Asn Val Tyr Asn Thr Ala Thr His Thr Gly
                260                 265                 270

Asp Gly Ala Met Phe Ser Lys Ser Trp Thr Ala Ser Gly Ala Lys
                275                 280                 285

Ile Asp Leu Ser Pro Asp Asn Tyr Leu Val Thr Pro Lys Phe Thr Val
290                 295                 300

Pro Glu Asn Gly Lys Leu Ser Tyr Trp Val Ser Ser Gln Glu Pro Trp
305                 310                 315                 320

Thr Asn Glu His Tyr Gly Val Phe Leu Ser Thr Thr Gly Asn Glu Ala
                325                 330                 335

Ala Asn Phe Thr Ile Lys Leu Leu Glu Glu Thr Leu Gly Ser Gly Lys
                340                 345                 350

Pro Ala Pro Met Asn Leu Val Lys Ser Glu Gly Val Lys Ala Pro Ala
                355                 360                 365

Pro Tyr Gln Glu Arg Thr Ile Asp Leu Ser Ala Tyr Ala Gly Gln Gln
                370                 375                 380

Val Tyr Leu Ala Phe Arg His Phe Gly Cys Thr Gly Ile Phe Arg Leu
385                 390                 395                 400

Tyr Leu Asp Asp Val Ala Val Ser Gly Glu Gly Ser Ser Asn Asp Tyr
                405                 410                 415

Thr Tyr Thr Val Tyr Arg Asp Asn Val Val Ile Ala Gln Asn Leu Thr
                420                 425                 430

Ala Thr Thr Phe Asn Gln Glu Asn Val Ala Pro Gly Gln Tyr Asn Tyr
                435                 440                 445

Cys Val Glu Val Lys Tyr Thr Ala Gly Val Ser Pro Lys Val Cys Lys
450                 455                 460

Asp Val Thr Val Glu Gly Ser Asn Glu Phe Ala Pro Val Gln Asn Leu
465                 470                 475                 480

Thr Gly Ser Ala Val Gly Gln Lys Val Thr Leu Lys Trp Asp Ala Pro
                485                 490                 495

Asn Gly Thr Pro Asn Pro Asn Pro Gly Thr Thr Thr Leu Ser Glu Ser
                500                 505                 510

Phe Glu Asn Gly Ile Pro Ala Ser Trp Lys Thr Ile Asp Ala Asp Gly
                515                 520                 525

Asp Gly Asn Asn Trp Thr Thr Thr Pro Pro Gly Gly Ser Ser Phe
                530                 535                 540

Ala Gly His Asn Ser Ala Ile Cys Val Ser Ser Ala Ser Tyr Ile Asn
545                 550                 555                 560

Phe Glu Gly Pro Gln Asn Pro Asp Asn Tyr Leu Val Thr Pro Glu Leu
```

-continued

```
                565                 570                 575
Ser Leu Pro Asn Gly Gly Thr Leu Thr Phe Trp Val Cys Ala Gln Asp
            580                 585                 590

Ala Asn Tyr Ala Ser Glu His Tyr Ala Val Tyr Ala Ser Ser Thr Gly
        595                 600                 605

Asn Asp Ala Ser Asn Phe Ala Asn Leu Leu Glu Glu Val Leu Thr
    610                 615                 620

Ala Lys Thr Val Val Thr Ala Pro Glu Ala Ile Arg Gly Thr Arg Val
625                 630                 635                 640

Gln Gly Thr Trp Tyr Gln Lys Thr Val Gln Leu Pro Ala Gly Thr Lys
                645                 650                 655

Tyr Val Ala Phe Arg His Phe Gly Cys Thr Asp Phe Phe Trp Ile Asn
            660                 665                 670

Leu Asp Asp Val Glu Ile Lys Ala Asn Gly Lys Arg Ala Asp Phe Thr
        675                 680                 685

Glu Thr Phe Glu Ser Ser Thr His Gly Glu Ala Pro Ala Glu Trp Thr
    690                 695                 700

Thr Ile Asp Ala Asp Gly Asp Gly Gln Gly Trp Leu Cys Leu Ser Ser
705                 710                 715                 720

Gly Gln Leu Gly Trp Leu Thr Ala His Gly Thr Asn Val Ala
                725                 730                 735

Ser Phe Ser Trp Asn Gly Met Ala Leu Asn Pro Asp Asn Tyr Leu Ile
            740                 745                 750

Ser Lys Asp Val Thr Gly Ala Thr Lys Val Lys Tyr Tyr Ala Val
        755                 760                 765

Asn Asp Gly Phe Pro Gly Asp His Tyr Ala Val Met Ile Ser Lys Thr
    770                 775                 780

Gly Thr Asn Ala Gly Asp Phe Thr Val Val Phe Glu Glu Thr Pro Asn
785                 790                 795                 800

Gly Ile Asn Lys Gly Gly Ala Arg Phe Gly Leu Ser Thr Glu Ala Asn
                805                 810                 815

Gly Ala Lys Pro Gln Ser Val Trp Ile Glu Arg Thr Val Asp Leu Pro
            820                 825                 830

Ala Gly Thr Lys Tyr Val Ala Phe Arg His Tyr Asn Cys Ser Asp Leu
        835                 840                 845

Asn Tyr Ile Leu Leu Asp Asp Ile Gln Phe Thr Met Gly Gly Ser Pro
    850                 855                 860

Thr Pro Thr Asp Tyr Thr Tyr Thr Val Tyr Arg Asp Gly Thr Lys Ile
865                 870                 875                 880

Lys Glu Gly Leu Thr Glu Thr Phe Glu Glu Asp Gly Val Ala Thr
                885                 890                 895

Gly Asn His Glu Tyr Cys Val Glu Val Lys Tyr Thr Ala Gly Val Ser
            900                 905                 910

Pro Lys Glu Cys Val Asn Val Thr Val Asp Pro Val Gln Phe Asn Pro
        915                 920                 925

Val Gln Asn Leu Thr Gly Ser Ala Val Gly Gln Lys Val Thr Leu Lys
    930                 935                 940

Trp Asp Ala Pro Asn Gly Thr Pro Asn Pro Asn Pro Gly Thr Thr Thr
945                 950                 955                 960

Leu Ser Glu Ser Phe Glu Asn Gly Ile Pro Ala Ser Trp Lys Thr Ile
                965                 970                 975

Asp Ala Asp Gly Asp Gly Asn Asn Trp Thr Thr Thr Pro Pro Gly
            980                 985                 990
```

```
Gly Thr Ser Phe Ala Gly His Asn  Ser Ala Ile Cys Val  Ser Ser Ala
        995                 1000                 1005

Ser Tyr  Ile Asn Phe Glu Gly  Pro Gln Asn Pro Asp  Asn Tyr Leu
    1010                 1015                 1020

Val Thr  Pro Glu Leu Ser Leu  Pro Asn Gly Gly Thr  Leu Thr Phe
    1025                 1030                 1035

Trp Val  Cys Ala Gln Asp Ala  Asn Tyr Ala Ser Glu  His Tyr Ala
    1040                 1045                 1050

Val Tyr  Ala Ser Ser Thr Gly  Asn Asp Ala Ser Asn  Phe Ala Asn
    1055                 1060                 1065

Ala Leu  Leu Glu Glu Val Leu  Thr Ala Lys Thr Val  Val Thr Ala
    1070                 1075                 1080

Pro Glu  Ala Ile Arg Gly Thr  Arg Val Gln Gly Thr  Trp Tyr Gln
    1085                 1090                 1095

Lys Thr  Val Gln Leu Pro Ala  Gly Thr Lys Tyr Val  Ala Phe Arg
    1100                 1105                 1110

His Phe  Gly Cys Thr Asp Phe  Phe Trp Ile Asn Leu  Asp Asp Val
    1115                 1120                 1125

Glu Ile  Lys Ala Asn Gly Lys  Arg Ala Asp Phe Thr  Glu Thr Phe
    1130                 1135                 1140

Glu Ser  Ser Thr His Gly Glu  Ala Pro Ala Glu Trp  Thr Thr Ile
    1145                 1150                 1155

Asp Ala  Asp Gly Asp Gly Gln  Gly Trp Leu Cys Leu  Ser Ser Gly
    1160                 1165                 1170

Gln Leu  Asp Trp Leu Thr Ala  His Gly Gly Thr Asn  Val Val Ala
    1175                 1180                 1185

Ser Phe  Ser Trp Asn Gly Met  Ala Leu Asn Pro Asp  Asn Tyr Leu
    1190                 1195                 1200

Ile Ser  Lys Asp Val Thr Gly  Ala Thr Lys Val Lys  Tyr Tyr Tyr
    1205                 1210                 1215

Ala Val  Asn Asp Gly Phe Pro  Gly Asp His Tyr Ala  Val Met Ile
    1220                 1225                 1230

Ser Lys  Thr Gly Thr Asn Ala  Gly Asp Phe Thr Val  Val Phe Glu
    1235                 1240                 1245

Glu Thr  Pro Asn Gly Ile Asn  Lys Gly Gly Ala Arg  Phe Gly Leu
    1250                 1255                 1260

Ser Thr  Glu Ala Asn Gly Ala  Lys Pro Gln Ser Val  Trp Ile Glu
    1265                 1270                 1275

Arg Thr  Val Asp Leu Pro Ala  Gly Thr Lys Tyr Val  Ala Phe Arg
    1280                 1285                 1290

His Tyr  Asn Cys Ser Asp Leu  Asn Tyr Ile Leu Leu  Asp Asp Ile
    1295                 1300                 1305

Gln Phe  Thr Met Gly Gly Ser  Pro Thr Pro Thr Asp  Tyr Thr Tyr
    1310                 1315                 1320

Thr Val  Tyr Arg Asp Gly Thr  Lys Ile Lys Glu Gly  Leu Thr Glu
    1325                 1330                 1335

Thr Thr  Phe Glu Glu Asp Gly  Val Ala Thr Gly Asn  His Glu Tyr
    1340                 1345                 1350

Cys Val  Glu Val Lys Tyr Thr  Ala Gly Val Ser Pro  Lys Glu Cys
    1355                 1360                 1365

Val Asn  Val Thr Val Asp Pro  Val Gln Phe Asn Pro  Val Gln Asn
    1370                 1375                 1380
```

```
Leu Thr Gly Ser Ala Val Gly Gln Lys Val Thr Leu Lys Trp Asp
    1385                1390                1395
Ala Pro Asn Gly Thr Pro Asn Pro Asn Pro Gly Thr Thr Thr Leu
1400                1405                1410
Ser Glu Ser Phe Glu Asn Gly Ile Pro Ala Ser Trp Lys Thr Ile
1415                1420                1425
Asp Ala Asp Gly Asp Gly Asn Asn Trp Thr Thr Thr Pro Pro Pro
1430                1435                1440
Gly Gly Thr Ser Phe Ala Gly His Asn Ser Ala Ile Cys Val Ser
    1445                1450                1455
Ser Ala Ser Tyr Ile Asn Phe Glu Gly Pro Gln Asn Pro Asp Asn
1460                1465                1470
Tyr Leu Val Thr Pro Glu Leu Ser Leu Pro Asn Gly Gly Thr Leu
1475                1480                1485
Thr Phe Trp Val Cys Ala Gln Asp Ala Asn Tyr Ala Ser Glu His
1490                1495                1500
Tyr Ala Val Tyr Ala Ser Ser Thr Gly Asn Asp Ala Ser Asn Phe
    1505                1510                1515
Ala Asn Ala Leu Leu Glu Glu Val Leu Thr Ala Lys Thr Val Val
1520                1525                1530
Thr Ala Pro Glu Ala Ile Arg Gly Thr Arg Val Gln Gly Thr Trp
1535                1540                1545
Tyr Gln Lys Thr Val Gln Leu Pro Ala Gly Thr Lys Tyr Val Ala
1550                1555                1560
Phe Arg His Phe Gly Cys Thr Asp Phe Phe Trp Ile Asn Leu Asp
    1565                1570                1575
Asp Val Glu Ile Lys Ala Asn Gly Lys Arg Ala Asp Phe Thr Glu
1580                1585                1590
Thr Phe Glu Ser Ser Thr His Gly Glu Ala Pro Ala Glu Trp Thr
1595                1600                1605
Thr Ile Asp Ala Asp Gly Asp Gly Gln Gly Trp Leu Cys Leu Ser
1610                1615                1620
Ser Gly Gln Leu Gly Trp Leu Thr Ala His Gly Gly Thr Asn Val
    1625                1630                1635
Val Ala Ser Phe Ser Trp Asn Gly Met Ala Leu Asn Pro Asp Asn
1640                1645                1650
Tyr Leu Ile Ser Lys Asp Val Thr Gly Ala Thr Lys Val Lys Tyr
1655                1660                1665
Tyr Tyr Ala Val Asn Asp Gly Phe Pro Gly Asp His Tyr Ala Val
1670                1675                1680
Met Ile Ser Lys Thr Gly Thr Asn Ala Gly Asp Phe Thr Val Val
    1685                1690                1695
Phe Glu Glu Thr Pro Asn Gly Ile Asn Lys Gly Gly Ala Arg Phe
1700                1705                1710
Gly Leu Ser Thr Glu Ala Asn Gly Ala Lys Pro Gln Ser Val Trp
1715                1720                1725
Ile Glu Arg Thr Val Asp Leu Pro Ala Gly Thr Lys Tyr Val Ala
1730                1735                1740
Phe Arg His Tyr Asn Cys Ser Asp Leu Asn Tyr Ile Leu Leu Asp
    1745                1750                1755
Asp Ile Gln Phe Thr Met Gly Gly Ser Pro Thr Pro Thr Asp Tyr
1760                1765                1770
Thr Tyr Thr Val Tyr Arg Asp Gly Thr Lys Ile Lys Glu Gly Leu
```

-continued

```
            1775                1780                1785
Thr Glu Thr Thr Phe Glu Glu Asp Gly Val Ala Thr Gly Asn His
        1790                1795                1800
Glu Tyr Cys Val Glu Val Lys Tyr Thr Ala Gly Val Ser Pro Lys
        1805                1810                1815
Glu Cys Val Asn Val Thr Ile Asn Pro Thr Gln Phe Asn Pro Val
        1820                1825                1830
Gln Asn Leu Thr Ala Glu Gln Ala Pro Asn Ser Met Asp Ala Ile
        1835                1840                1845
Leu Lys Trp Asn Ala Pro Ala Ser Lys Arg Ala Glu Val Leu Asn
        1850                1855                1860
Glu Asp Phe Glu Asn Gly Ile Pro Ala Ser Trp Lys Thr Ile Asp
        1865                1870                1875
Ala Asp Gly Asp Gly Asn Asn Trp Thr Thr Thr Pro Pro Pro Gly
        1880                1885                1890
Gly Ser Ser Phe Ala Gly His Asn Ser Ala Ile Cys Val Ser Ser
        1895                1900                1905
Ala Ser Tyr Ile Asn Phe Glu Gly Pro Gln Asn Pro Asp Asn Tyr
        1910                1915                1920
Leu Val Thr Pro Glu Leu Ser Leu Pro Gly Gly Gly Thr Leu Thr
        1925                1930                1935
Phe Trp Val Cys Ala Gln Asp Ala Asn Tyr Ala Ser Glu His Tyr
        1940                1945                1950
Ala Val Tyr Ala Ser Ser Thr Gly Asn Asp Ala Ser Asn Phe Ala
        1955                1960                1965
Asn Ala Leu Leu Glu Glu Val Leu Thr Ala Lys Thr Val Val Thr
        1970                1975                1980
Ala Pro Glu Ala Ile Arg Gly Thr Arg Val Gln Gly Thr Trp Tyr
        1985                1990                1995
Gln Lys Thr Val Gln Leu Pro Ala Gly Thr Lys Tyr Val Ala Phe
        2000                2005                2010
Arg His Phe Gly Cys Thr Asp Phe Phe Trp Ile Asn Leu Asp Asp
        2015                2020                2025
Val Val Ile Thr Ser Gly Asn Ala Pro Ser Tyr Thr Tyr Thr Ile
        2030                2035                2040
Tyr Arg Asn Asn Thr Gln Ile Ala Ser Gly Val Thr Glu Thr Thr
        2045                2050                2055
Tyr Arg Asp Pro Asp Leu Ala Thr Gly Phe Tyr Thr Tyr Gly Val
        2060                2065                2070
Lys Val Val Tyr Pro Asn Gly Glu Ser Ala Ile Glu Thr Ala Thr
        2075                2080                2085
Leu Asn Ile Thr Ser Leu Ala Asp Val Thr Ala Gln Lys Pro Tyr
        2090                2095                2100
Thr Leu Thr Val Val Gly Lys Thr Ile Thr Val Thr Cys Gln Gly
        2105                2110                2115
Glu Ala Met Ile Tyr Asp Met Asn Gly Arg Arg Leu Ala Ala Gly
        2120                2125                2130
Arg Asn Thr Val Val Tyr Thr Ala Gln Gly Gly His Tyr Ala Val
        2135                2140                2145
Met Val Val Val Asp Gly Lys Ser Tyr Val Glu Lys Leu Ala Val
        2150                2155                2160
Lys
```

```
<210> SEQ ID NO 64
<211> LENGTH: 8
<212> TYPE: PRT
<213> ORGANISM: Porphyromonas gingivalis
<220> FEATURE:
<221> NAME/KEY: MISC_FEATURE
<222> LOCATION: (2)..(2)
<223> OTHER INFORMATION: X can be either S or Y
<220> FEATURE:
<221> NAME/KEY: MISC_FEATURE
<222> LOCATION: (3)..(3)
<223> OTHER INFORMATION: X can be either Y or S
<220> FEATURE:
<221> NAME/KEY: MISC_FEATURE
<222> LOCATION: (6)..(6)
<223> OTHER INFORMATION: X can be either P or S
<220> FEATURE:
<221> NAME/KEY: MISC_FEATURE
<222> LOCATION: (7)..(7)
<223> OTHER INFORMATION: X can be either K or Q
<220> FEATURE:
<221> NAME/KEY: MISC_FEATURE
<222> LOCATION: (8)..(8)
<223> OTHER INFORMATION: X can be either I or V

<400> SEQUENCE: 64

Asp Xaa Xaa Trp Asn Xaa Xaa Xaa
1               5

<210> SEQ ID NO 65
<211> LENGTH: 7
<212> TYPE: PRT
<213> ORGANISM: Porphyromonas gingivalis

<400> SEQUENCE: 65

Asn Ser Tyr Trp Gly Glu Asp
1               5

<210> SEQ ID NO 66
<211> LENGTH: 11
<212> TYPE: PRT
<213> ORGANISM: Porphyromonas gingivalis
<220> FEATURE:
<221> NAME/KEY: MISC_FEATURE
<222> LOCATION: (4)..(4)
<223> OTHER INFORMATION: X can be either V or I

<400> SEQUENCE: 66

Ile Gly Asn Xaa Thr His Ile Gly Ala His Tyr
1               5                   10

<210> SEQ ID NO 67
<211> LENGTH: 8
<212> TYPE: PRT
<213> ORGANISM: Porphyromonas gingivalis

<400> SEQUENCE: 67

Glu Gly Gly Pro Ser Ala Asp Asn
1               5

<210> SEQ ID NO 68
<211> LENGTH: 7
<212> TYPE: PRT
<213> ORGANISM: Porphyromonas gingivalis
<220> FEATURE:
<221> NAME/KEY: MISC_FEATURE
<222> LOCATION: (1)..(1)
<223> OTHER INFORMATION: X can be either N or D
<220> FEATURE:
<221> NAME/KEY: MISC_FEATURE
```

-continued

```
<222> LOCATION: (3)..(3)
<223> OTHER INFORMATION: X can be either S or Y
<220> FEATURE:
<221> NAME/KEY: MISC_FEATURE
<222> LOCATION: (6)..(6)
<223> OTHER INFORMATION: X can be either S or P

<400> SEQUENCE: 68

Xaa Gln Xaa Trp Ala Xaa Pro
1               5

<210> SEQ ID NO 69
<211> LENGTH: 23
<212> TYPE: PRT
<213> ORGANISM: Porphyromonas gingivalis

<400> SEQUENCE: 69

Pro Val Ser Asn Leu Thr Ala Thr Thr Gln Gly Gln Lys Val Thr Leu
1               5                   10                  15

Lys Trp Asp Ala Pro Ser Thr
            20

<210> SEQ ID NO 70
<211> LENGTH: 23
<212> TYPE: PRT
<213> ORGANISM: Porphyromonas gingivalis

<400> SEQUENCE: 70

Pro Val Ser Asn Leu Thr Ala Thr Thr Gln Gly Gln Lys Val Thr Leu
1               5                   10                  15

Lys Trp Glu Ala Pro Ser Ala
            20

<210> SEQ ID NO 71
<211> LENGTH: 23
<212> TYPE: PRT
<213> ORGANISM: Porphyromonas gingivalis

<400> SEQUENCE: 71

Pro Val Gln Asn Leu Thr Gly Ser Ser Val Gly Gln Lys Val Thr Leu
1               5                   10                  15

Lys Trp Asp Ala Pro Ser Thr
            20

<210> SEQ ID NO 72
<211> LENGTH: 23
<212> TYPE: PRT
<213> ORGANISM: Porphyromonas gingivalis

<400> SEQUENCE: 72

Pro Val Gln Asn Leu Thr Gly Ser Ala Val Gly Gln Lys Val Thr Leu
1               5                   10                  15

Lys Trp Asp Ala Pro Asn Gly
            20

<210> SEQ ID NO 73
<211> LENGTH: 23
<212> TYPE: PRT
<213> ORGANISM: Porphyromonas gingivalis

<400> SEQUENCE: 73

Pro Val Lys Asn Leu Lys Ala Gln Pro Asp Gly Gly Asp Val Val Leu
1               5                   10                  15
```

```
Lys Trp Glu Ala Pro Ser Ala
            20

<210> SEQ ID NO 74
<211> LENGTH: 23
<212> TYPE: PRT
<213> ORGANISM: Porphyromonas gingivalis

<400> SEQUENCE: 74

Pro Val Gln Asn Leu Thr Ala Glu Gln Ala Pro Asn Ser Met Asp Ala
1               5                   10                  15

Ile Leu Lys Trp Asn Ala Pro
            20

<210> SEQ ID NO 75
<211> LENGTH: 24
<212> TYPE: PRT
<213> ORGANISM: Porphyromonas gingivalis

<400> SEQUENCE: 75

Pro Val Gln Asn Leu Thr Gln Trp Ser Val Ser Gly Gln Thr Val Thr
1               5                   10                  15

Leu Thr Trp Gln Ala Pro Ala Ser
            20

<210> SEQ ID NO 76
<211> LENGTH: 27
<212> TYPE: PRT
<213> ORGANISM: Porphyromonas gingivalis

<400> SEQUENCE: 76

Tyr Thr Tyr Thr Val Tyr Arg Asp Gly Thr Lys Ile Lys Glu Gly Leu
1               5                   10                  15

Thr Glu Thr Thr Phe Glu Glu Asp Gly Val Ala
            20                  25

<210> SEQ ID NO 77
<211> LENGTH: 27
<212> TYPE: PRT
<213> ORGANISM: Porphyromonas gingivalis

<400> SEQUENCE: 77

Tyr Thr Tyr Thr Val Tyr Arg Asp Asn Val Val Ile Ala Gln Asn Leu
1               5                   10                  15

Thr Ala Thr Thr Phe Asn Gln Glu Asn Val Ala
            20                  25

<210> SEQ ID NO 78
<211> LENGTH: 28
<212> TYPE: PRT
<213> ORGANISM: Porphyromonas gingivalis

<400> SEQUENCE: 78

Tyr Thr Tyr Thr Val Tyr Arg Asp Gly Thr Lys Ile Lys Glu Gly Leu
1               5                   10                  15

Thr Ala Glu Thr Thr Phe Glu Glu Asp Gly Val Ala
            20                  25

<210> SEQ ID NO 79
<211> LENGTH: 16
<212> TYPE: PRT
<213> ORGANISM: Porphyromonas gingivalis
<220> FEATURE:
```

```
<221> NAME/KEY: MISC_FEATURE
<222> LOCATION: (6)..(7)
<223> OTHER INFORMATION: X can be NP or NPNP or NPNPNP or NPNPNPNP or
      NPNPNPNPNP or NPNPNPNPNPNP

<400> SEQUENCE: 79

Pro Asn Gly Thr Pro Xaa Xaa Gly Thr Thr Thr Leu Ser Glu Ser Phe
1               5                   10                  15

<210> SEQ ID NO 80
<211> LENGTH: 325
<212> TYPE: PRT
<213> ORGANISM: Porphyromonas gingivalis

<400> SEQUENCE: 80

Gly Gly Pro Lys Thr Ala Pro Ser Val Thr His Gln Ala Val Gln Lys
1               5                   10                  15

Gly Ile Arg Thr Ser Lys Ala Lys Asp Leu Arg Asp Pro Ile Pro Ala
                20                  25                  30

Gly Met Ala Arg Ile Ile Leu Glu Ala His Asp Val Trp Glu Asp Gly
            35                  40                  45

Thr Gly Tyr Gln Met Leu Trp Asp Ala Asp His Asn Gln Tyr Gly Ala
    50                  55                  60

Ser Ile Pro Glu Glu Ser Phe Trp Phe Ala Asn Gly Thr Ile Pro Ala
65                  70                  75                  80

Gly Leu Tyr Asp Pro Phe Glu Tyr Lys Val Pro Val Asn Ala Asp Ala
                85                  90                  95

Ser Phe Ser Pro Thr Asn Phe Val Leu Asp Gly Thr Ala Ser Ala Asp
            100                 105                 110

Ile Pro Ala Gly Thr Tyr Asp Tyr Val Ile Asn Pro Asn Pro Gly
    115                 120                 125

Ile Ile Tyr Ile Val Gly Glu Gly Val Ser Lys Gly Asn Asp Tyr Val
130                 135                 140

Val Glu Ala Gly Lys Thr Tyr His Phe Thr Val Gln Arg Gln Gly Pro
145                 150                 155                 160

Gly Asp Ala Ala Ser Val Val Val Thr Gly Glu Gly Asn Glu Phe
                165                 170                 175

Ala Pro Val Gln Asn Leu Gln Trp Ser Val Ser Gly Gln Thr Val Thr
            180                 185                 190

Leu Thr Trp Gln Ala Pro Ala Ser Asp Lys Arg Thr Tyr Val Leu Asn
    195                 200                 205

Glu Ser Phe Asp Thr Gln Thr Leu Pro Asn Gly Trp Thr Met Ile Asp
210                 215                 220

Ala Asp Gly Asp Gly His Asn Trp Leu Ser Thr Ile Asn Val Tyr Asn
225                 230                 235                 240

Thr Ala Thr His Thr Gly Asp Gly Ala Met Phe Ser Lys Ser Trp Thr
                245                 250                 255

Ala Ser Ser Gly Ala Lys Ile Asp Leu Ser Pro Asp Asn Tyr Leu Val
            260                 265                 270

Thr Pro Lys Phe Thr Val Pro Glu Asn Gly Lys Leu Ser Tyr Trp Val
    275                 280                 285

Ser Ser Gln Glu Pro Trp Thr Asn Glu His Tyr Gly Val Phe Leu Ser
290                 295                 300

Thr Thr Gly Asn Glu Ala Ala Asn Phe Thr Ile Lys Leu Leu Glu Glu
305                 310                 315                 320

Thr Leu Gly Ser Gly
```

-continued

```
                325

<210> SEQ ID NO 81
<211> LENGTH: 260
<212> TYPE: PRT
<213> ORGANISM: Porphyromonas gingivalis

<400> SEQUENCE: 81

Ala Pro Ala Pro Tyr Gln Glu Arg Thr Ile Asp Leu Ser Ala Tyr Ala
1               5                   10                  15

Gly Gln Gln Val Tyr Leu Ala Phe Arg His Phe Gly Cys Thr Gly Ile
            20                  25                  30

Phe Arg Leu Tyr Leu Asp Asp Val Ala Val Ser Gly Glu Gly Ser Ser
        35                  40                  45

Asn Asp Tyr Thr Tyr Thr Val Tyr Arg Asp Asn Val Val Ile Ala Gln
    50                  55                  60

Asn Leu Thr Ala Thr Thr Phe Asn Gln Glu Asn Val Ala Pro Gly Gln
65                  70                  75                  80

Tyr Asn Tyr Cys Val Glu Val Lys Tyr Thr Ala Gly Val Ser Pro Lys
                85                  90                  95

Val Cys Lys Asp Val Thr Val Glu Gly Ser Asn Glu Phe Ala Pro Val
            100                 105                 110

Gln Asn Leu Thr Gly Ser Ala Val Gly Gln Lys Val Thr Leu Lys Trp
        115                 120                 125

Asp Ala Pro Asn Gly Thr Pro Asn Pro Asn Pro Gly Thr Thr Thr Leu
    130                 135                 140

Ser Glu Ser Phe Glu Asn Gly Ile Pro Ala Ser Trp Lys Thr Ile Asp
145                 150                 155                 160

Ala Asp Gly Asp Gly Asn Asn Trp Thr Thr Thr Pro Pro Gly Gly
                165                 170                 175

Ser Ser Phe Ala Gly His Asn Ser Ala Ile Cys Val Ser Ser Ala Ser
            180                 185                 190

Tyr Ile Asn Phe Glu Gly Pro Gln Asn Pro Asp Asn Tyr Leu Val Thr
        195                 200                 205

Pro Glu Leu Ser Leu Pro Asn Gly Gly Thr Leu Thr Phe Trp Val Cys
    210                 215                 220

Ala Gln Asp Ala Asn Tyr Ala Ser Glu His Tyr Ala Val Tyr Ala Ser
225                 230                 235                 240

Ser Thr Gly Asn Asp Ala Ser Asn Phe Ala Asn Ala Leu Leu Glu Glu
                245                 250                 255

Val Leu Thr Ala
            260

<210> SEQ ID NO 82
<211> LENGTH: 258
<212> TYPE: PRT
<213> ORGANISM: Porphyromonas gingivalis

<400> SEQUENCE: 82

Pro Gln Ser Val Trp Ile Glu Arg Thr Val Asp Leu Pro Ala Gly Thr
1               5                   10                  15

Lys Tyr Val Ala Phe Arg His Tyr Asn Cys Ser Asp Leu Asn Tyr Ile
            20                  25                  30

Leu Leu Asp Asp Ile Gln Phe Thr Met Gly Gly Ser Pro Thr Pro Thr
        35                  40                  45

Asp Tyr Thr Tyr Thr Val Tyr Arg Asp Gly Thr Lys Ile Lys Glu Gly
```

```
                    50                  55                  60
Leu Thr Glu Thr Thr Phe Glu Glu Asp Gly Val Ala Thr Gly Asn His
 65                  70                  75                  80

Glu Tyr Cys Val Glu Val Lys Tyr Thr Ala Gly Val Ser Pro Lys Glu
                 85                  90                  95

Cys Val Asn Val Thr Val Asp Pro Val Gln Phe Asn Pro Val Gln Asn
                100                 105                 110

Leu Thr Gly Ser Ala Val Gly Gln Lys Val Thr Leu Lys Trp Asp Ala
            115                 120                 125

Pro Asn Gly Thr Pro Asn Pro Asn Pro Gly Thr Thr Thr Leu Ser Glu
        130                 135                 140

Ser Phe Glu Asn Gly Ile Pro Ala Ser Trp Lys Thr Ile Asp Ala Asp
145                 150                 155                 160

Gly Asp Gly Asn Asn Trp Thr Thr Thr Pro Pro Gly Gly Thr Ser
                165                 170                 175

Phe Ala Gly His Asn Ser Ala Ile Cys Val Ser Ser Ala Ser Tyr Ile
                180                 185                 190

Asn Phe Glu Gly Pro Gln Asn Pro Asp Asn Tyr Leu Val Thr Pro Glu
            195                 200                 205

Leu Ser Leu Pro Asn Gly Gly Thr Leu Thr Phe Trp Val Cys Ala Gln
        210                 215                 220

Asp Ala Asn Tyr Ala Ser Glu His Tyr Ala Val Tyr Ala Ser Ser Thr
225                 230                 235                 240

Gly Asn Asp Ala Ser Asn Phe Ala Asn Ala Leu Leu Glu Glu Val Leu
                245                 250                 255

Thr Ala

<210> SEQ ID NO 83
<211> LENGTH: 15
<212> TYPE: PRT
<213> ORGANISM: Porphyromonas gingivalis

<400> SEQUENCE: 83

Pro Tyr Gln Pro Val Ser Asn Leu Thr Ala Thr Thr Gln Gly Gln
1               5                   10                  15

<210> SEQ ID NO 84
<211> LENGTH: 15
<212> TYPE: PRT
<213> ORGANISM: Porphyromonas gingivalis

<400> SEQUENCE: 84

Glu Gly Leu Thr Ala Thr Thr Phe Glu Glu Asp Gly Val Ala Ala
1               5                   10                  15

<210> SEQ ID NO 85
<211> LENGTH: 17
<212> TYPE: PRT
<213> ORGANISM: Porphyromonas gingivalis

<400> SEQUENCE: 85

Gly Thr Pro Asn Pro Asn Pro Asn Pro Asn Pro Asn Pro Asn Pro Gly
1               5                   10                  15

Thr
```